US012232948B2

United States Patent
Huynh et al.

(10) Patent No.: US 12,232,948 B2
(45) Date of Patent: Feb. 25, 2025

(54) EMBOLIC PROTECTION SYSTEM

(71) Applicant: Transaortic Medical, Inc., Morgan Hill, CA (US)

(72) Inventors: Christopher K. Huynh, San Jose, CA (US); Michael T. Carley, San Jose, CA (US); Richard S. Ginn, Powhatan, VA (US); Adam Robert Tanner, Sun Lakes, AZ (US)

(73) Assignee: Transaortic Medical, Inc., Morgan Hill, CA (US)

( * ) Notice: Subject to any disclaimer, the term of this patent is extended or adjusted under 35 U.S.C. 154(b) by 231 days.

(21) Appl. No.: 17/893,818

(22) Filed: Aug. 23, 2022

(65) Prior Publication Data
US 2024/0065821 A1 Feb. 29, 2024

(51) Int. Cl.
*A61F 2/01* (2006.01)

(52) U.S. Cl.
CPC .............. *A61F 2/013* (2013.01); *A61F 2/011* (2020.05); *A61F 2002/016* (2013.01); *A61F 2002/018* (2013.01)

(58) Field of Classification Search
CPC .... A61F 2/013; A61F 2/011; A61F 2002/016; A61F 2002/018; A61F 2/2427; A61M 1/14
See application file for complete search history.

(56) References Cited

U.S. PATENT DOCUMENTS

| 9,545,298 B2 * | 1/2017 | Ginn ..................... A61M 29/00 |
| 2003/0216774 A1 | 11/2003 | Larson |
| 2016/0128723 A1 * | 5/2016 | Ginn .................. A61B 17/3468 |
| | | 604/507 |
| 2016/0235515 A1 | 8/2016 | Merhi |
| 2020/0253709 A1 | 8/2020 | Russell et al. |
| 2022/0160506 A1 | 5/2022 | Groh |
| 2022/0226107 A1 | 7/2022 | Jones et al. |

OTHER PUBLICATIONS

"International Application Serial No. PCT/US2023/071915, International Search Report mailed Nov. 24, 2023", 4 pgs.
"International Application Serial No. PCT/US2023/071915, Written Opinion mailed Nov. 24, 2023", 4 pgs.

* cited by examiner

*Primary Examiner* — Ashley L Fishback
(74) *Attorney, Agent, or Firm* — Schwegman Lundberg & Woessner, P.A.

(57) ABSTRACT

Configurations are described for assisting execution of a percutaneous procedure while protecting the vascular pathway to the target treatment area. One example is directed to an embolic protection system for deploying a device to a distal location across a diseased vessel, the embolic protection system which may include an expandable introducer, an embolic protection device, and a loading sleeve.

8 Claims, 52 Drawing Sheets

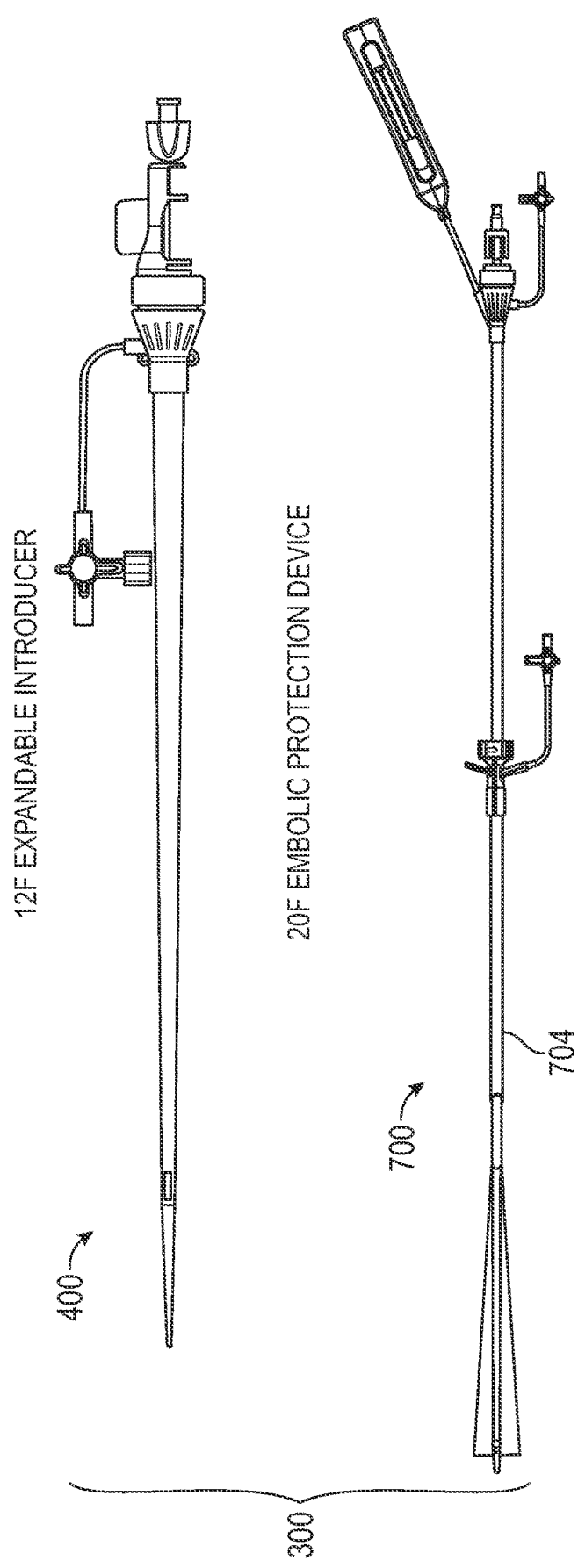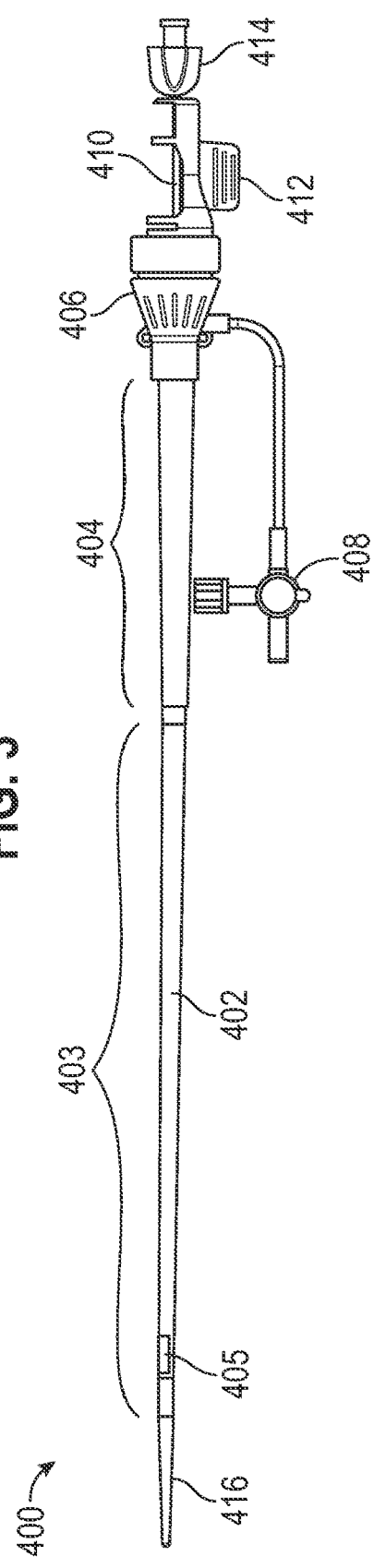
FIG. 3
FIG. 4A

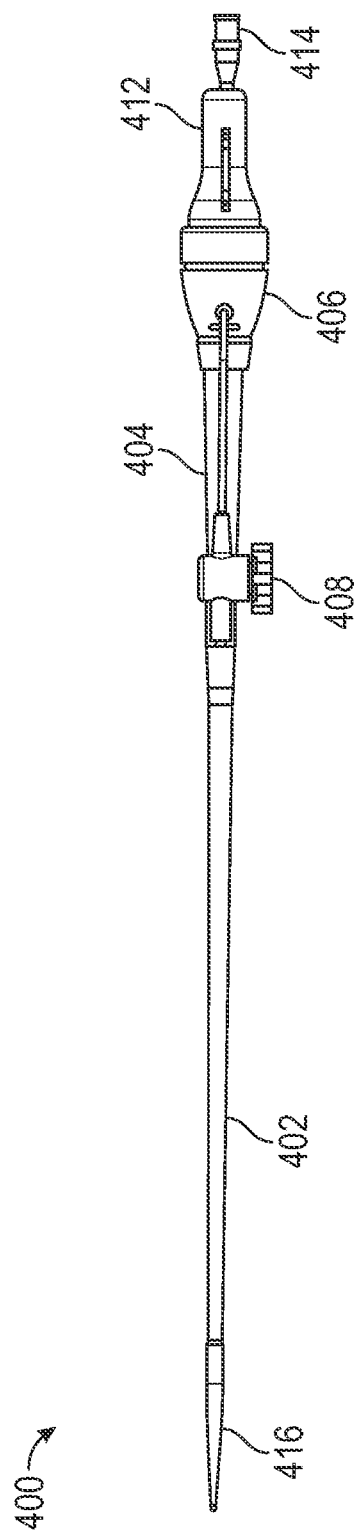
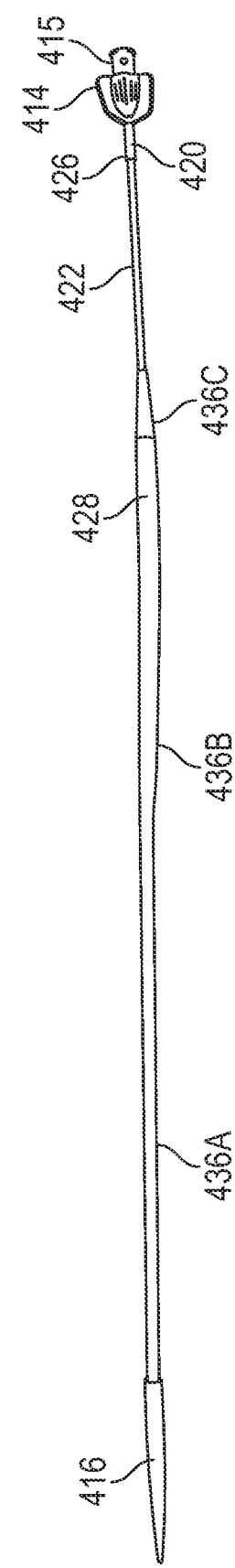
FIG. 4B
FIG. 4C

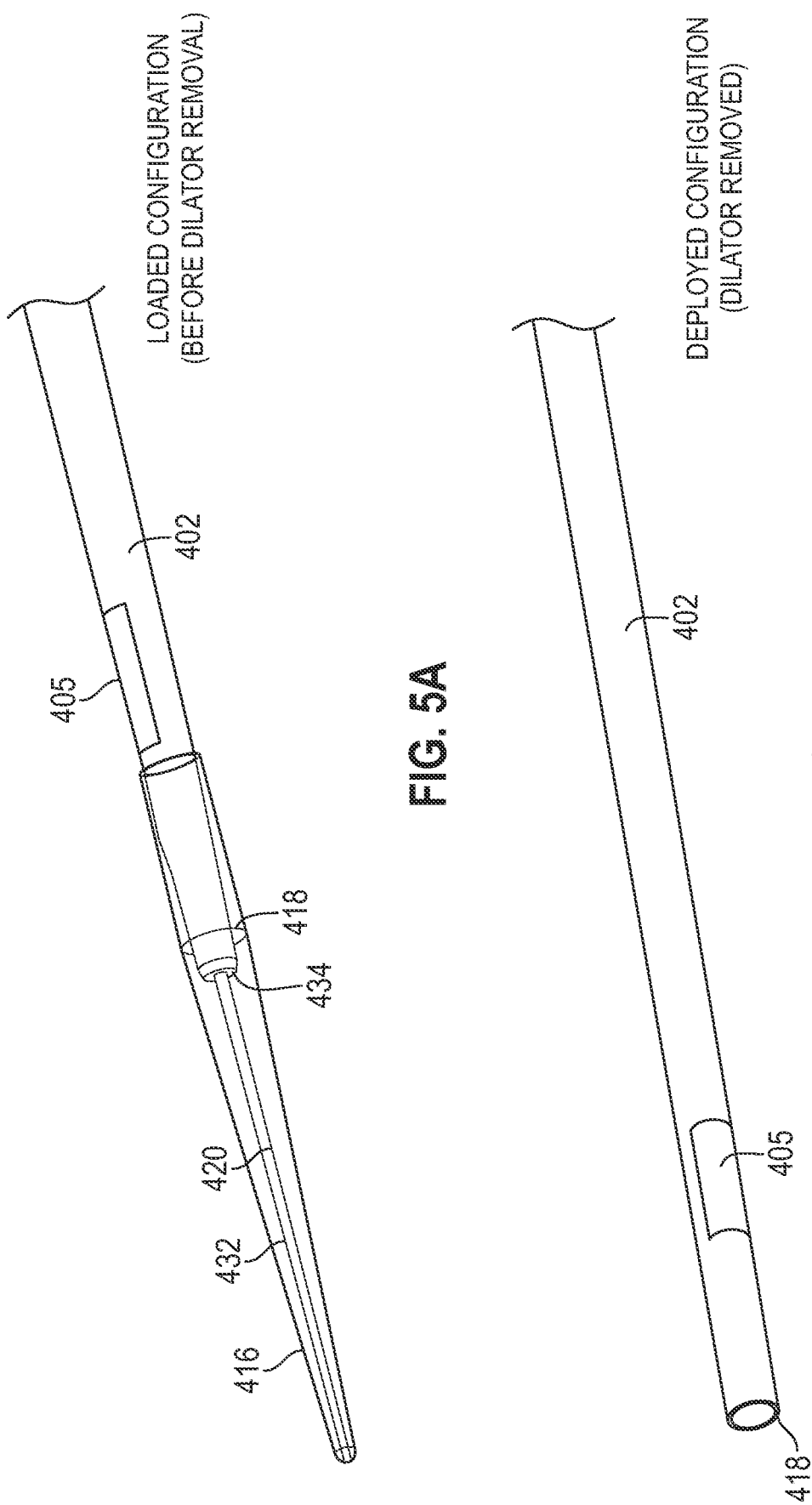

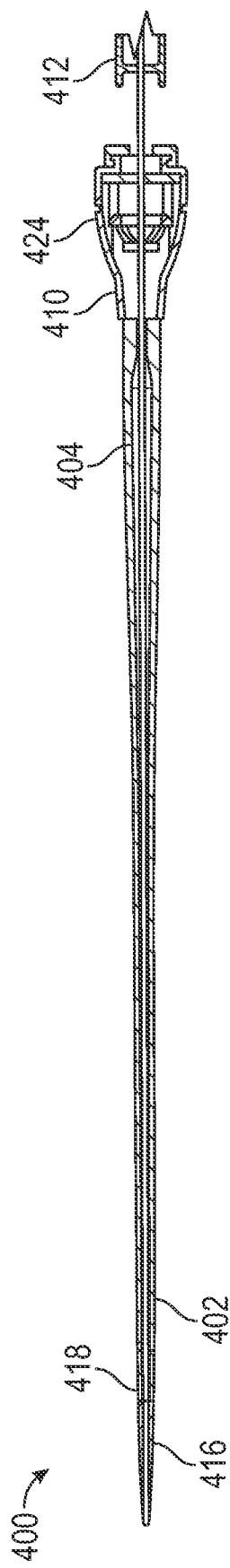
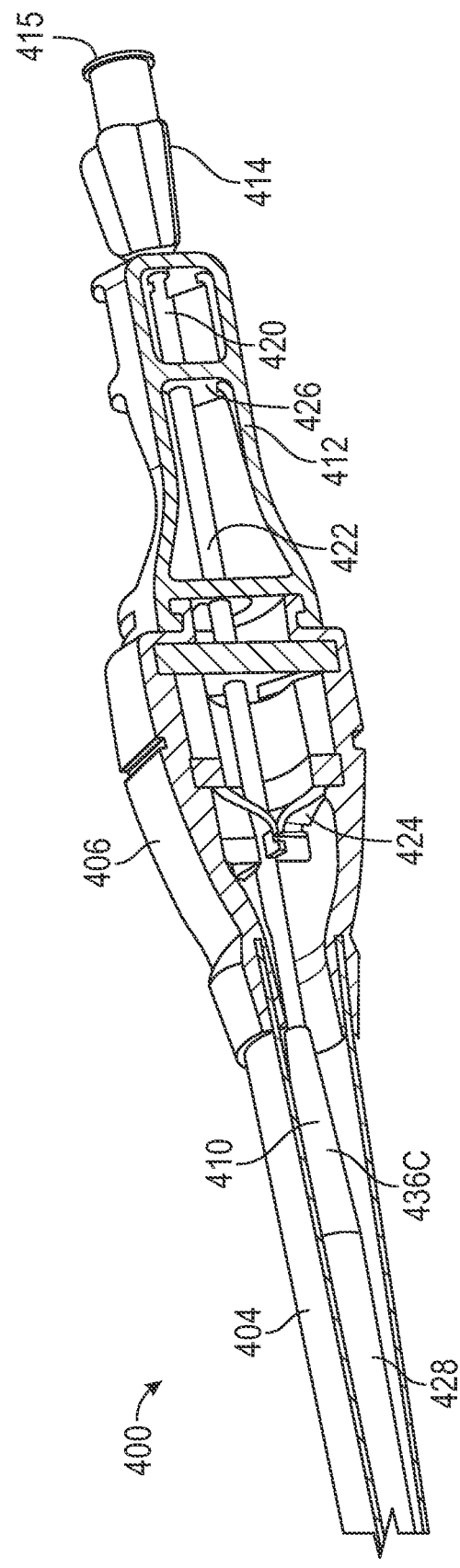
FIG. 6A
FIG. 6B

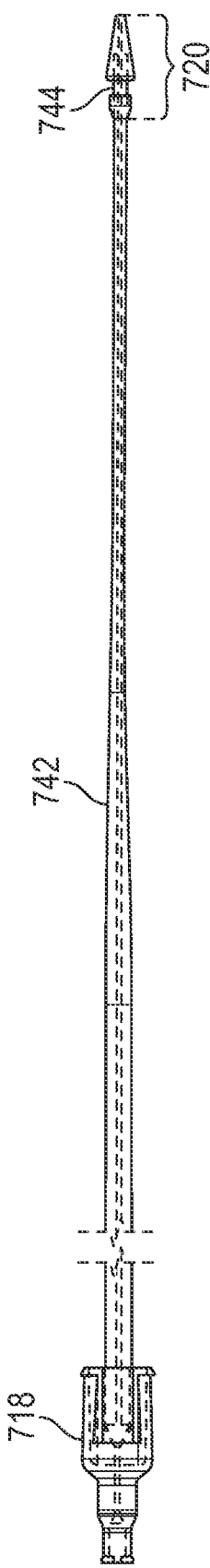
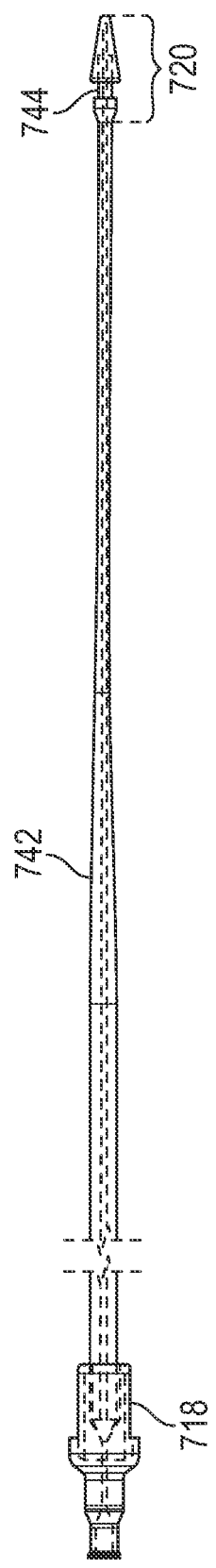
FIG. 12A
FIG. 12B

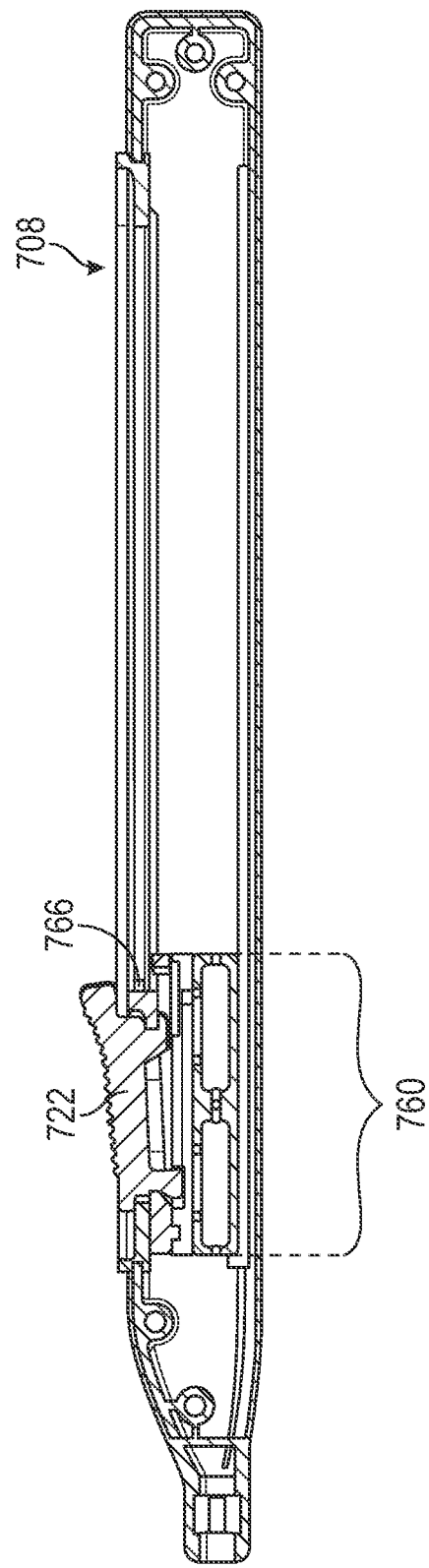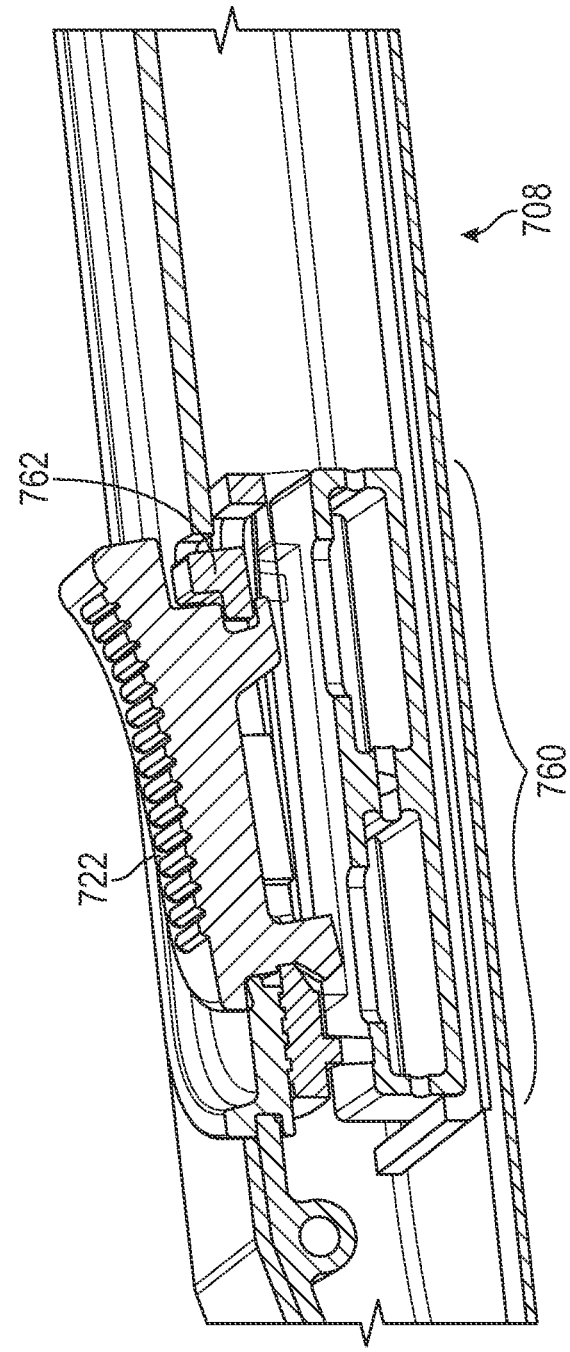
FIG. 16D
FIG. 16E

EMBOLIC PROTECTION SYSTEM

FIELD OF THE INVENTION

The present invention relates generally to devices for medical interventions conducted through vessels such as the major arteries or veins, and more particularly to devices with deployment configurations for conducting percutaneous procedures such as percutaneous valve replacement or other vascular or cardiac interventions.

BACKGROUND

Treatment of native heart valves for conditions such as valvar regurgitation using percutaneous transcatheter procedures may involve advancing a catheter or device through the vasculature to the target native valve. The target native valve may be calcified or have other disease such as unwanted plaque or thrombus attached to the native leaflets, annulus, or other anatomical regions adjacent the native valve. Rubbing, scraping or contact between the treatment catheter and the calcifications, plaque, or thrombus can result in undesirable separation of these materials from the tissue with subsequent embolization into other parts of the body. Embolization can result in serious complications including but not limited to ischemia, stroke, tissue damage, reduced lung function, etc.

Additionally, the vessels around the heart itself, such as the aorta may also be diseased and have similar unwanted buildups of plaque, thrombus, calcium, etc. and advancing the catheter through the vessel can also result in unwanted separation of these materials from the vessel walls with embolization.

It would therefore be desirable to either prevent separation of the plaques, thrombus, calcium deposits, etc. from the native heart and adjacent vessels, and in situations where this does occur, capture or prevent the materials from embolizing in the patient.

BRIEF DESCRIPTION OF THE DRAWINGS

FIG. 3 shows pictorial views of an embolic protection system comprising an expandable introducer and an embolic protection device, according to example embodiments.

FIGS. 4A-4B show respective side and top pictorial views of an example expandable introducer.

FIG. 4C shows a sheath dilator insertable inside the expandable introducer, according to example embodiments.

FIGS. 5A-5B show respective pictorial views of loaded and deployed configurations of a sheath dilator and mesh sheath of an expandable introducer, according to example embodiments.

FIGS. 6A-6B show respective sectional and enlarged part-sectional views of an expandable introducer, according to an example embodiment.

FIGS. 12A-12B show sectional views of the filter dilator of FIGS. 11A-11B.

FIGS. 16A-16E show aspects of a filter actuator, according to an example embodiment.

DETAILED DESCRIPTION

The present disclosure describes use of the devices and methods disclosed herein during treatment in or adjacent the aorta. One of skill in the art will appreciate that this is not intended to be limiting and the devices and methods disclosed herein may be used in other anatomic regions of the body. Additionally, the present disclosure describes a system which includes several components (e.g. an expandable sheath, a sheath dilator, an embolic protection device, a peel away sheath, dilator for the embolic protection device, etc.). These components may be used all together as a kit, or they may be provided individually and used individually, or they may be provided and used in any combination.

Figure 1:
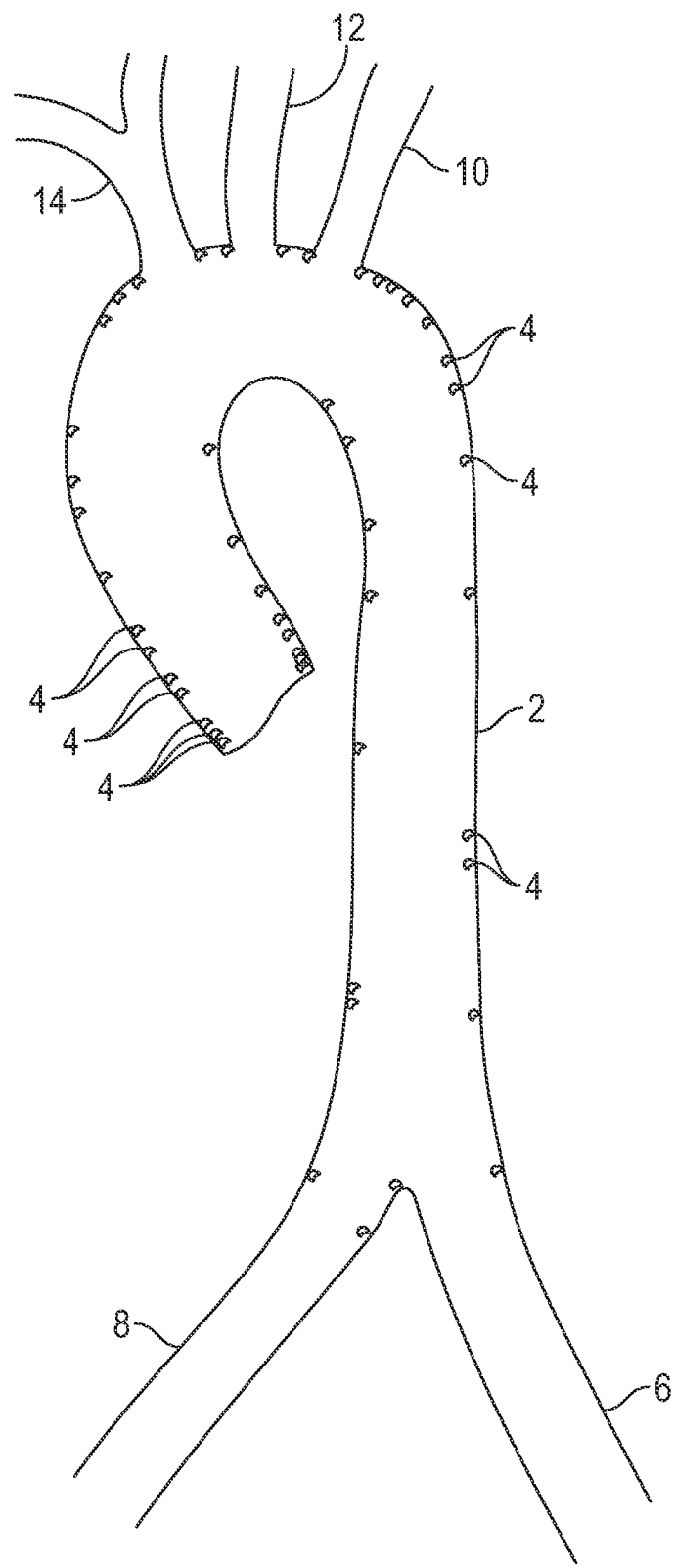
FIG. 1 shows various portions of a diseased aorta.

Referring to FIG. 1, an illustrative representation of a diseased aorta (2) is shown with deposits (4) distributed in several locations, including adjacent or within the left (6) and right (8) iliac arteries, and adjacent the junctions of the aortic arch with the left subclavian (10), left common carotid (12), and innominate artery (14). Navigating a diseased aorta (2) such as that depicted is a challenge with conventional intravascular diagnostic and/or interventional hardware.

For example, referring to FIGS. 2A-2F, a conventional instrument deployment is illustrated to demonstrate the disease-related challenges.

Figure 2A:
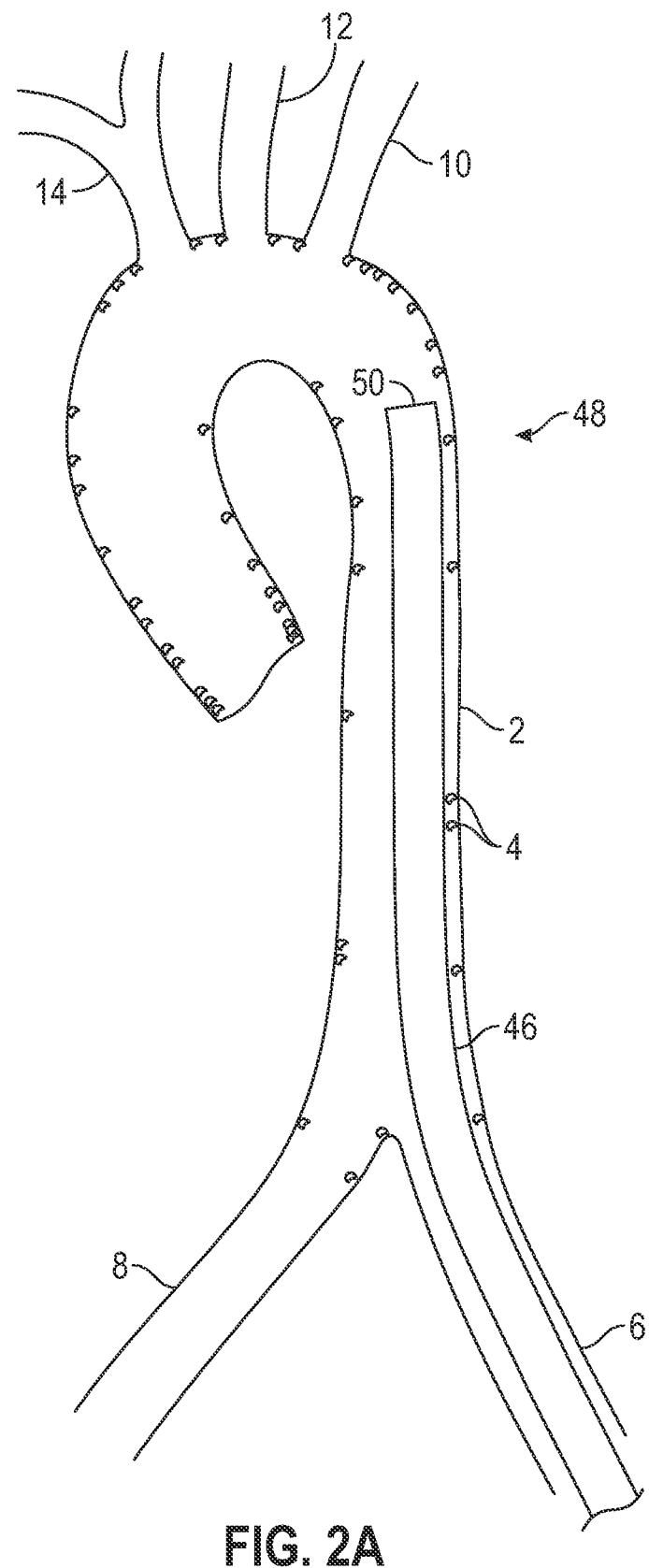
FIGS. 2A-2F show aspects of a conventional interventional device deployment through a diseased aorta.

Referring to FIG. 2A, an elongate instrument (46) is advanced in a retrograde (counter blood flow) direction through the aorta (2) with a distal tip (50, also sometimes referred to as distal end) of the instrument (46) first. The instrument (46) may be a valve deployment member or probe, a catheter or conduit for conducting various interventions, and so forth.

Figure 2B:
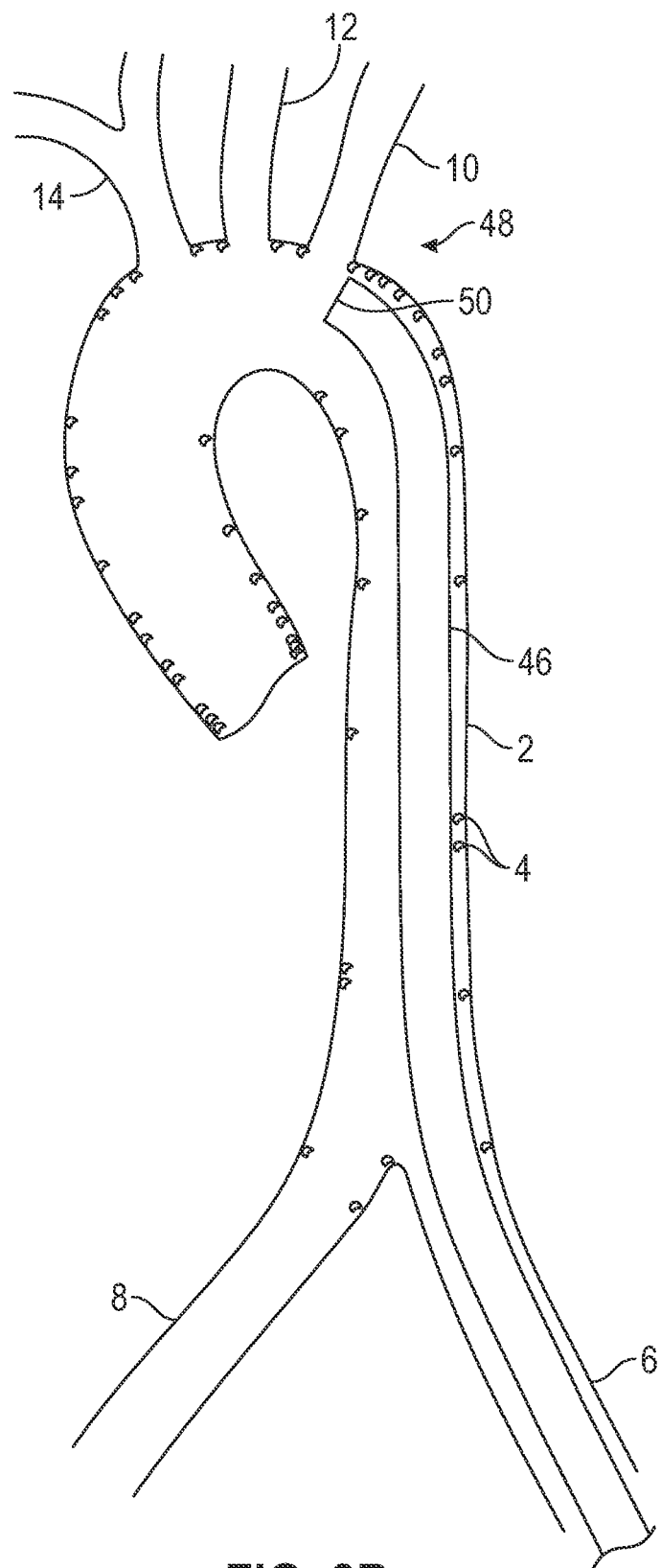

Referring to FIG. 2B, as the instrument (46) is advanced further toward the targeted anatomy, the distal end (50) may present a scraping interface (48) as it is urged past and against the tissue comprising the diseased aorta (2). The scraping action may accidentally and undesirably cause one or more pieces of the deposit material (4) to become loose and thereby flow distally (e.g. downstream, or in the antegrade direction), perhaps into the brain or another undesirable deposit flow location. Further, the scraping dynamic between the distal tip (50) of the instrument (46) and the aortic tissue may result in the formation of one or more embolic masses, which also may find themselves undesirably drifting with the flow path toward the brain or other tissue.

Figure 2C:
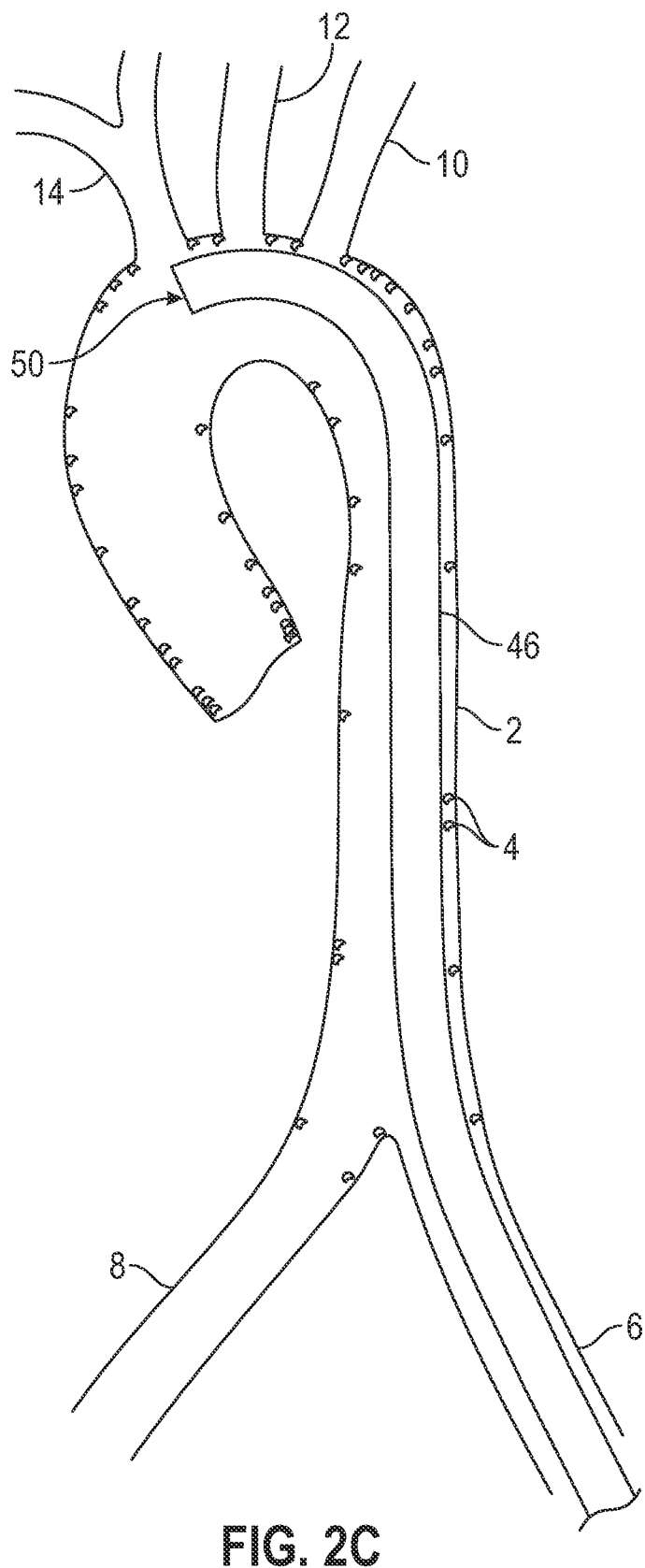

FIG. 2C shows that at the relatively extreme turning portions of the aortic arch, a conventional instrument may find itself located immediately adjacent or within the takeoff junctions of the joining arteries (10, 12, 14), where plaque and other deposits may be particularly mechanically vulnerable.

Figure 2D:
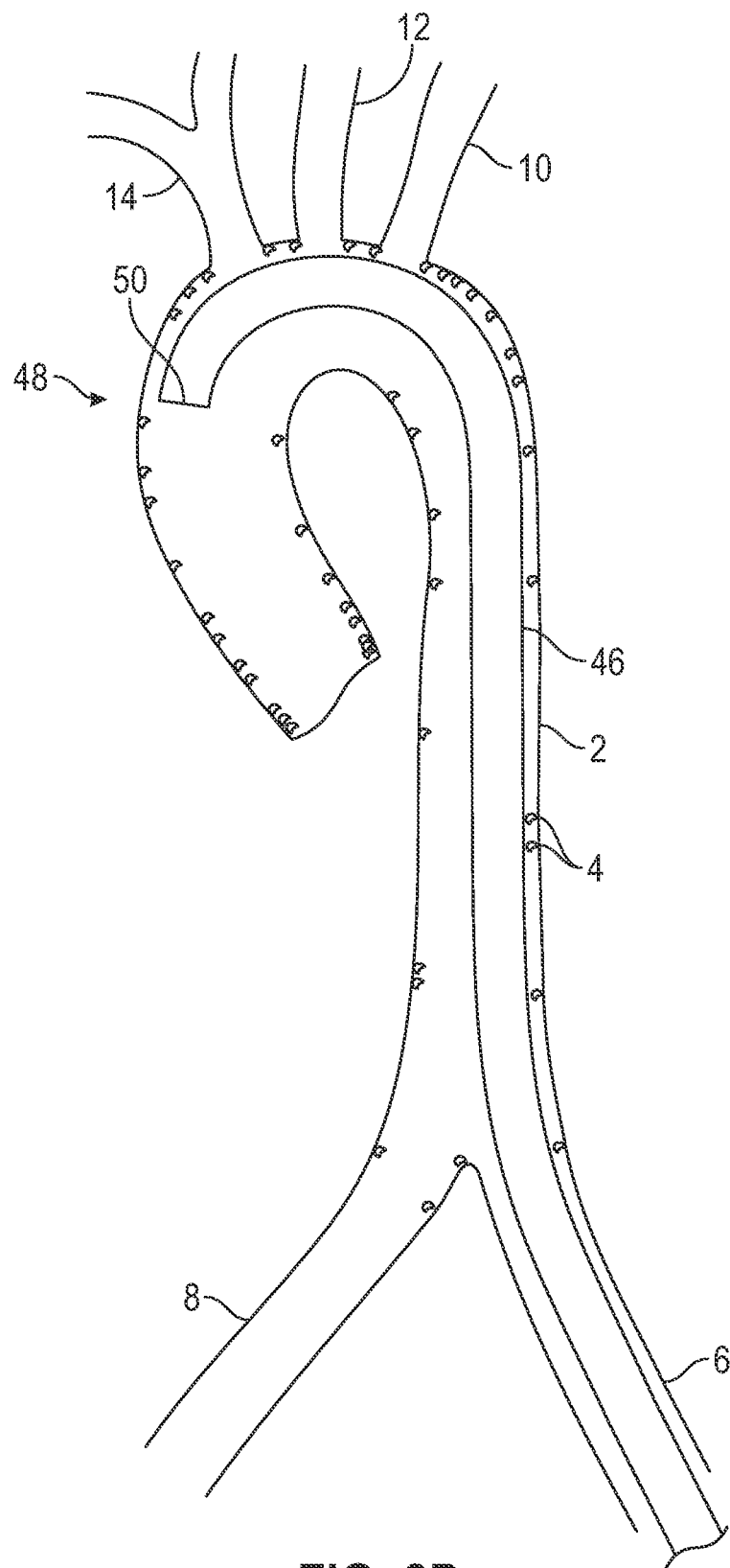
Figure 2E:
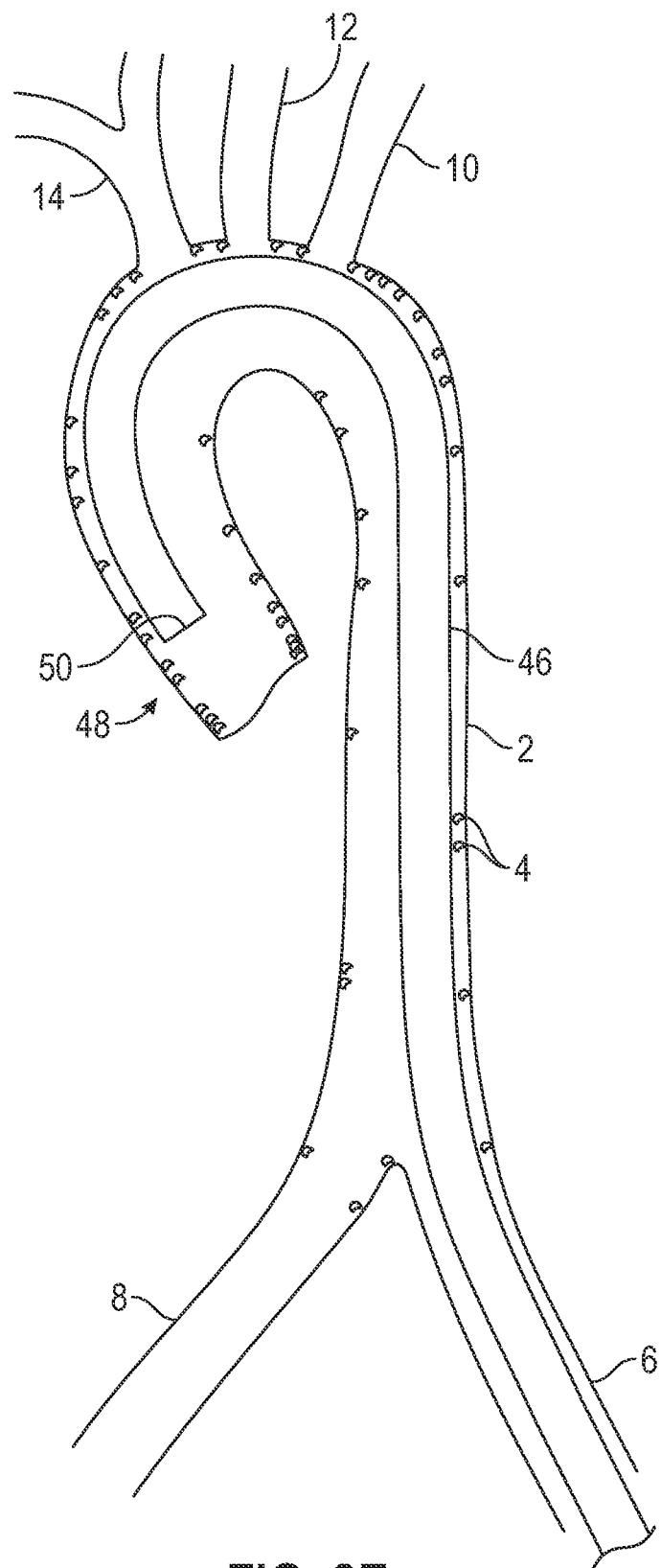
Figure 2F:
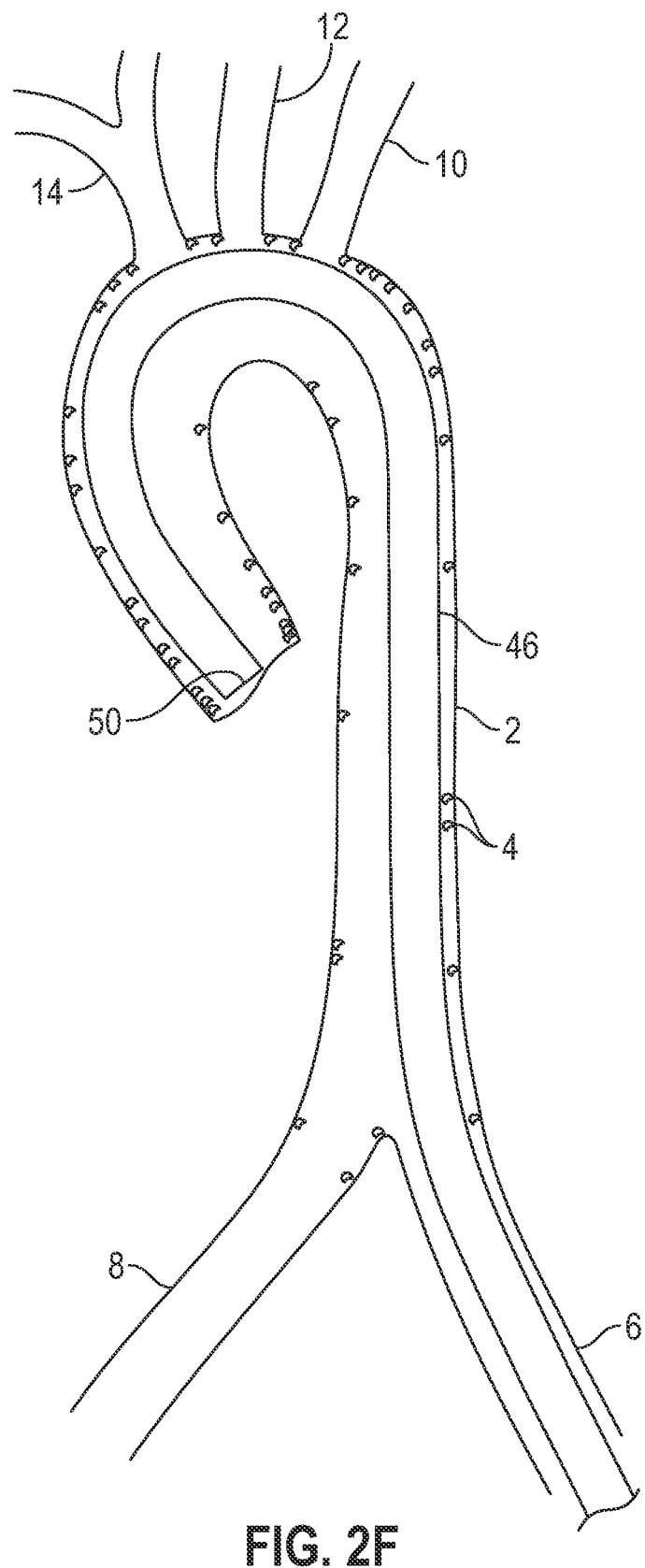

FIGS. 2D-2F illustrate further advancement of the instrument (46) until the distal tip (50) is in the desired location for the planned diagnostic or interventional procedure. Subsequently, the instrumentation is typically retracted, causing yet another scraping interaction as the instrumentation is pulled proximally in a pathway opposite to that described in reference to FIGS. 2A-2F and additional risks for undesirable complication related to such interaction.

Figure 2G:
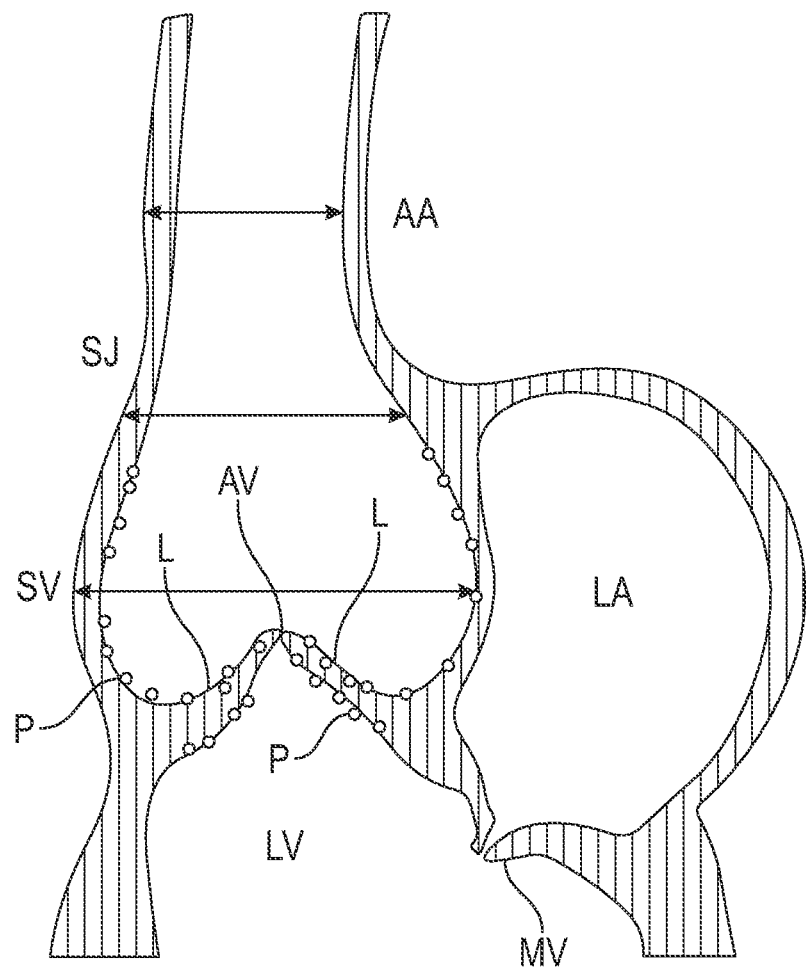
FIG. 2G shows a diseased heart valve.

FIG. 2G shows a native aortic valve AV which illustrates some of the challenges of treating a cardiac valve. Here, the aortic valve AV includes native valve leaflets L which normally appose one another to close the valve during contraction of the left ventricle LV to force blood away from the heart via the ascending aorta AA. The aorta adjacent the aortic valve includes the sinus of Valsalva SV and the sinotubular junction SJ. Blood is directed from the left atrium LA via the mitral valve into the left ventricle LV. The native leaflets and walls of the aorta may be covered or lined with discrete or diffuse plaques P of material such as calcium, lipids, thrombus, or other unwanted materials. When a diagnostic of therapeutic device is advanced through the vasculature toward the aortic valve, the device may scrape or otherwise contact the plaques P and cause the plaques to separate from the tissue and then embolize downstream into other part of the body and cause complications including ischemia, stroke, etc. It would therefore be desirable to provide methods and devices that prevent the unwanted separation of plaques from the native valve, aorta, or other adjacent tissue that could embolize, and in the event that embolization does occur, it would be desirable if such methods and devices capture the emboli and prevent them from flowing downstream. While this example emphasizes the aortic valve, one of skill in the art will appreciate that this is not limiting and the devices and methods disclosed herein may be used in other heart valves such as the mitral or tricuspid valve, or they may be used in other valves of the body including venous valves, or other organs and anatomical structures in the body.

Referring to the accompanying drawings, various aspects of deployment steps and configurations utilizing examples of the present embolic protection system are now described.

Referring to FIG. 3, in some examples, an embolic protection system 300 includes an expandable introducer 400 and an embolic protection device 700. In some examples, the embolic protection system 300 further comprises a peel-away loading sleeve 704 shown fitted to the embolic protection device 700 in the view of FIG. 3. In some examples, the embolic protection system can be deployed to install a therapeutic device such as a replacement prosthetic valve in a human heart. Other uses and applications are possible in a variety of human subjects. In some examples, the expandable introducer 400 and embolic protection device 700 may be supplied and/or used independently of each other as stand-alone medical devices, or replacement parts.

FIGS. 4A-4B show respective side and top pictorial views of an example expandable introducer 400. The expandable introducer 400 includes a mesh sheath (or sleeve) 402 of expandable, porous mesh material. In some examples, the mesh material is expandable in the radial and longitudinal directions of the mesh sheath 402. In some examples, the mesh material is expandable only in the radial direction of the mesh sheath 402. In some examples, the mesh material is expandable only in the longitudinal direction of the mesh sheath. In some examples, the mesh sheath 402 has a usable length of approximately 30 cm to suit an arterial dimension of the human vasculature (see FIGS. 19A-19AD, illustrating a deployment technique, for example). Some examples of this disclosure include a mesh sheath having a usable length in the range 25-35 cm to accommodate variations in vasculature size. In some examples, the mesh sheath 402 has a contracted diameter in the range 3-7 mm and an expanded diameter in the range 7-10 mm.

In some examples, a first region 403 of the mesh sheath 402 is expandable and porous. The first porous region 403 may include mesh material that is expandable in the radial direction only, and may or may not be expandable axially. In some examples, the material properties of the mesh sheath may be selected so that there is no axial expansion or contraction. In other examples, the material properties may be selected so that there is some axial expansion or contraction. In still other examples, the material used may allow some axial expansion or contraction but this is not a significant amount, for example less than 10%, 9%, 8%, 7%, 6%, 5%, 4%, 3%, 2%, or 1% of the total length. In some examples, as the mesh radially expands, the mesh may foreshorten 10 mm or less in the axial direction. Other arrangements are possible. In some examples, the mesh material of the first porous region 403 includes open pores through which fluids may pass (such as blood) while embolic material such as plaque and blood clots are prevented from passing through the mesh sheath 402. In other examples, the mesh may not be utilized to capture embolic material but will still allow blood to pass through the membrane so that blood flow is not disrupted. A suitable mesh material for the first porous region 403 may include polyester, Nylon, or Nitinol mesh. Pore sizes may be provided in the range 70-300 microns to allow blood to pass through the pores while capturing emboli or other particulates. At a distal end of the first porous region 403 of the mesh sheath 402, a marker 405 may be provided. The marker may be radiopaque, echogenic, or visible under other imaging techniques known in the art. The marker 405 may facilitate positioning of the expandable introducer 400 in use (again see FIGS. 19A-19AD, for example).

In some examples, a second region 404 of the mesh sheath 402 is non-expandable and non-porous. The second region may include a non-porous elastomer seal material. The second, non-porous region 404 may include a continuation of the mesh material of the first porous region 403, but the presence of the elastomer seal material renders the second region 404 non-porous and it may be expandable or non-expandable. In the example where it is expandable, it may be substantially non-expandable where any expansion is not significant, e.g. less than 10%, 9%, 8%, 7%, 6%, 5%, 4%, 3%, 2%, or 1%. In any example, the second region may be expandable but less than the first region where the mesh is disposed. The sealed second non-porous region 404 of the mesh sheath 402 does not allow the passage of fluid or embolic material through the walls of the mesh sheath 402. In some examples, the second non-porous region 404 of the mesh sheath 402 has a length of approximately 11 cm. Other lengths are possible to suit different applications and sizes of human vasculature.

Relative to the first porous region 403, the second non-porous region 404 of the mesh sheath 402 may be held in or assume an expanded or partly expanded configuration of the mesh material, as shown. The first porous region 403 and the second non-porous region 404 of the mesh sheath 402 may taper down in a distal direction along their lengths as shown to facilitate advancement of the expandable introducer 400 into the human vasculature.

With reference again to FIGS. 4A-4B, the expandable introducer 400 further comprises an introducer hub 406 that includes a hemostasis valve 424 (visible in FIGS. 6A-6B). The introducer hub 406 is connected to a flushing three-way stopcock 408. An interior volume of the introducer hub 406 inside the seal of the hemostasis valve and including the mesh sheath 402 (including the first porous region 403 and the second non-porous region 404) may be flushed using the three-way stopcock 408. An example flushing operation is described further below with reference to FIGS. 18A-18P.

The expandable introducer 400 further comprises a sheath dilator 410 for obturating the mesh sheath 402 or providing a removable dilating tip for insertion into the body. The sheath dilator 410 can be locked in place within the mesh sheath 402 of the expandable introducer 400 by a manually removable clip 412. The clip 412 engages with the introducer hub 406 and can be removed by an operator to allow the sheath dilator 410 to advance or retract through the expandable introducer 400 in use. At a proximal end of the sheath dilator 410, a dilator Luer fitting 414 is provided. The dilator Luer fitting 414 can be manipulated by an operator to advance or retract the sheath dilator 410 once the clip 412 is released, as well as allowing releasable fluid coupling with additional tubing, syringes, pumps, etc. At an opposite distal end of the sheath dilator 410, a sheath dilator tip 416 is provided. The tip is soft and tapered to facilitate entry into the body and also to provide an atraumatic tip during distal advancement through the vessel.

In a loaded configuration of the sheath dilator 410, seen more clearly in FIG. 5A, the sheath dilator tip 416 extends past and sits as a cap over a thus-constrained open end 418 of the mesh sheath 402. As described more fully below, the expandable introducer 400 may be advanced into the human vasculature in the loaded configuration and then deployed once in position. In a deployed configuration of the expandable introducer 400, seen more clearly in FIG. 5B, the sheath dilator 410 has been advanced through the mesh sheath 402 to expand the sheath and push the sheath dilator tip 416 off the constrained open end 418 of the mesh sheath 402. This release of the sheath dilator tip 416 allows the now-uncapped open end 418 of the mesh sheath 402 to enlarge in size. The enlarged open end 418 of the mesh sheath 402 is larger than the outer diameter of the sheath dilator tip 416. As a result, the sheath dilator 410 is free to be retracted by an operator to withdraw the sheath dilator tip 416 back through the enlarged open end 418 of the mesh sheath 402 and extract the sheath dilator 410 and the sheath dilator tip 416 from the expandable introducer 400 as a whole leaving the sheath open and expanded.

Reference is now made to FIGS. 6A-6B which show respective sectional and enlarged part-sectional views of the expandable introducer 400, and to FIG. 4C, which shows a pictorial view of the sheath dilator 410. The dilator Luer fitting 414 of the sheath dilator 410 is connected to the sheath dilator tip 416 of the sheath dilator 410 by a thin, flexible tube 420 of resilient polymer material. The tube 420 may have apertures formed along its length (not visible) allowing the sheath dilator 410 to be flushed by means of a flushing connector 415 provided on the dilator Luer fitting 414 (see FIG. 18B of this connection in operation, for example). In some examples, the tube 420 travels the entire length of the distance between the dilator Luer fitting 414 and the sheath dilator tip 416. Other configurations are possible. In FIG. 5A, a distal end 432 of the tube 420 may be seen connected to the sheath dilator tip 416. Thus, the flushing connector 415 also allows the sheath dilator tip 416 to be flushed by fluid passing through the entire length of the lumen of the tube 420 to exit at the sheath dilator tip 416. Axial or rotational movement on the dilator Luer fitting 414 is imparted directly to the sheath dilator tip 416 by the tube 420.

With reference to FIG. 4C and FIG. 6B in particular, along at least part of its length, the tube 420 is carried inside a metallic tube 422. The metallic tube 422 passes through and seals with the hemostasis valve 424 located inside the introducer hub 406, as shown. At a proximal end of the metallic tube 422, a detent formation 426 is provided to engage with the clip 412 when locked. A distal end of the metallic tube 422 is connected to a second polymer tube 428. The second polymer tube 428 extends from its connection at the metallic tube 422 through the second non-porous region 404 and the first porous region 403 of the mesh sheath 402 to a distal end 434 (visible in FIG. 5A) of the second polymer tube 428 inside the sheath dilator tip 416. The second polymer tube 428 may include along its length different sections of varying diameter or shape, for example as shown by the tapered and/or thinner sections 436A-436C in FIG. 4C. The tube 420 passes through a continuous lumen defined by the interconnected metallic and plastic tubes 422 and 428.

Figure 7:
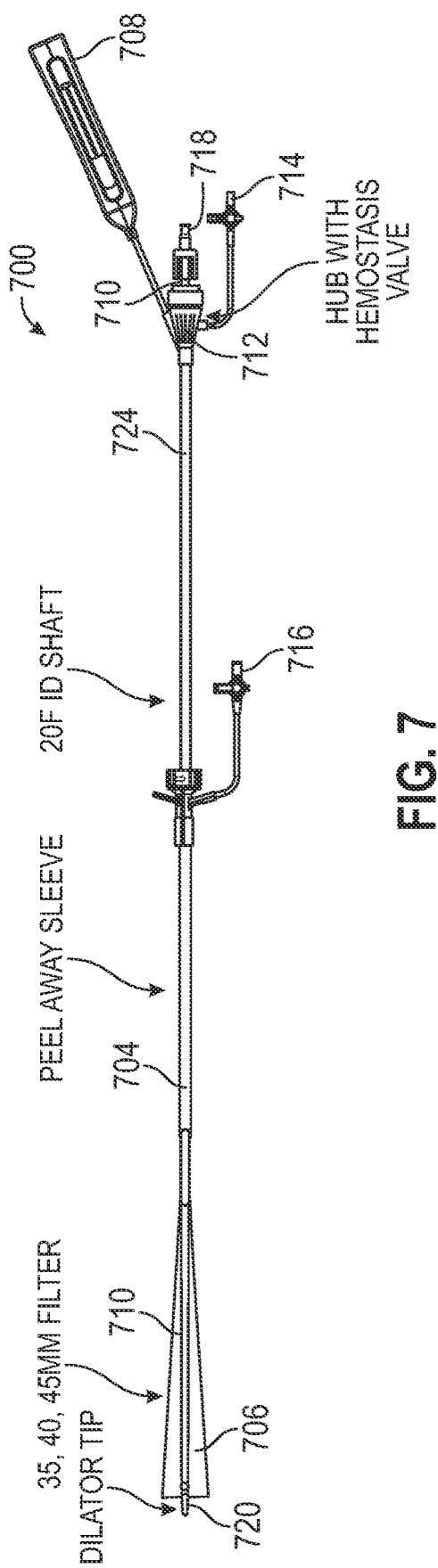
FIG. 7 shows pictorial views of an embolic protection device, with a peel-away loading sleeve and filter dilator fitted thereto, according to example embodiments.

Reference is now made to FIG. 7 of the accompanying drawings which shows a pictorial view of an embolic protection device 700, according to an example of the present disclosure. In some examples, such as in the illustrated example, the embolic protection device 700 is provided as a component of an embolic protection system 300. Examples of an embolic protection system 300 may include an embolic protection device 700 that includes a catheter shaft 724, a filter 706 provided at a distal end of the catheter shaft 724, a filter actuator 708 located at or towards a proximal end of the embolic protection device 700, and a filter dilater (or catheter obturator) 710 insertable inside a main lumen of the embolic protection device 700 or catheter shaft 724. Some examples may include a peel-away loading sleeve 704 mountable to an outside of the embolic protection device 700 to assist in loading the embolic protection device 700 into an artery of the human vasculature. In some examples, each of these components may be provided or used separately, or provided and used in combination, for example as part a kit.

As shown further in FIG. 7, the embolic protection device 700 comprises a catheter hub 712 that includes an internal hemostasis valve connected to a three-way flushing stopcock 714. A usable length of the embolic protection device between the catheter hub 712 and the distal end of the filter 706 is approximately 85 cm but may be shorter or longer, as required. The installed filter dilater 710 includes a snap-lock Luer fitting 718 disposed at a proximal end of the filter dilater 710, and (at its distal end) a filter dilator tip (or nosecone) 720 seen extending just past the distal end of the filter 706. The loading sleeve 704 includes a flushing three-way stopcock 716.

Figure 8A:
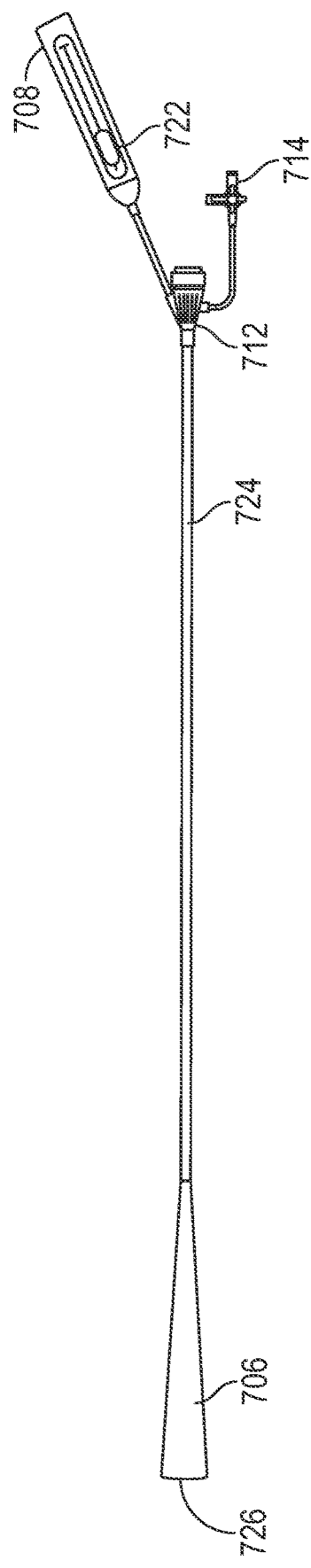
FIGS. 8A-8B show respective side and top pictorial views of an embolic protection catheter without a peel-away loading sleeve and filter dilator fitted to it.
Figure 8B:
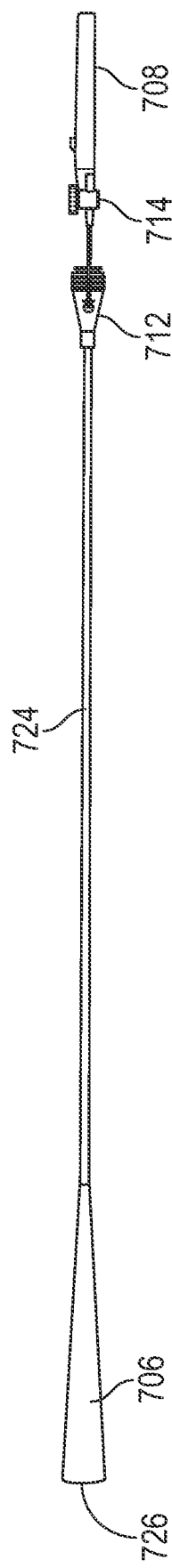

FIGS. 8A-8B show respective side and top pictorial views of the embolic protection device 700 without the loading sleeve 704 and filter dilator 710 fitted to it. The embolic protection device 700 is shown with the filter 706 in an open or expanded configuration. The filter 706 is opened and closed by manipulation of a slider 722 on the filter actuator 708, as described more fully below. In some examples, the embolic protection device 700 includes a 20F internal diameter (ID) catheter shaft 724 of flexible polymer material. A suitable material for the catheter shaft 724 may include any materials known in the art such as polyethylene, polypropylene, a fluorinated polymer, polyurethane, etc.

The catheter shaft 724 includes a main lumen through which the filter dilator 710 may be advanced or retracted to assist in deploying, repositioning, or withdrawing the filter 706 in use of the embolic protection device 700. The catheter shaft 724 also includes one or more subsidiary lumens that carry actuation wires or other devices. One such actuation wire 734 (best seen in FIG. 10C), described further below, is connected to and extends from the slider 722 to a hoop wire 752 (see e.g. FIG. 10A) provided around an openable and closable mouth 726 of the filter 706. Other actuation wires or tensile members are possible.

Figure 9A:
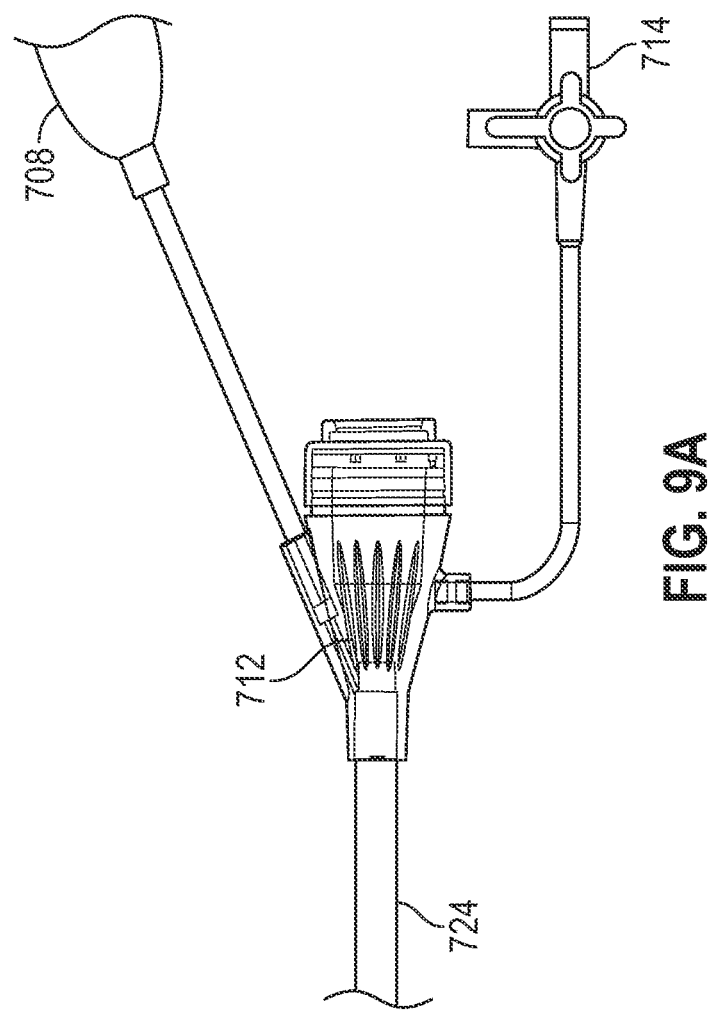
FIGS. 9A-9B show part sectional views of a catheter hub provided on the proximal end of an embolic protection catheter, according to example embodiments.
Figure 9B:
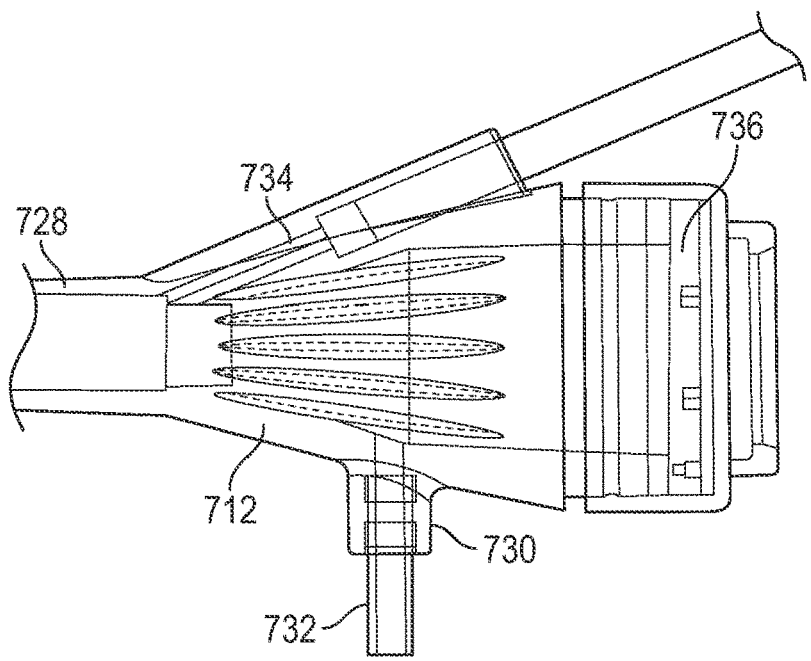

FIGS. 9A-9B show part sectional views of the catheter hub 712 provided on the proximal end of the embolic protection device 700. In FIG. 9B, the catheter hub 712 is seen to include a connector 728 for receiving the proximal end of the catheter shaft 724 and a connector 730 for receiving a flushing line 732 leading to the three-way flushing stopcock 714. A part of the actuation wire 734 is visible in a subsidiary lumen of the catheter shaft 724 extending between the slider 722 on the filter actuator 708 and the filter 706. The catheter hub 712 further comprises a hemostasis valve 736 that serves to seal and guide the filter dilator 710 into the catheter shaft 724 in the distal direction in the view (e.g. towards the left side of FIG. 9B).

Figure 10A:
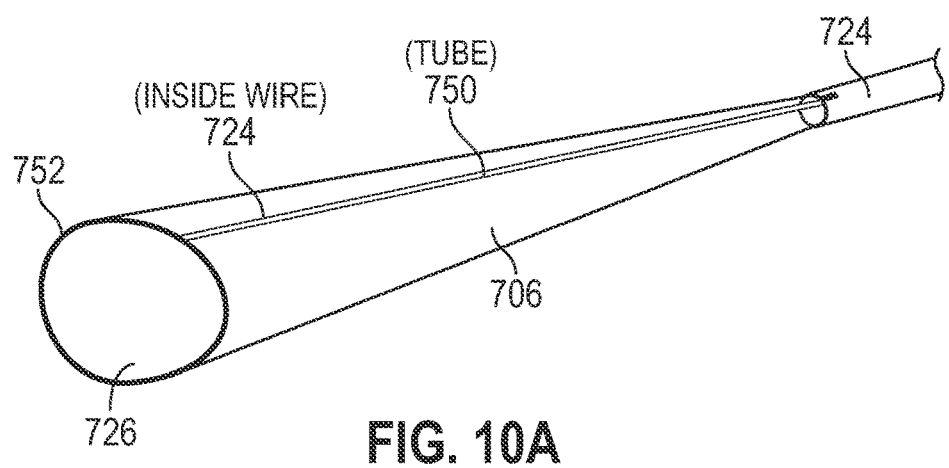
FIGS. 10A-10C include pictorial and sectional views of a filter provided on a distal end of an embolic protection catheter, according to example embodiments.
Figure 10B:
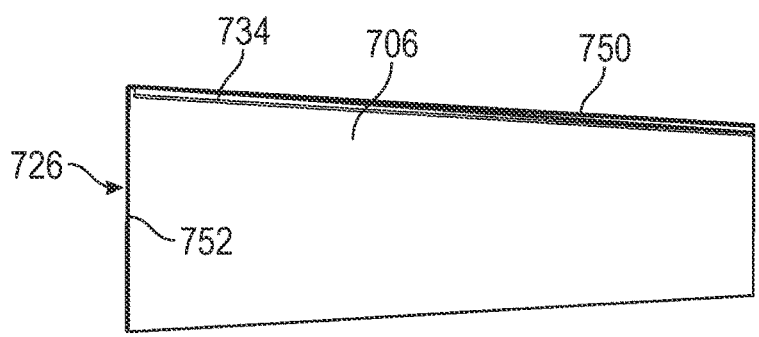
Figure 10C:
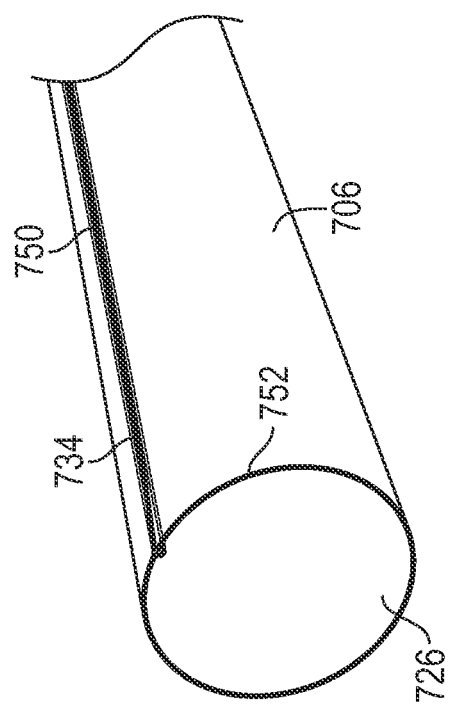

FIGS. 10A-10C include pictorial and sectional views of the filter 706 provided on the distal end of the embolic protection device 700. In these views, the filter 706 is shown in an open or expanded configuration. In some examples, the filter 706 is provided as a closable basket or net. The filter includes a mesh or net material to capture (when open) and retain (when closed) embolic and other waste materials, such as plaque flakes and blood clots. The filter may have a porosity that permits blood or other fluids to pass through the filter while retaining the embolic or other materials. Polyester, Nylon, Nitinol or other materials may be used for the filter material. In some examples, the filter 706 includes a frustoconical shape when flat, substantially as shown. Other shapes and configurations of the filter 706 are possible. In some examples, a shape or configuration of the filter 706 allows it to assume an elongate tubular or snake like form when collapsed, for example when the filter mouth 726 is closed, or when the filter 706 is being repositioned or withdrawn from a site, for example. Examples in this regard may be seen in FIGS. 19A-19AD discussed further below.

As mentioned above, the filter 706 can be opened and closed by an operator manipulating the slider 722 of the filter actuator 708. When manipulated, movement of the slider 722 serves to apply tension to or relieve tension from the actuation wire 734 to which it is connected. Corresponding movement of the actuation wire 734 in turn opens and closes the filter 706, as desired. In the illustrated example, the filter 706 is supported in the embolic protection device 700 by a thin, tubular rail (or arm) 750. The tubular rail 750 is mounted to the distal end of the catheter shaft 724, for example as shown in FIG. 10A.

The tubular rail 750 carries the actuation wire 734 that extends, in a subsidiary lumen of the catheter shaft 724, from the slider 722 of the filter actuator 708 to the location of the filter 706. At its distal end, the actuation wire 734 is connected to a hoop wire 752. When the slider is pushed forward towards the location of the filter 706, the hoop wire 752 expands and defines, under action and control of the actuation wire 734, an open mouth 726 of the filter 706, as shown. In this position, the filter 706 is open. The mouth 726 of the filter 706 is resizable and closable by manual operation of the slider 722, as needed. Retracting the slider pulls the actuation wire proximally which applies a tension to the hoop collapsing it and correspondingly collapsing the filter.

In some examples, the hoop wire 752 is formed integrally as an extension of the actuation wire 734. In some examples, the hoop wire 752 is formed as a separate hoop. The mouth 726 of the filter 706 may include, or be attached to, self-expanding members to bias the mouth 726 to an open configuration. In some examples, the mouth 726 of the filter 706 may include, or be attached to, self-contracting members to bias the mouth to a closed configuration. In some examples, the self-expanding or self-contracting members may cooperate to entrap a closed mouth of the filter in a circumferential groove or channel 744 on the distal end of the filter dilator 710 described further below with reference to FIGS. 13-14, for example.

Figure 11A:
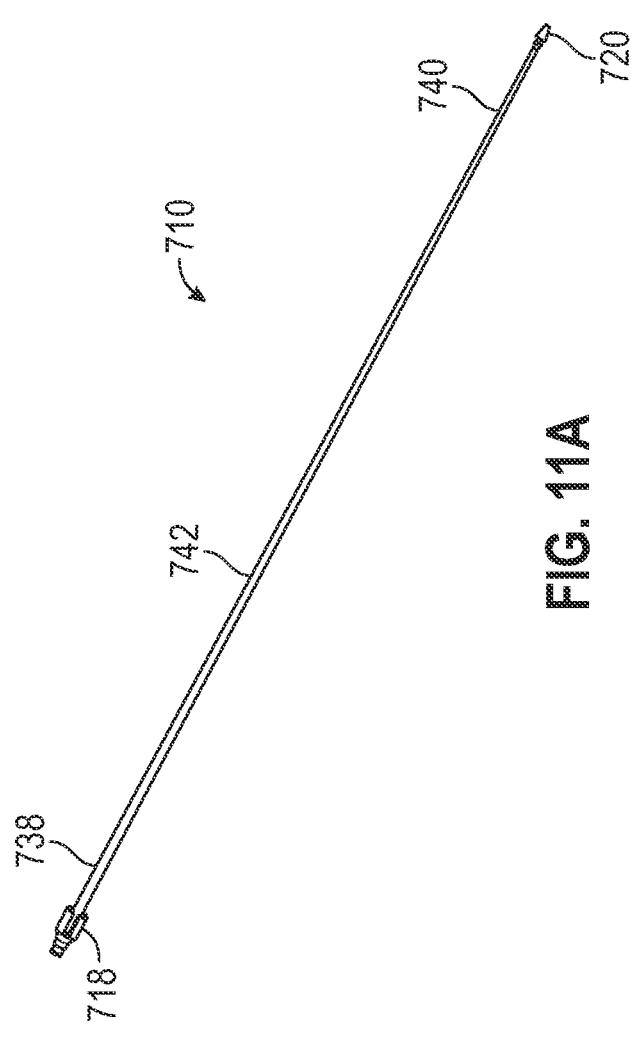
FIGS. 11A-11B show pictorial views of a filter dilator, according to an example embodiment.
Figure 11B:
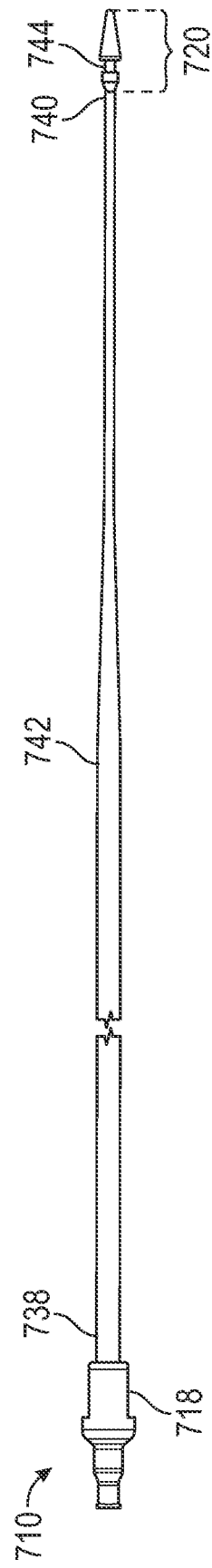

FIGS. 11A-11B show pictorial views of an example filter dilator 710, with some of parts of the filter dilator shown in enlarged view in FIG. 11B. Sectional views of the filter dilator 710 are provided in FIGS. 12A-12B.

As mentioned above, the filter dilator 710 includes a snap-lock Luer fitting 718 provided at a proximal end 738 of the dilator, and a filter dilator tip 720 provided at a distal end 740 of the filter dilator 710. The filter dilator 710 includes a flexible shaft 742 comprised of polymers known in the art (e.g. polyethylene, polypropylene, ABS, PVC, FEP, combinations thereof, etc.). The flexible shaft 742 has an outer diameter sized to pass through the hemostasis valve 736 of the catheter hub 712 and pass through the main lumen of the catheter shaft 724 in a sliding manner.

Figure 13:
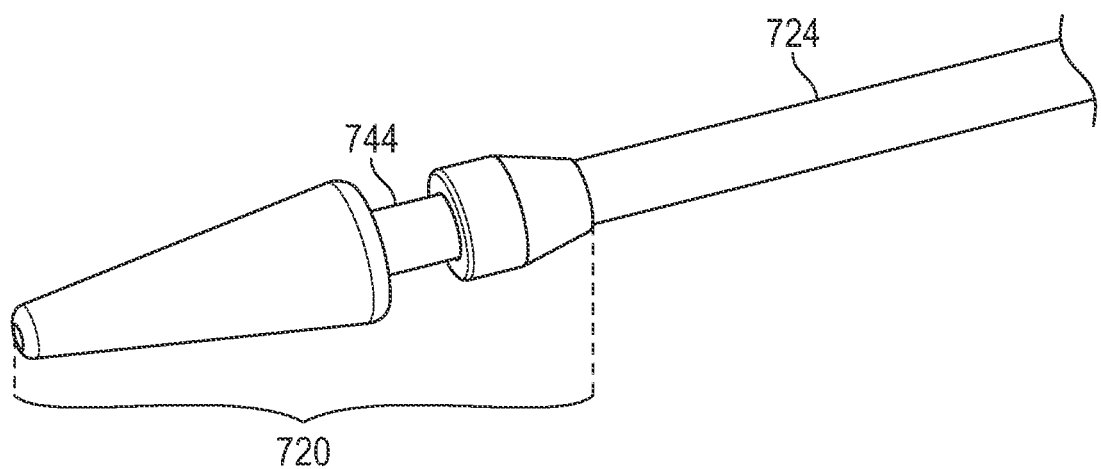
FIG. 13 shows a pictorial view of an atraumatic distal tip of a filter dilator, according to an example embodiment.
Figure 14:
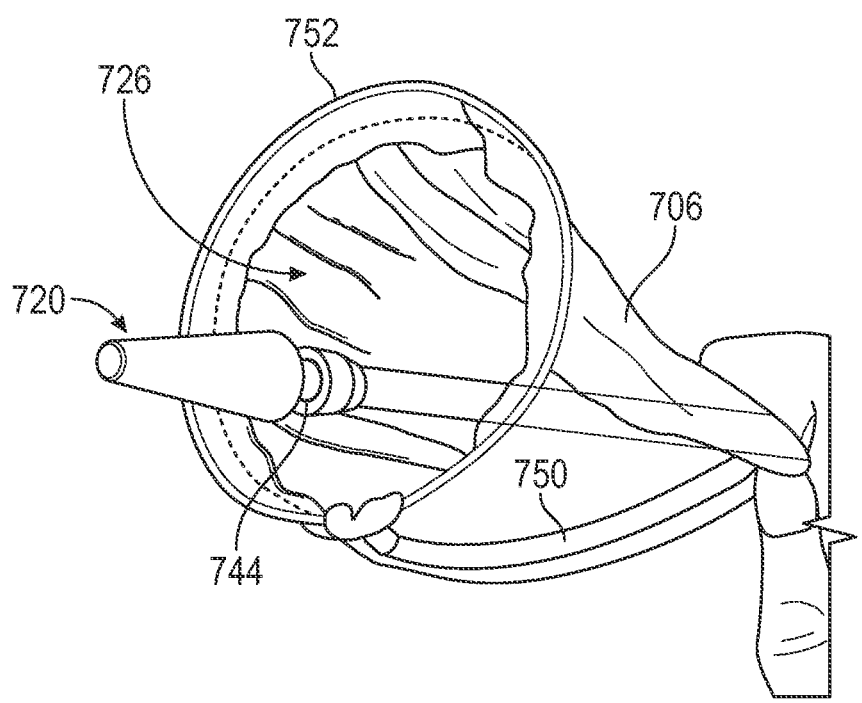
FIGS. 14-15 show pictorial views of open and closed configurations of a filter, according to an example embodiment.

With reference in particular to FIG. 13, the filter dilator tip 720 of the filter dilator 710 is coupled to shaft 724 and includes a circumferential channel 744 (or other formation) that can engage with and retain the hoop and mouth 726 of the filter 706 when the filter is closed. Pictorial views of open and closed configurations of the filter 706 are shown in FIGS. 14-15, respectively.

Figure 15:
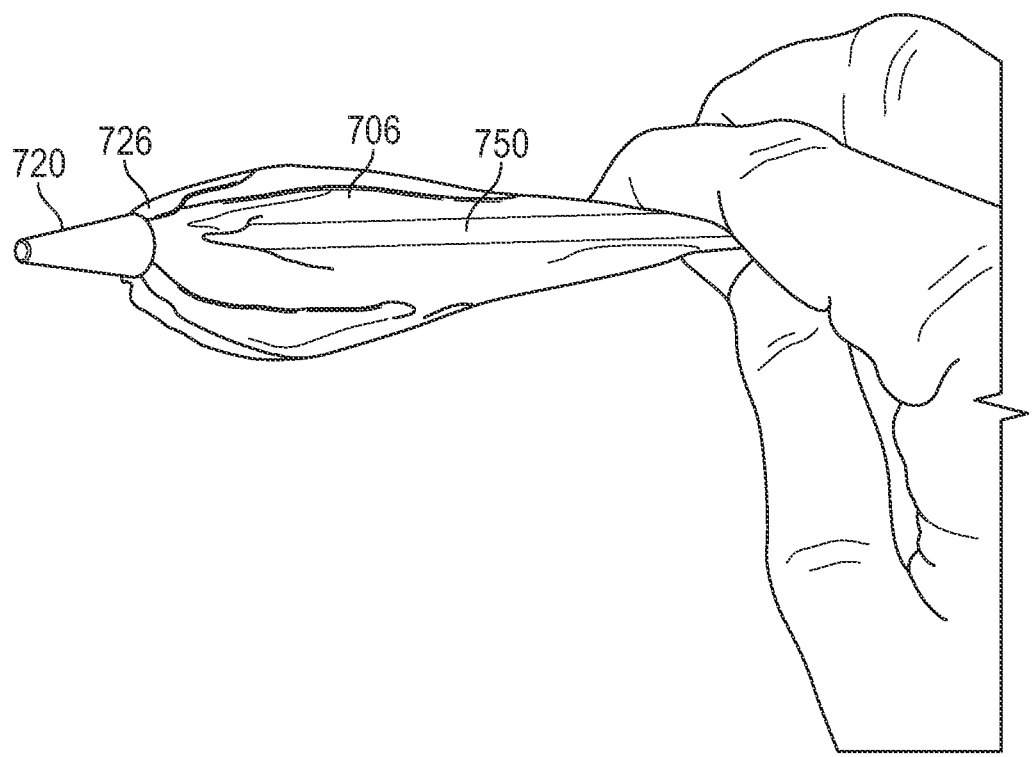
Figure 16A:
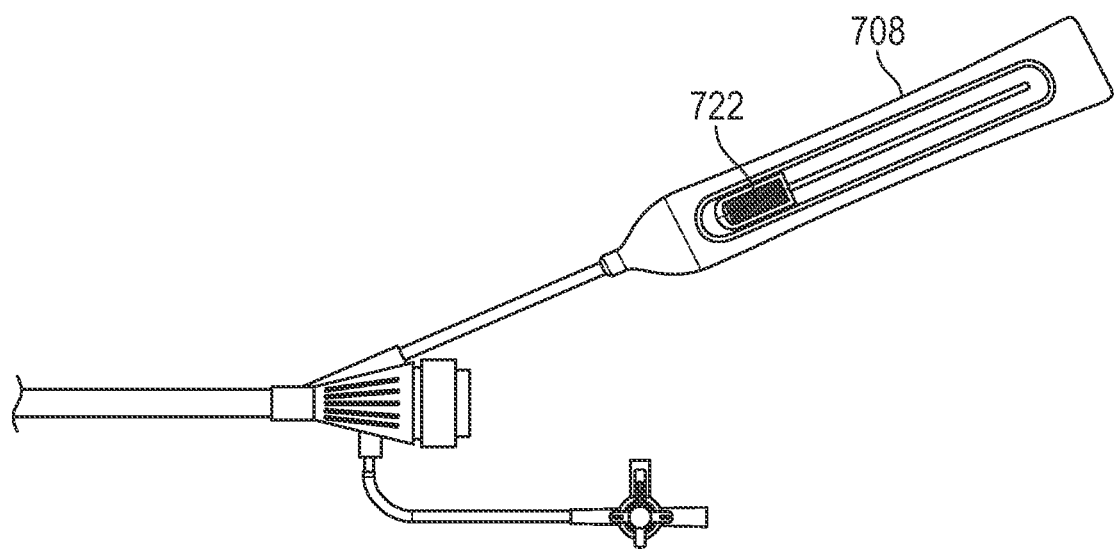
Figure 16B:
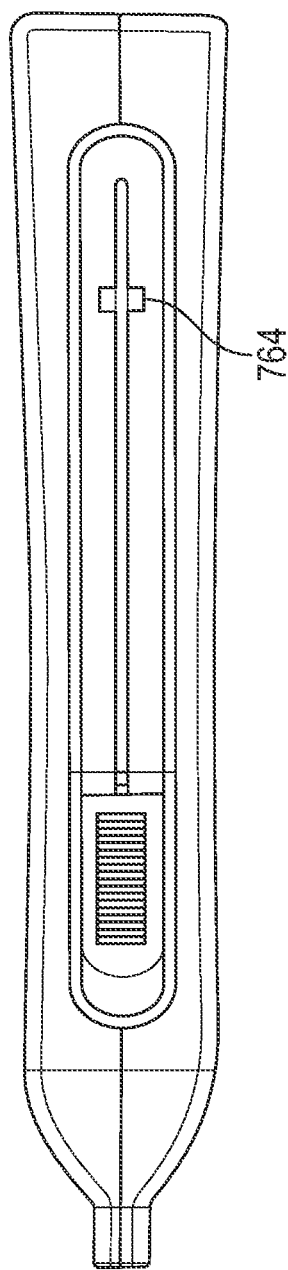
Figure 16C:
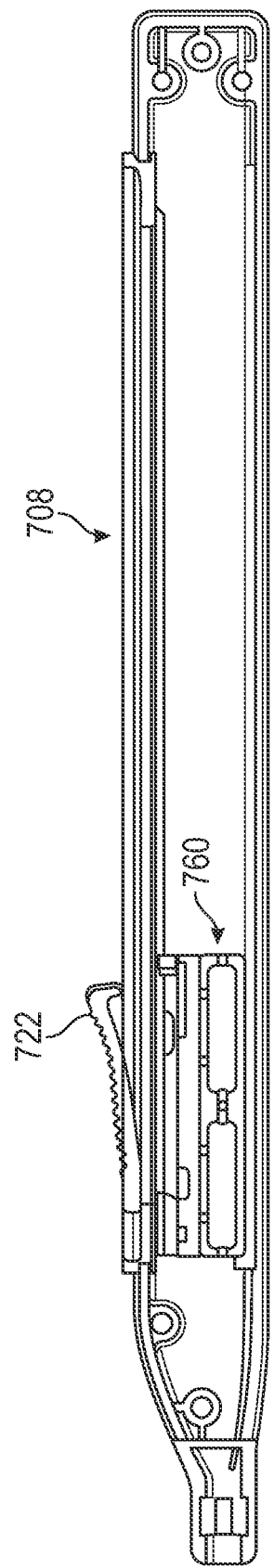
Figure 17A:
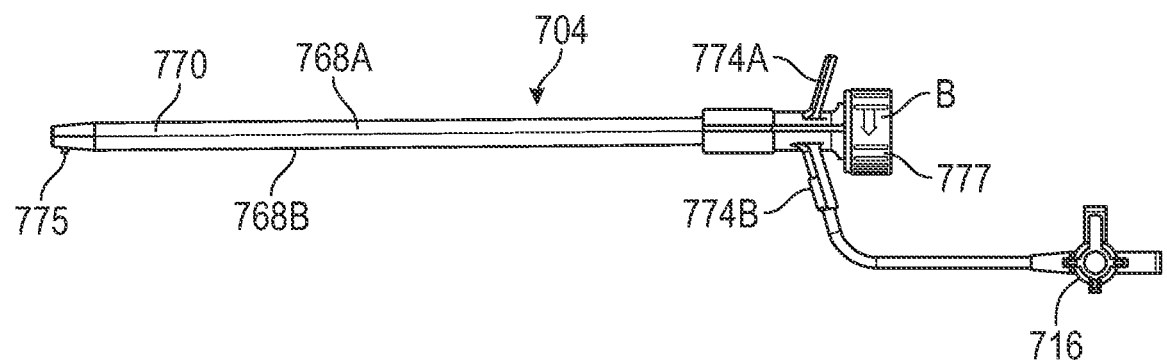
FIGS. 17A-17D show pictorial and sectional views of a peel-away loading sleeve, according to an example embodiment.
Figure 17B:
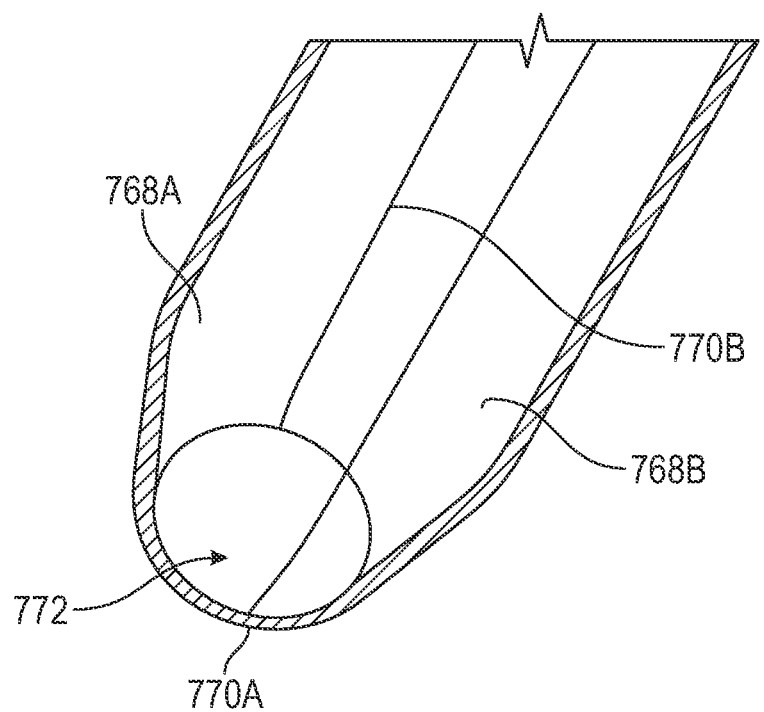
Figure 17C:
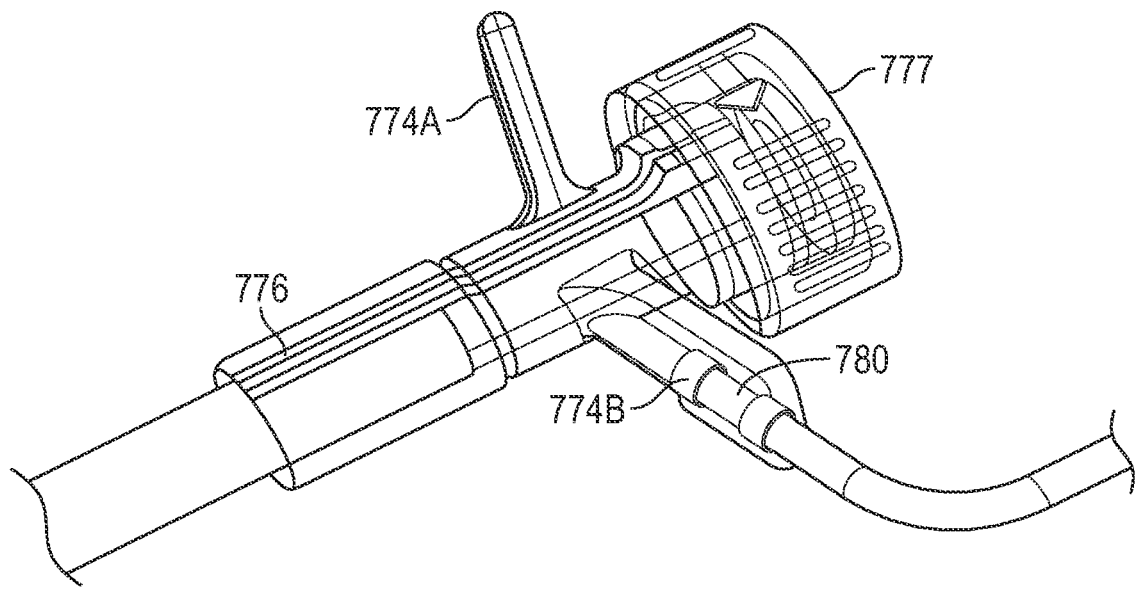
Figure 17D:
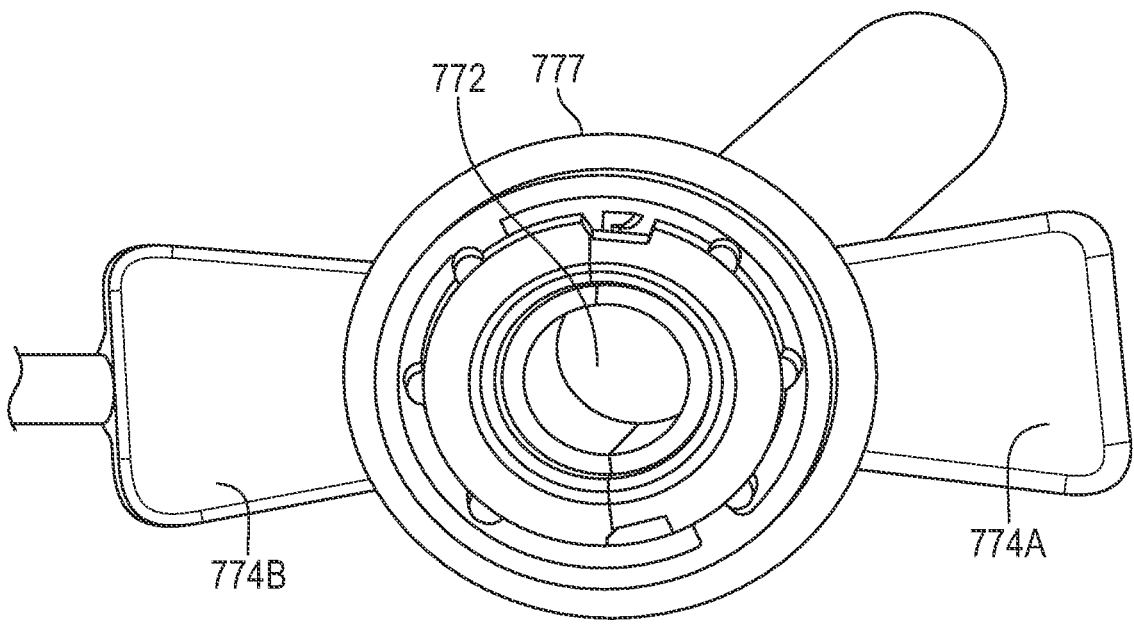

In FIG. 15, under a pulling action of the slider 722 away from the filter 706, the closed mouth 726 of the filter 706 can be captured and retained within the circumferential channel 744 of the filter dilator tip 720 under locking tension in the hoop and actuation wires 752 and 734, respectively. The locking tension in the hoop and actuation wires 752 and 734 can be maintained by engaging a slider locking mechanism 760 of the filter actuator 708 shown in the various views of FIGS. 16A-16E. The device may include the thin, tubular rail (or arm) 750 previously described above. A movable detent 762 in the slider locking mechanism can be locked into one or more locking recesses 764 and 766 of the slider to hold the filter 706 in a closed configuration while the embolic protection device 700 is deployed, repositioned, or withdrawn from the site of a medical procedure, for example. A downward push on the slider 722 causes the detent 762 to release. The closed mouth 726 of the filter 706 can be securely held in the circumferential channel 744 of the filter dilator 710 and supported axially along its length to prevent collapse when the filter 706 is advanced into the human vasculature and through the confines of the expandable introducer 400.

Reference is now made to FIG. 17A-17D of the accompanying drawings which include pictorial and sectional views of the loading sleeve 704 of the embolic protection device 700 illustrated in FIG. 7. The loading sleeve 704 is of tubular shape defined by two separable parts 768A and 768B, each semi-circular in cross section and joined along frangible parting lines 770A and 700B. The 768A and 768B together define a tip 775 and a lumen 772 of the loading sleeve 704 into which the embolic protection device 700 can be inserted and readied for use. The removable parts 768A and 768B can be split apart and peeled away from the embolic protection device 700 by manipulating two separation handles 774A and 774B. In the illustrated example, the handle 774B includes a flushing line 780 in fluid communication with the three-way stopcock 716 and the lumen of 772 of the loading sleeve 704.

As shown, the separation handles 774A and 774B are joined to each other by two parting lines 776 which are coincident with the parting lines 770A and 770B. Movement of the separation handles 774A and 774B to initiate removal of the loading sleeve 704 can be unlocked by rotating a locking cap 777 that retains the two halves together and prevents inadvertent separation. Removal of the locking cap 777 from the loading sleeve 704 allows the separation handles 774A and 774B to be twisted by an operator and split apart along the parting lines (which may be perforated or have a frangible parting line), thus allowing subsequent splitting apart and removal of the parts 768A and 768B to release the loading sleeve completely from the embolic protection device 700.

Figure 18A:
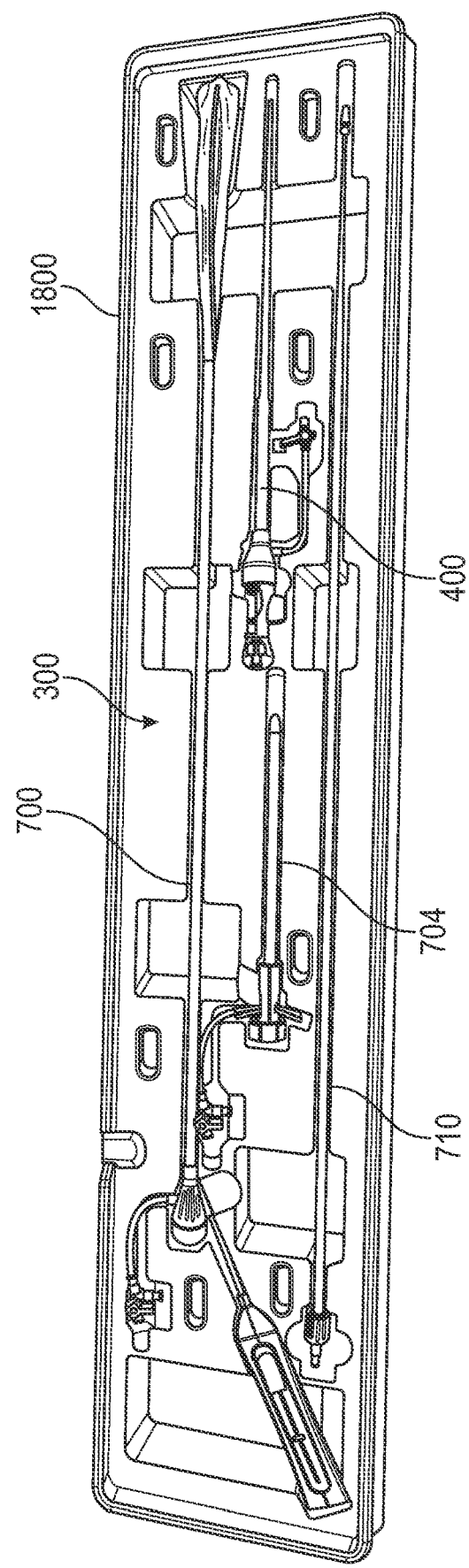
FIGS. 18A-18P show various aspects of a preparation technique for an embolic protection system, in accordance with the present disclosure
Figure 18B:
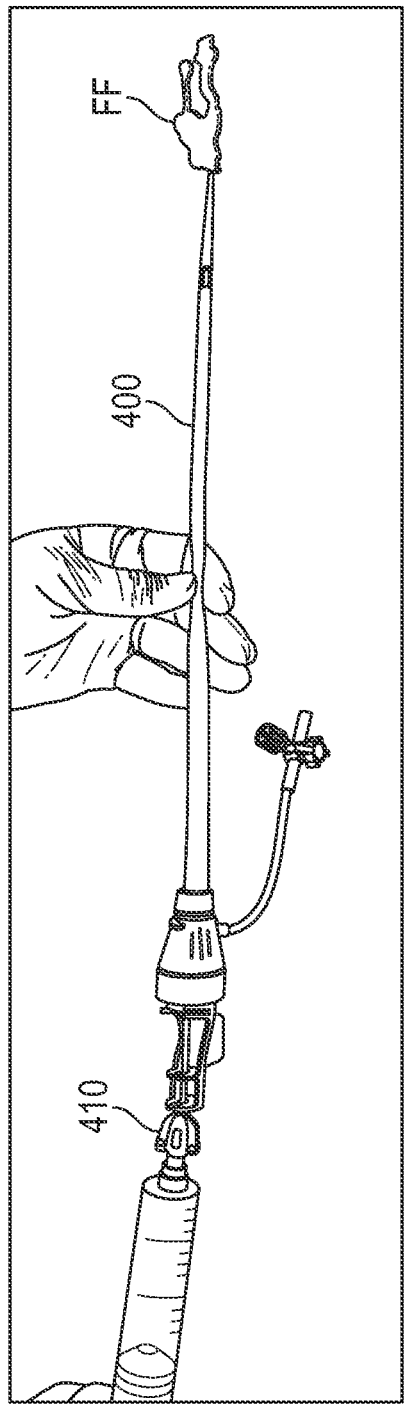
Figure 18C:
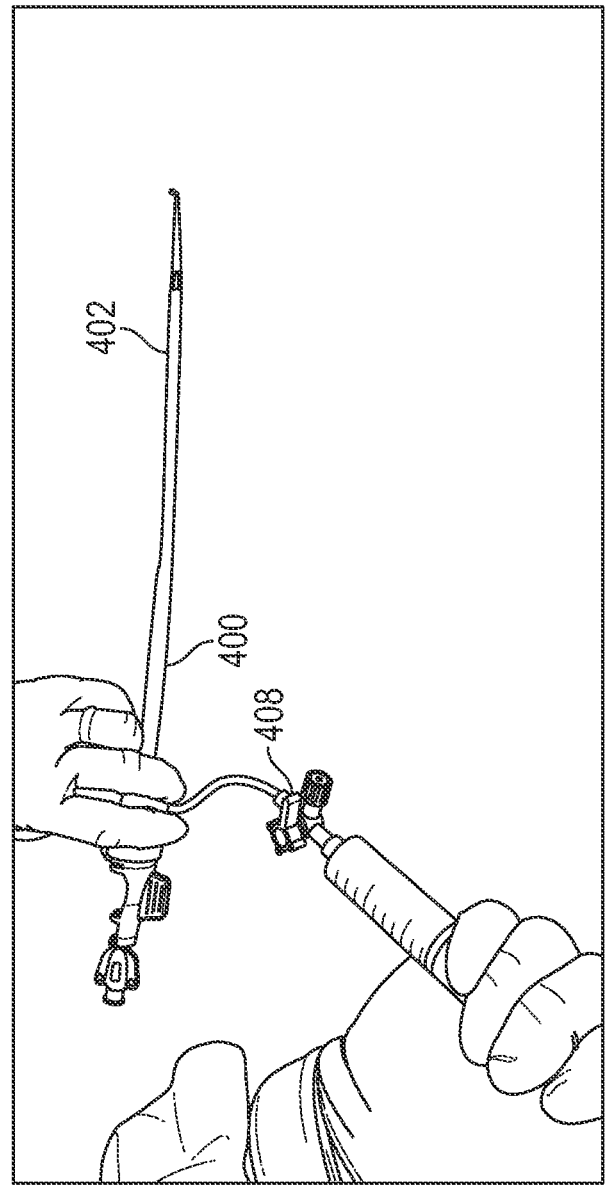
Figure 18D:
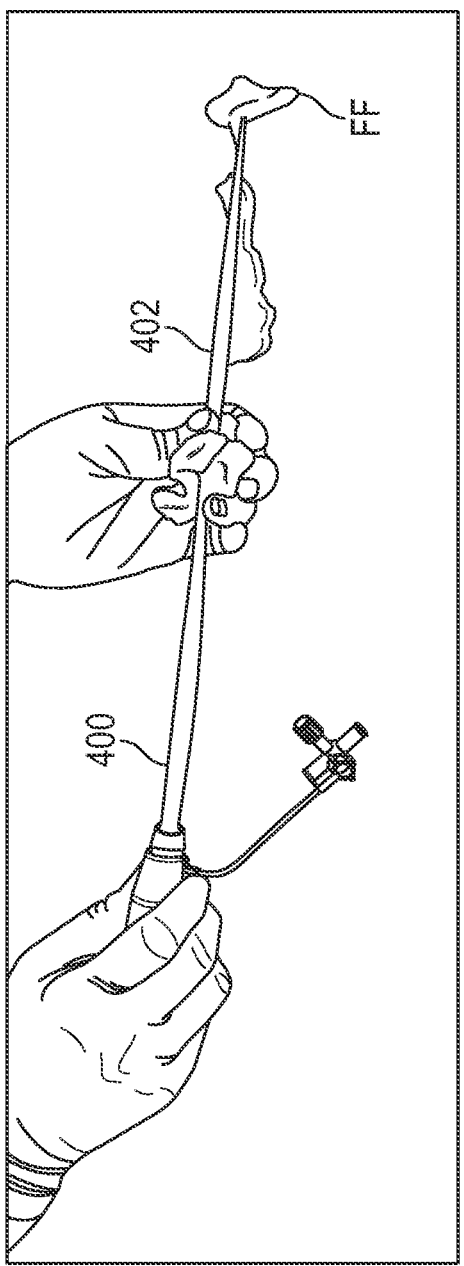
Figure 18E:
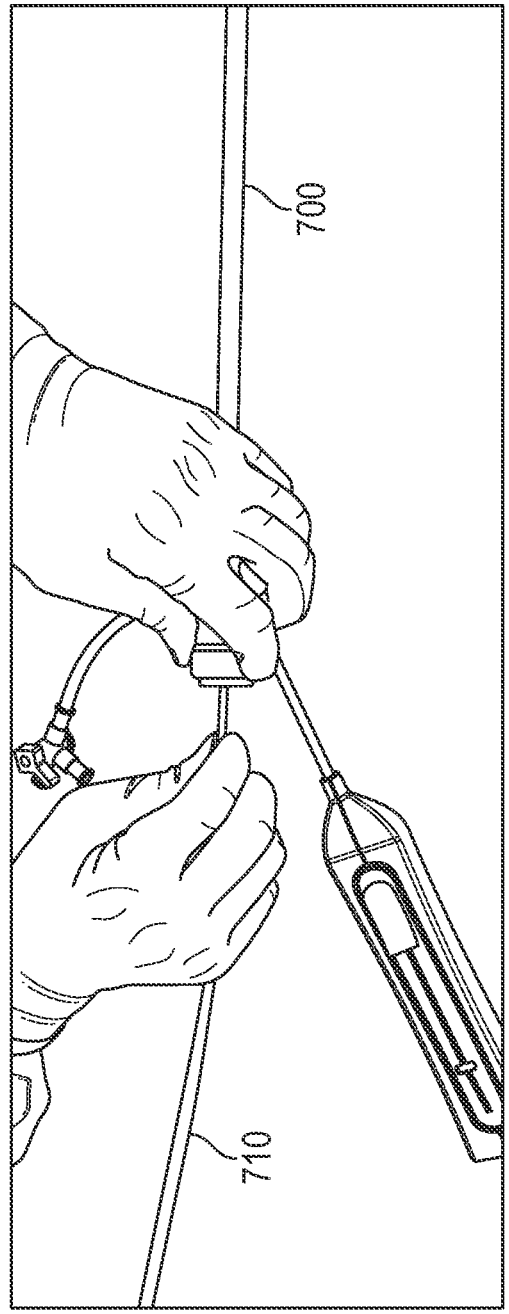
Figure 18F:
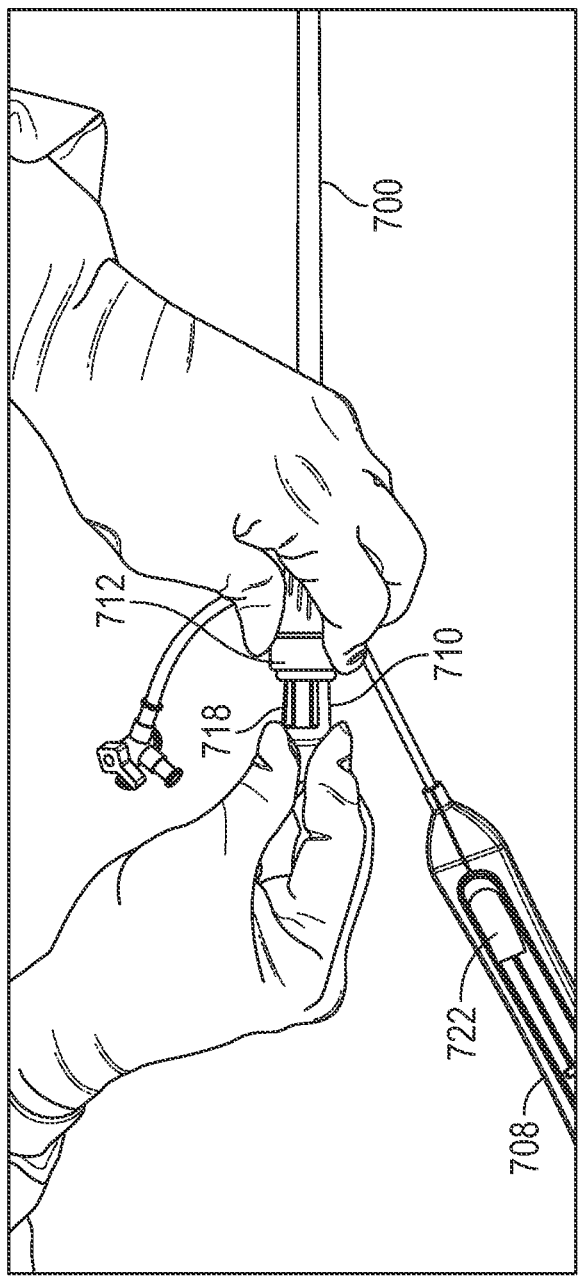
Figure 18G:
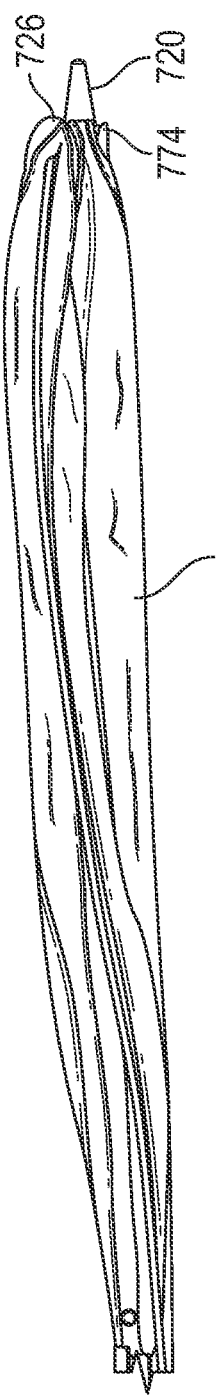
Figure 18H:
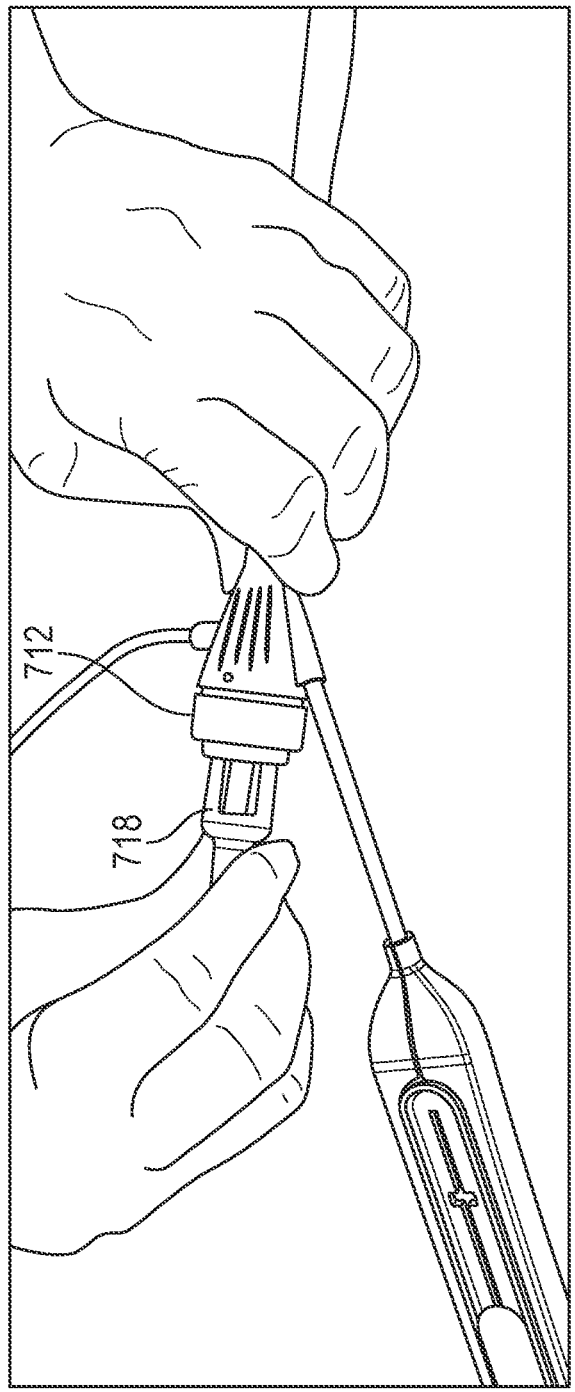
Figure 18I:
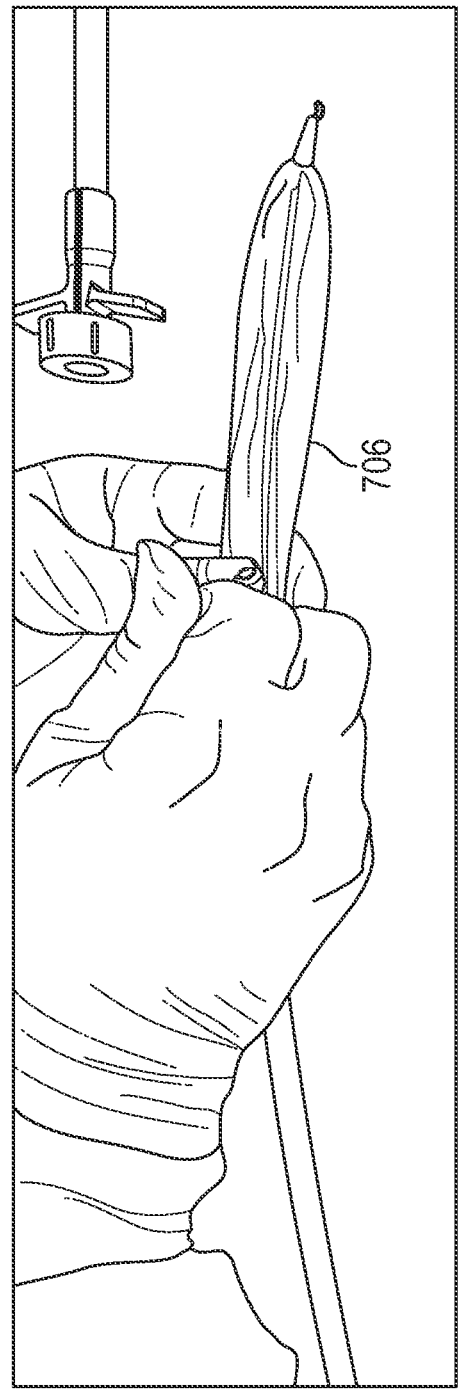
Figure 18J:
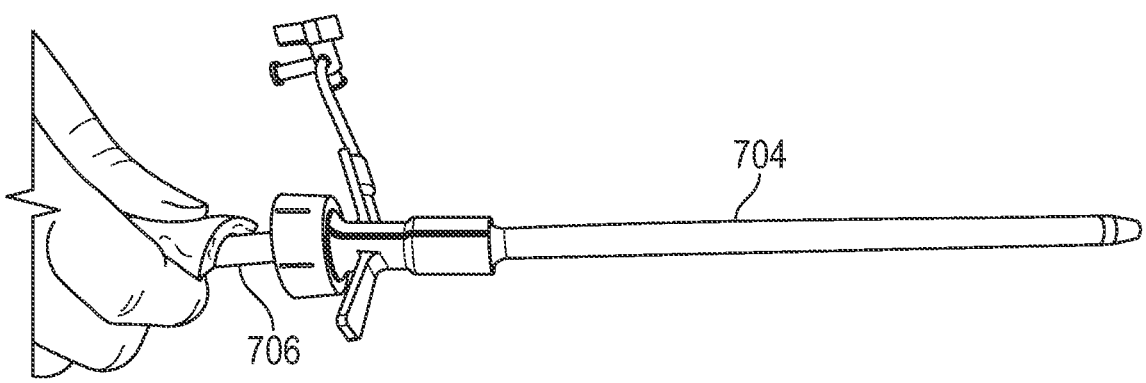
Figure 18K:
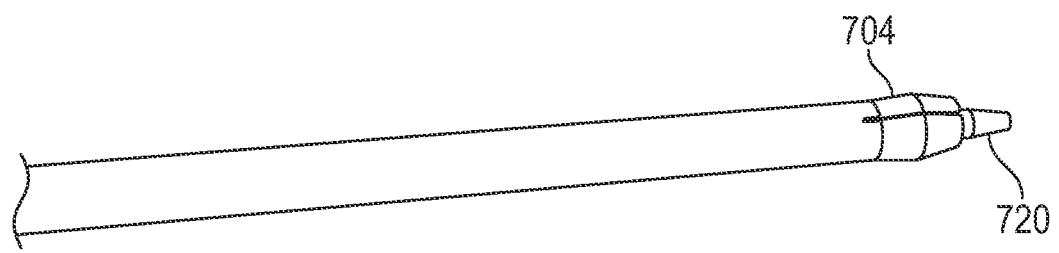
Figure 18L:
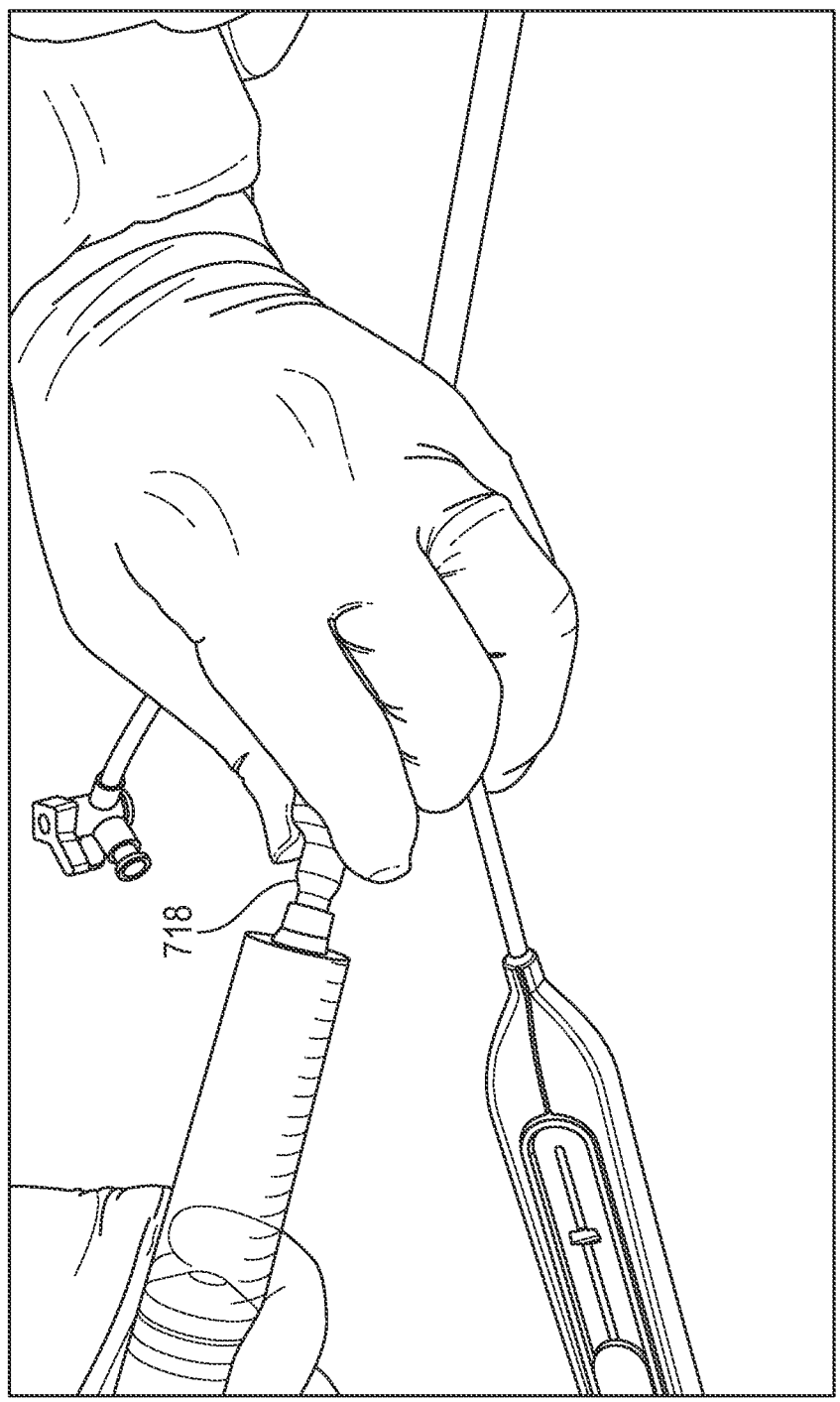
Figure 18M:
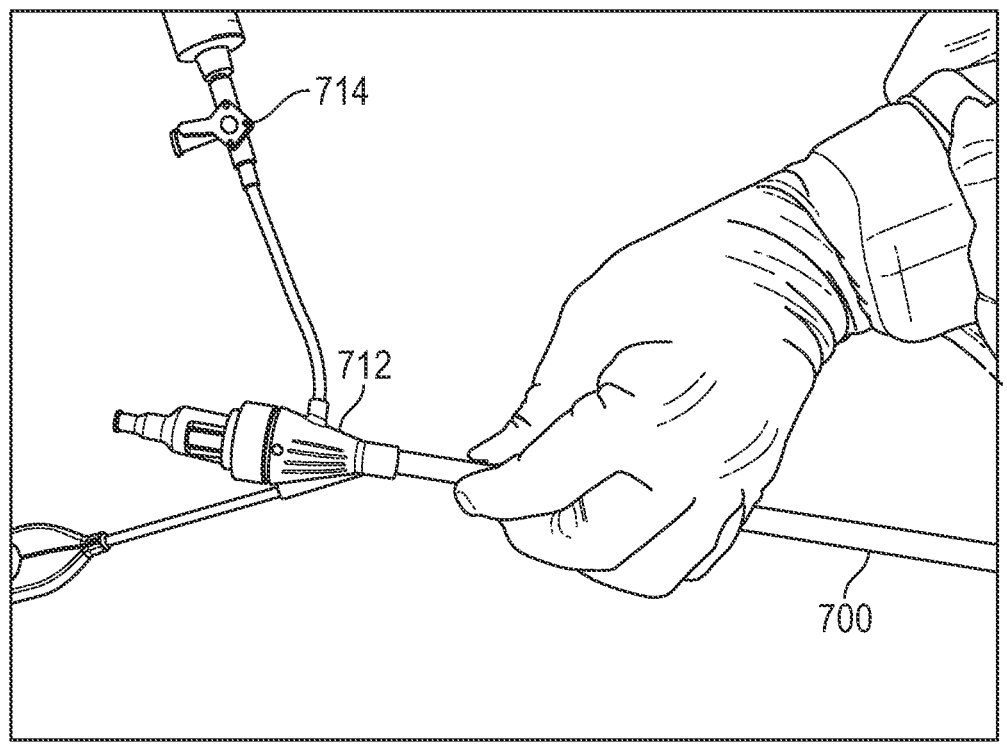
Figure 18N:
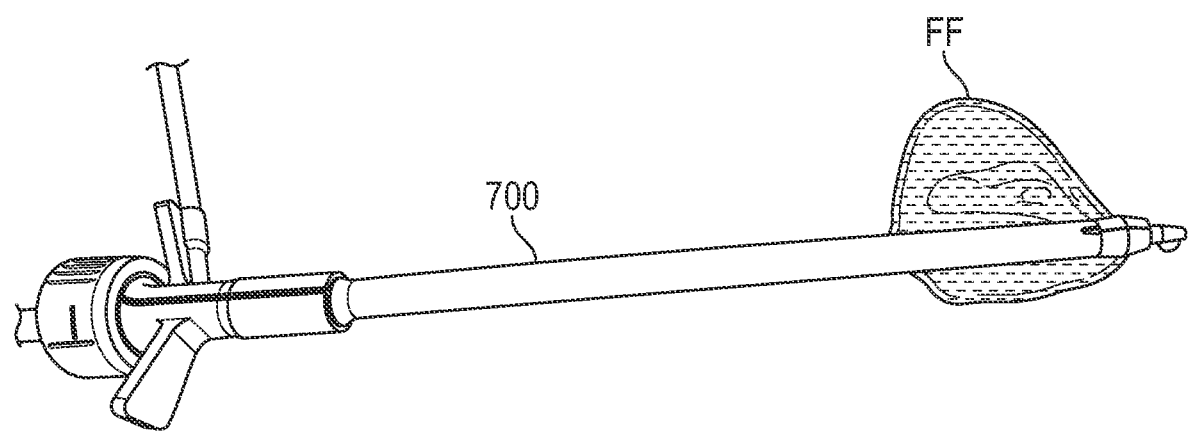
Figure 18O:
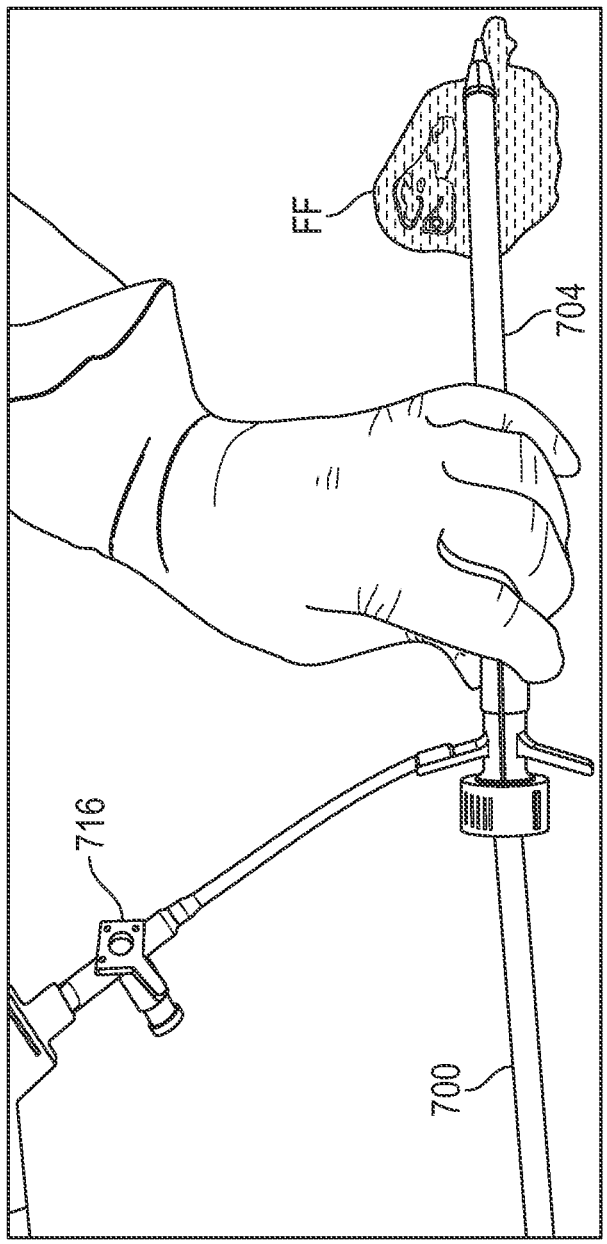
Figure 18P:
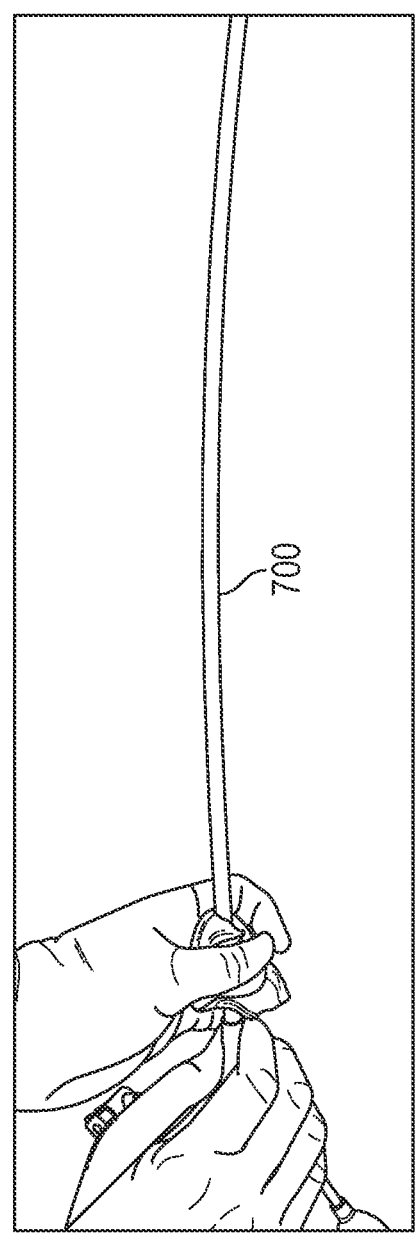

With reference to FIGS. 18A-18P, preparation of an embolic protection system 300 for use in a medical procedure may be performed as follows in some examples. In the illustrated example, the embolic protection system 300 is provided in a sealed tray 1800 as a kit of parts.

In FIG. 18A, a lid of the tray 1800 has been removed allowing access to the expandable introducer 400 and other components such as the embolic protection device 700, the loading sleeve 704, and the filter dilator 710.

In FIG. 18B, the sheath dilator 410 of the expandable introducer 400 is flushed with saline or another flushing fluid FF from a syringe.

In FIG. 18C, the mesh sheath 402 portion of expandable introducer 400 is flushed using the three-way stopcock 408, again using fluid such as saline from a syringe.

In FIG. 18D, the mesh sheath 402 is wetted with a flushing fluid FF such as saline to activate a hydrophilic coating for increased lubricity. This may be accomplished by wiping a wet sponge over an outer surface of the device.

In FIG. 18E, the filter dilator 710 is inserted into the embolic protection device 700.

In FIG. 18F, insertion of the filter dilator 710 is continued until the dilator Luer fitting 718 contacts the catheter hub 712, but is not snapped in.

In FIG. 18G, the slider 722 of the filter actuator 708 (best seen in FIG. 18F) is manipulated to close the filter 706, ensuring the closed mouth 726 of the filter 706 is engaged in the circumferential channel 774 of the filter dilator tip 720, and the slider 722 is locked in the closed position.

In FIG. 18H, the dilator Luer fitting 718 is locked into onto the catheter hub 712 by snapping it in.

In FIG. 18I, the filter 706 is wetted by wiping a sponge soaked with fluid over the filter or irrigating the filter with a fluid stream. The fluid may be saline or another fluid.

In FIG. 18J, the loading sleeve 704 is fitted by sliding it over the filter 706.

In FIG. 18K, the sliding continues until the loading sleeve 704 tip aligns with the filter dilator tip 720, as shown.

In FIG. 18L, the inserted filter dilator is flushed with fluid from the locked in Luer fitting 718. A syringe may be used to flush with saline or another fluid.

In FIG. 18M, the embolic protection device 700 is flushed from the three-way flushing stopcock 714 connected to the catheter hub 712. A syringe may be used to flush with saline or another fluid.

FIG. 18N shows that flushing with flushing removes air from the device and ensures that flushing fluid FF is exiting the distal end of the embolic protection device 700.

In FIG. 18O, the loading sleeve 704 is flushed from the three-way stopcock 716 again ensuring (as is visible in FIG. 18O) that flushing fluid FF exits the distal end of the embolic protection device 700 so air is evacuated from the device. Saline or another fluid may be introduced with a syringe.

In FIG. 18P, the embolic protection device 700 is wetted to activate a hydrophilic coating for increased lubricity. Again, a fluid soaked sponge may be wiped along the device. The fluid may be saline or another fluid.

Figure 19A:
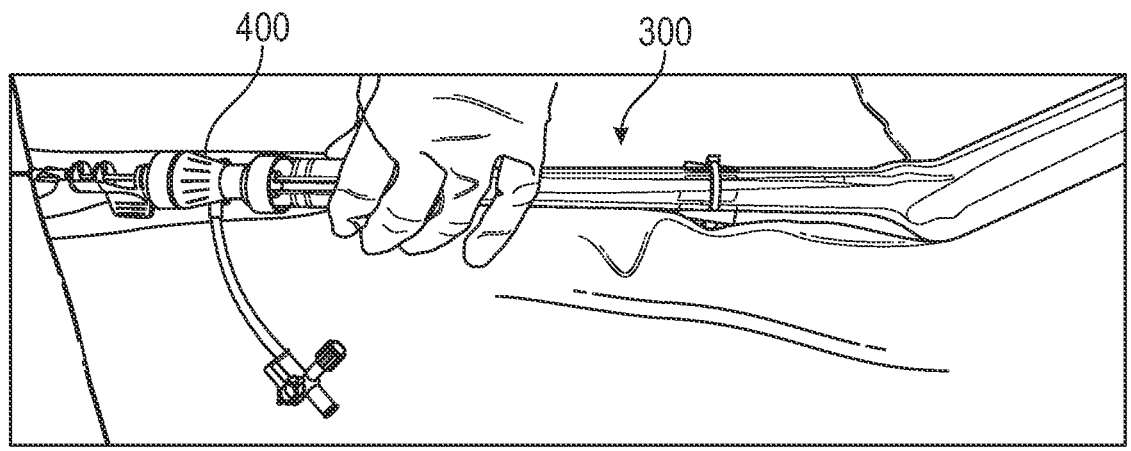
FIGS. 19A-19X show various aspects of a deployment technique, in accordance with the present disclosure.
Figure 19B:
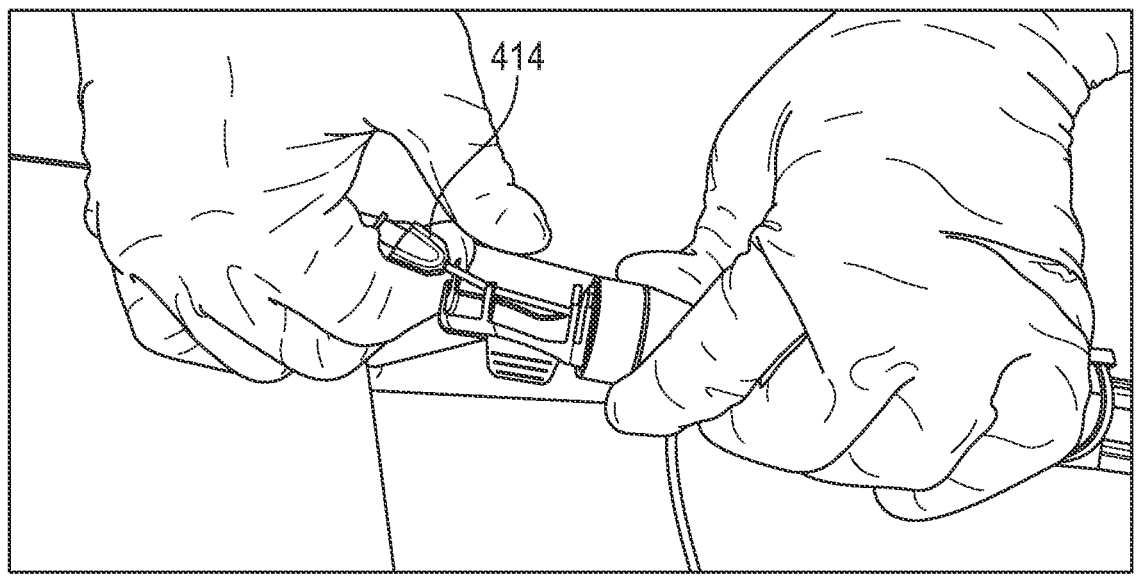
Figure 19C:
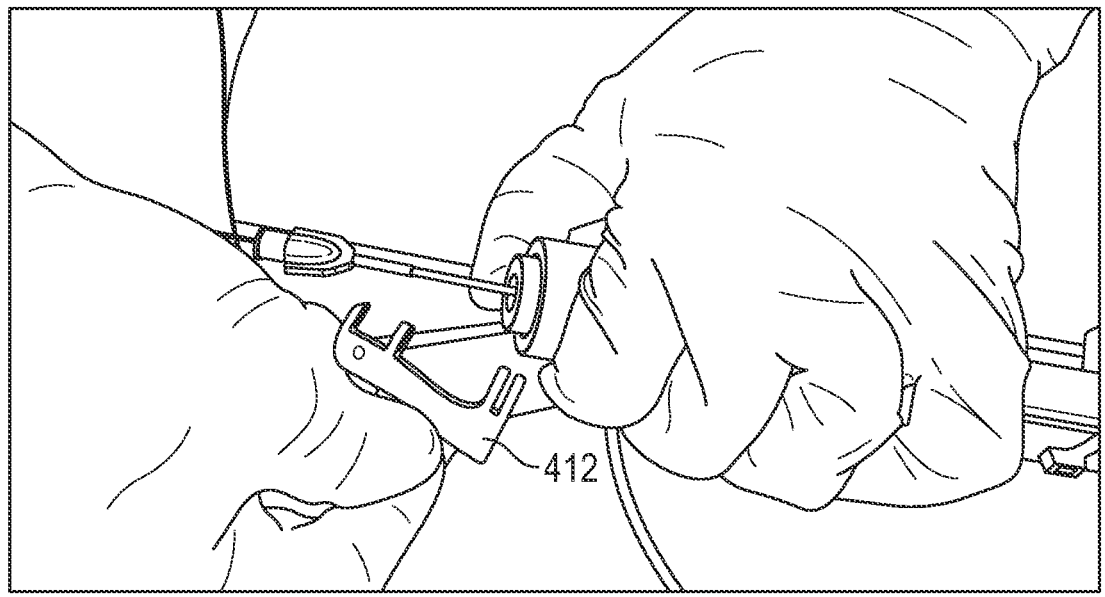
Figure 19D:
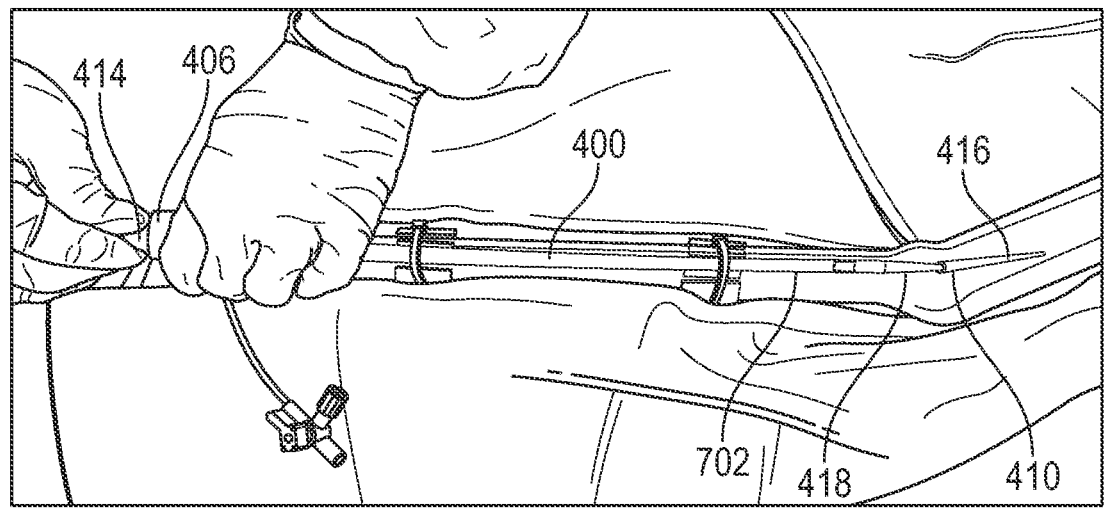
Figure 19E:
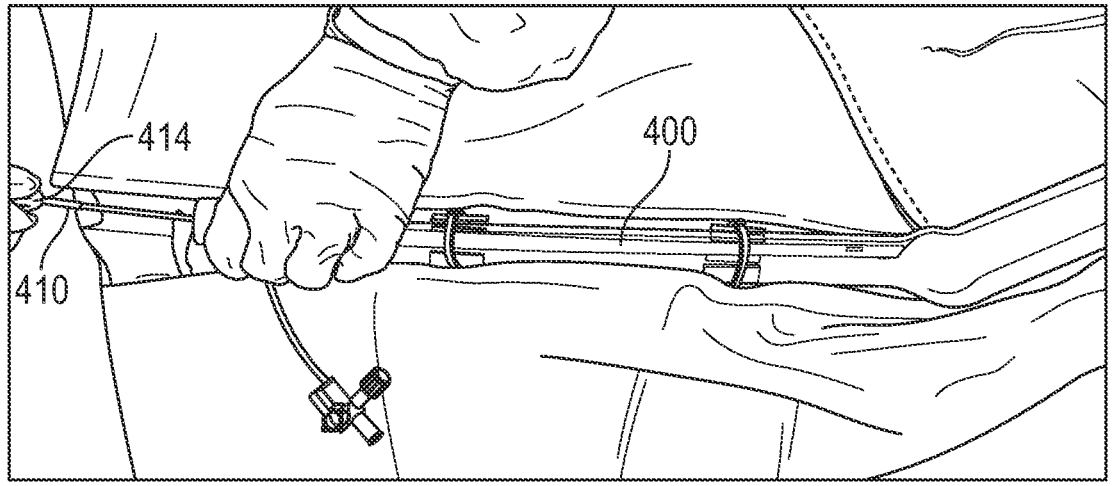
Figure 19F:
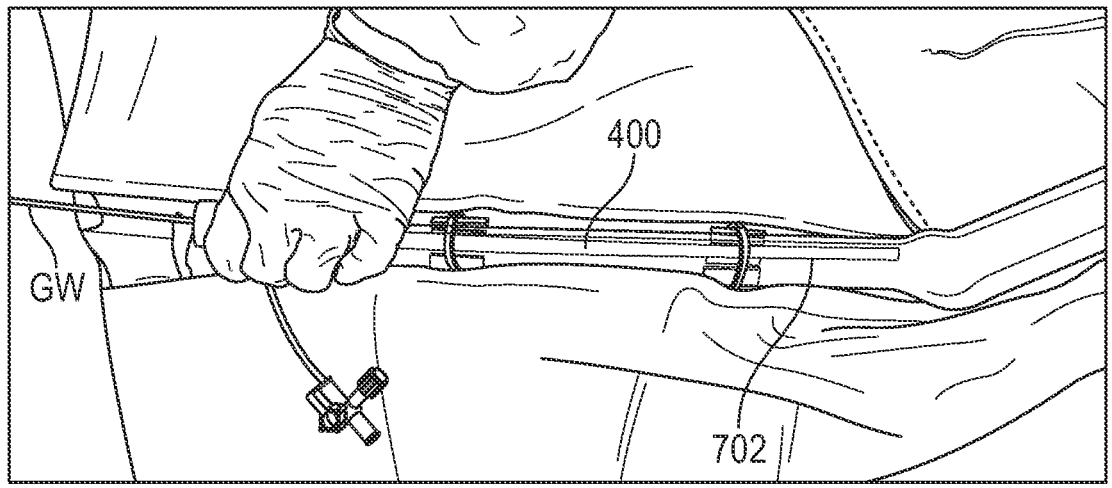
Figure 19G:
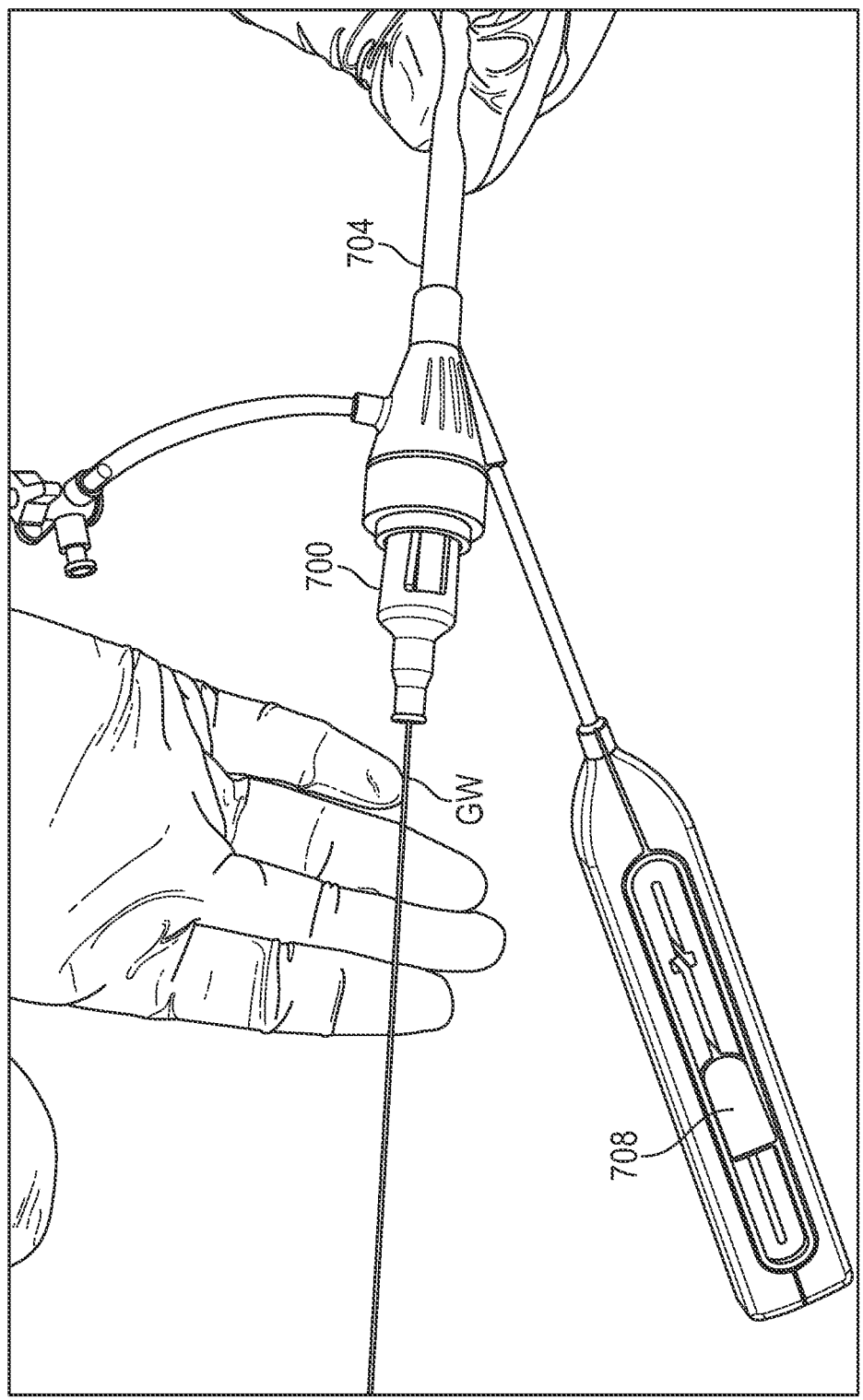
Figure 19H:
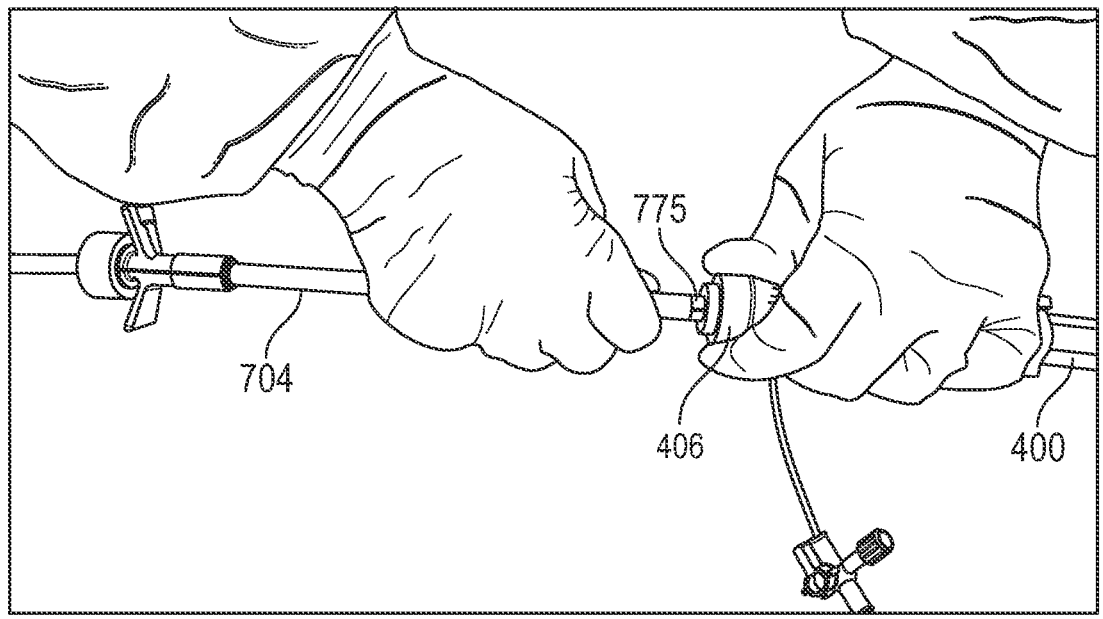
Figure 19I:
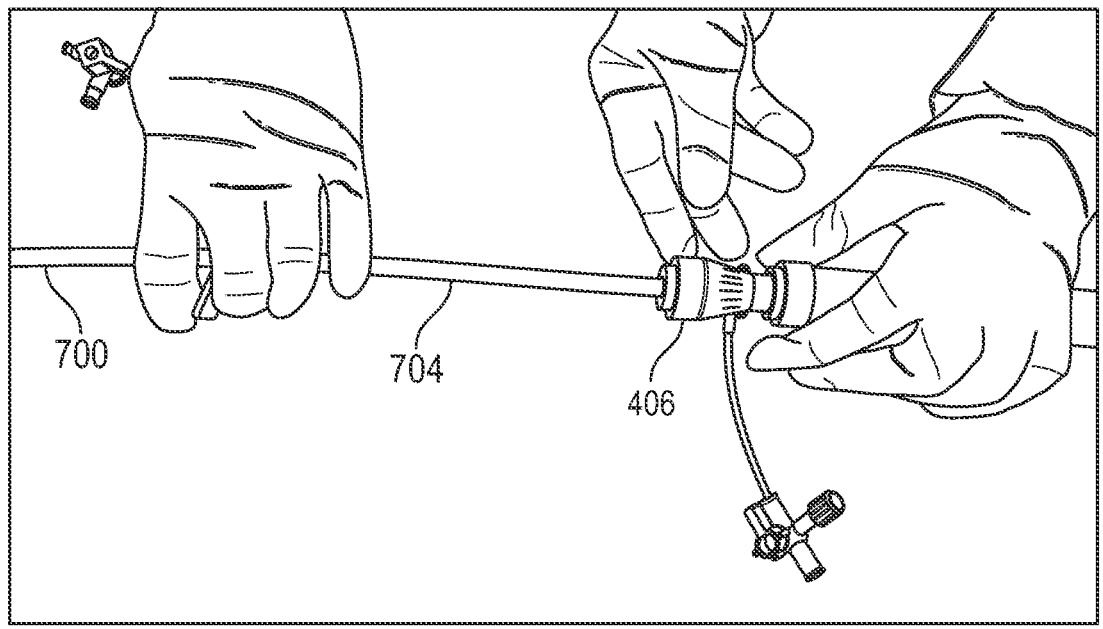
Figure 19J:
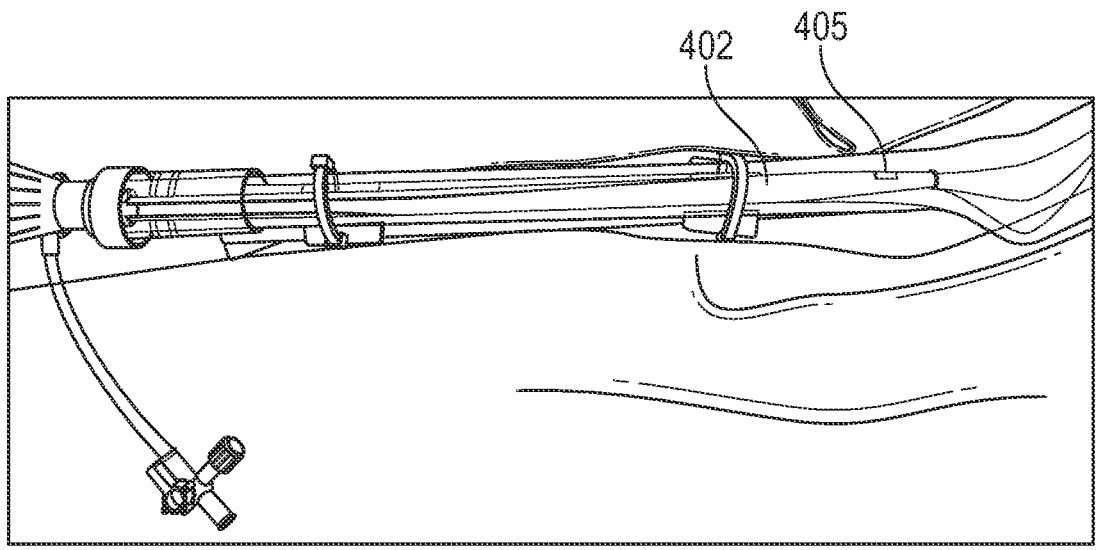
Figure 19K:
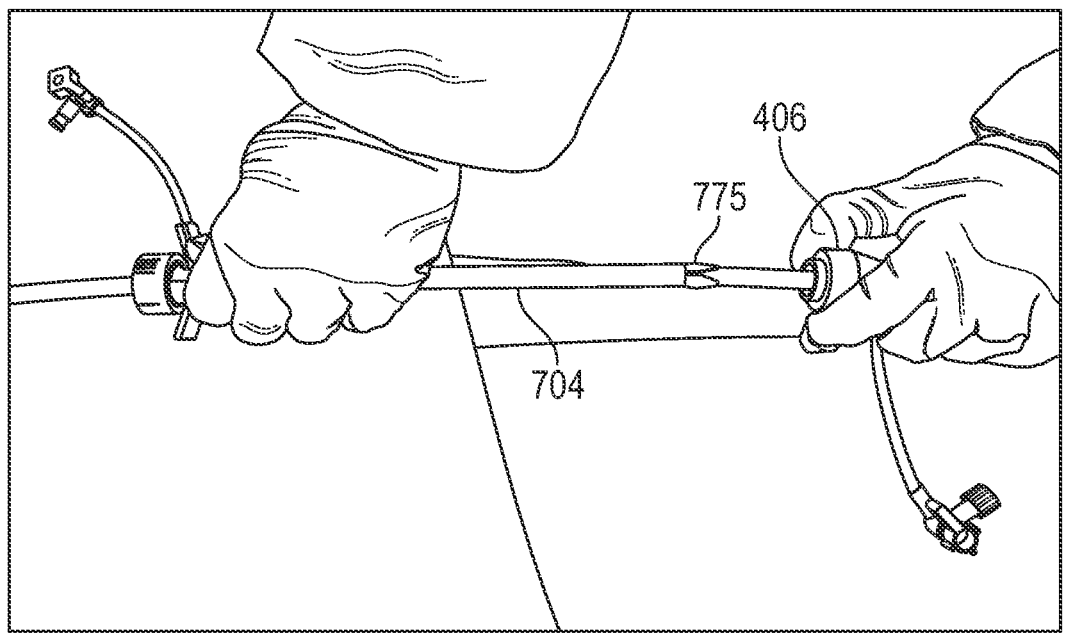
Figure 19L:
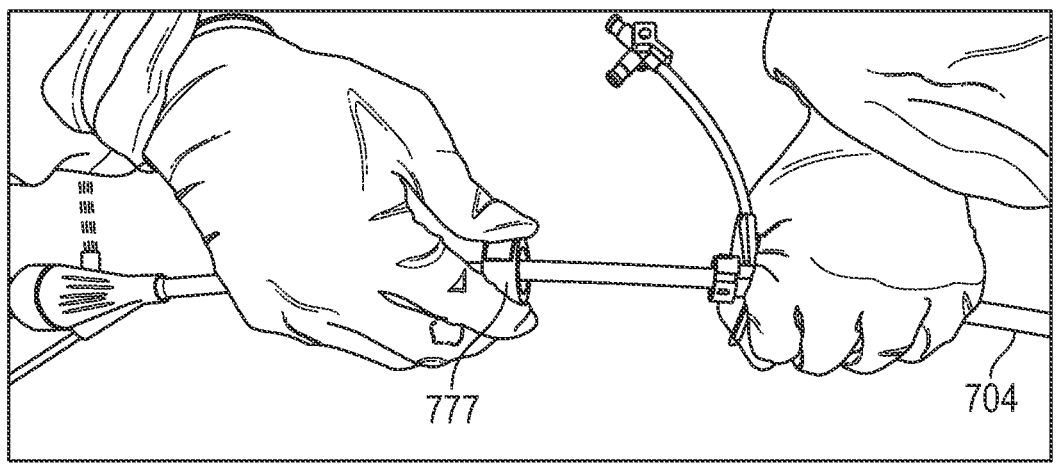
Figure 19M:
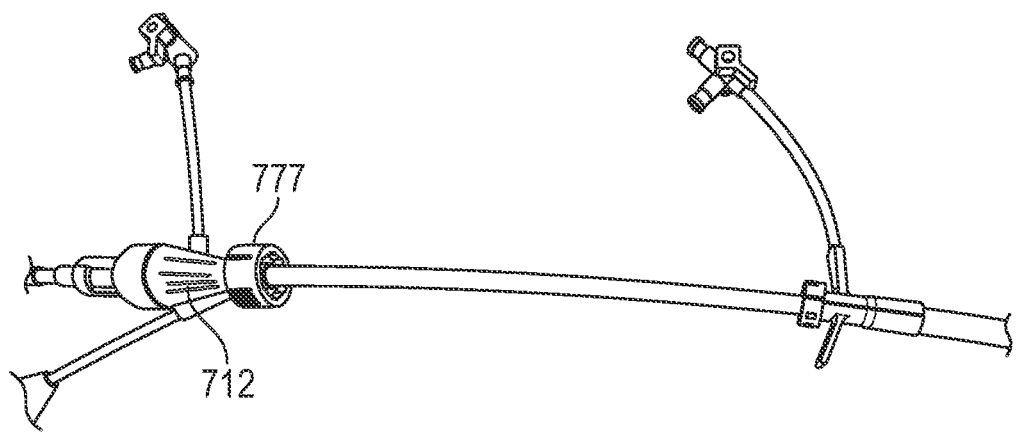
Figure 19N:
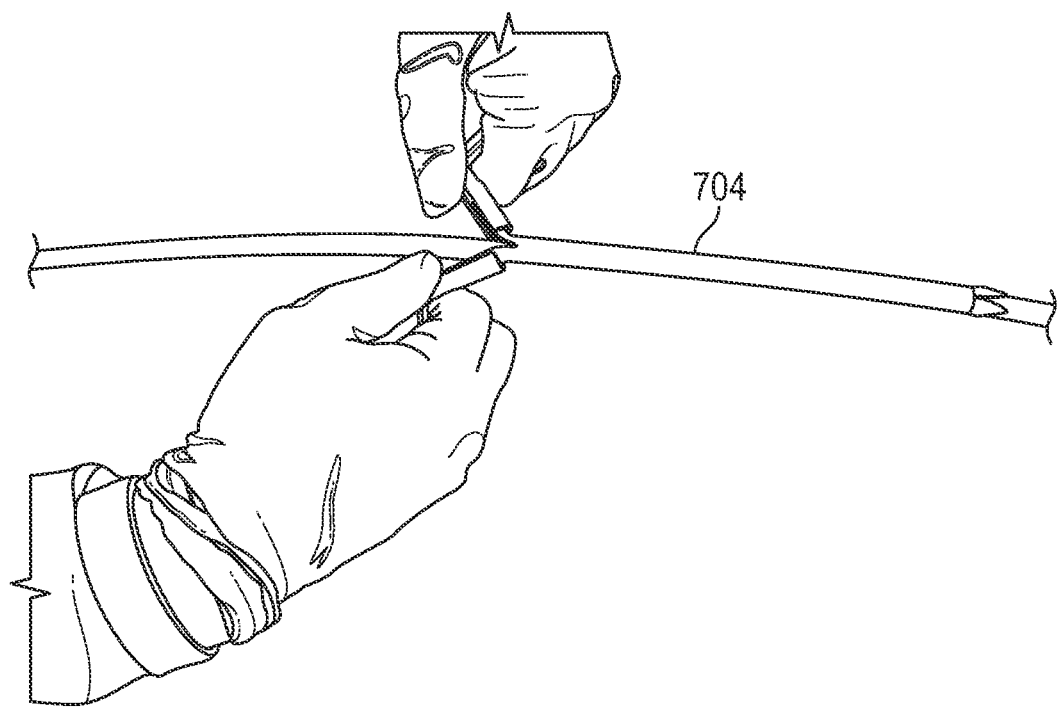
Figure 19O:
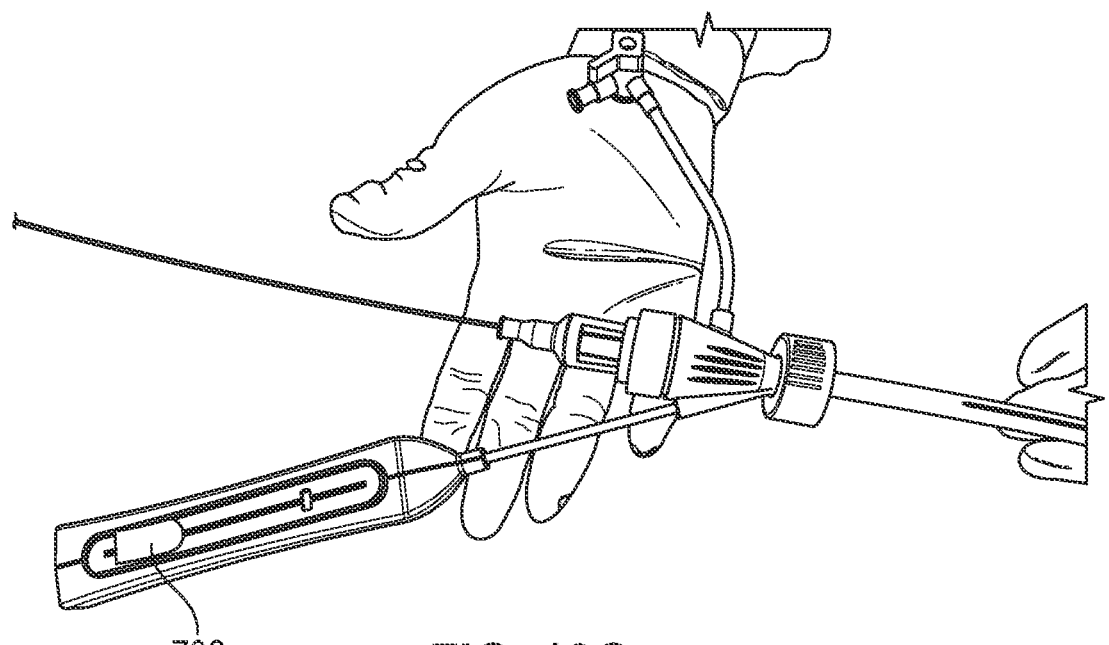
Figure 19P:
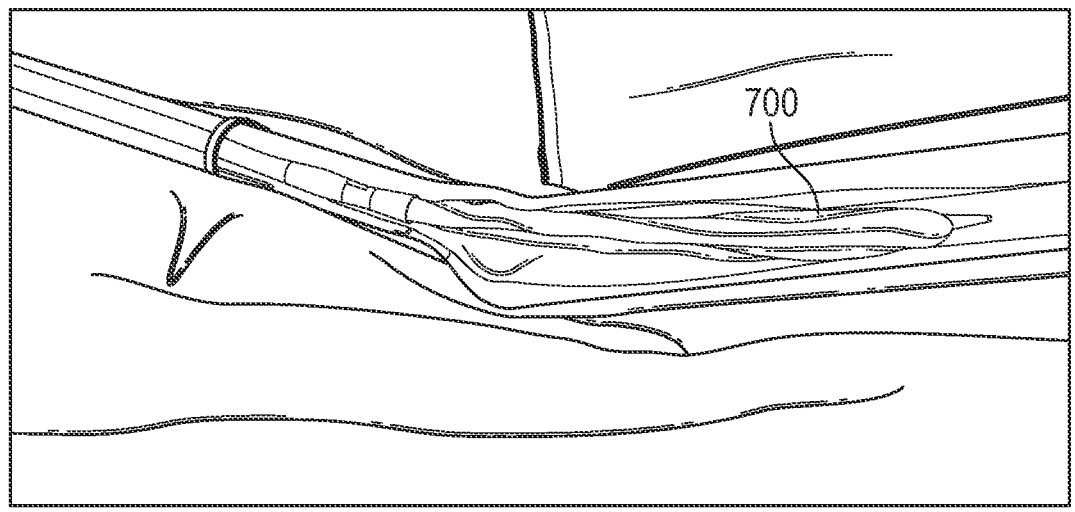
Figure 19Q:
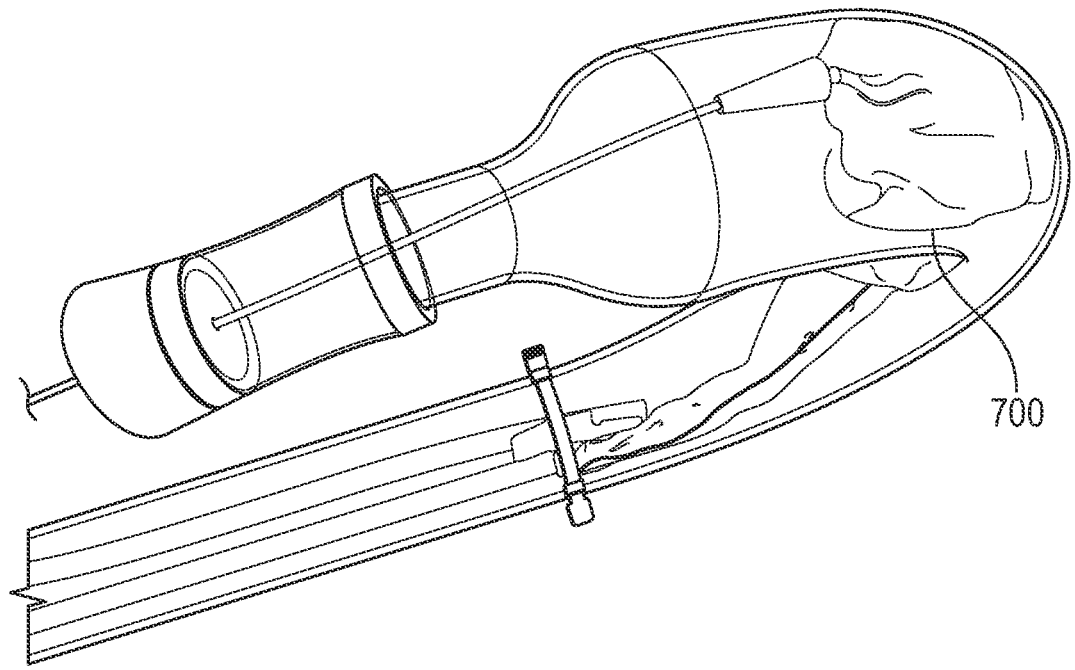
Figure 19R:
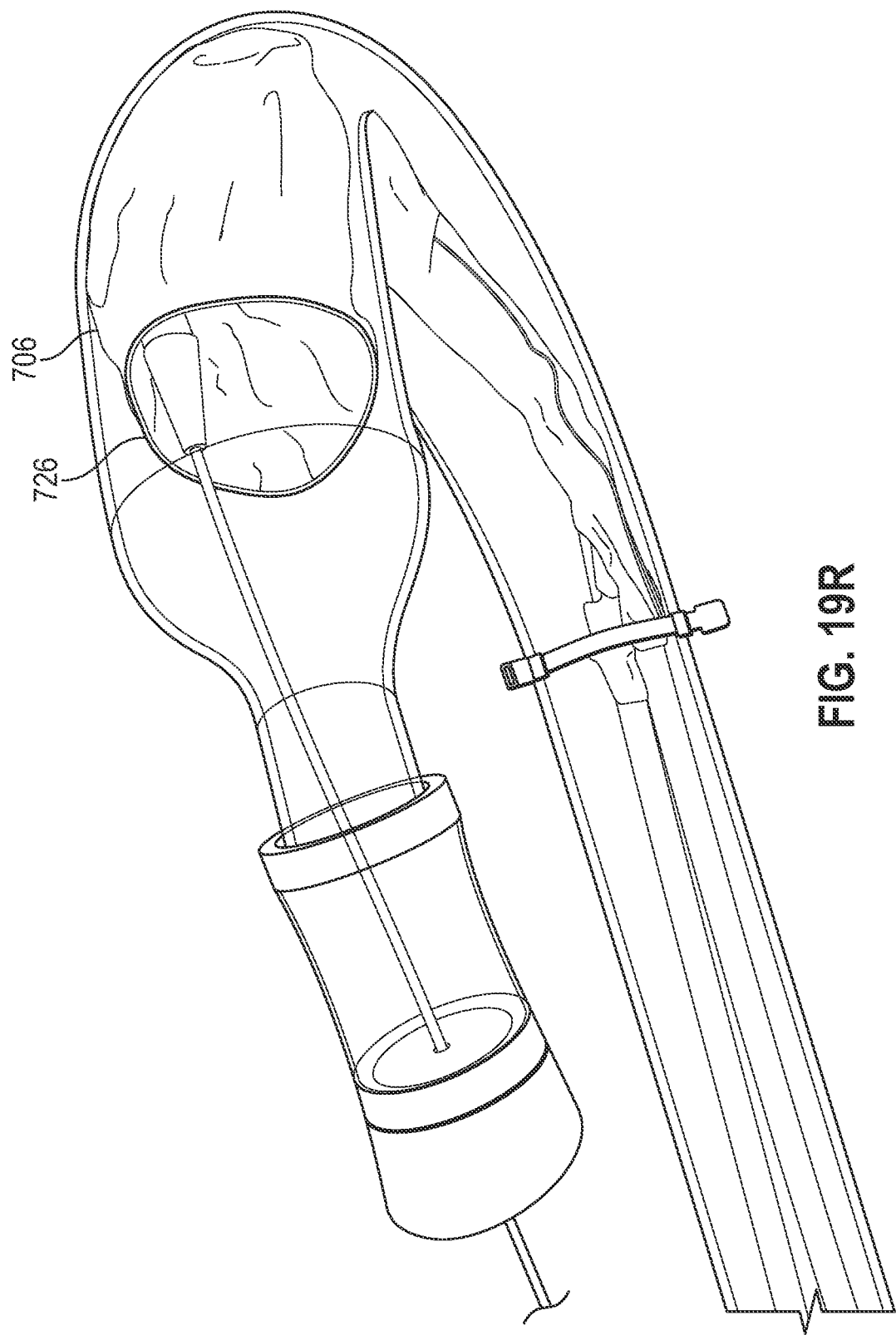
Figure 19S:
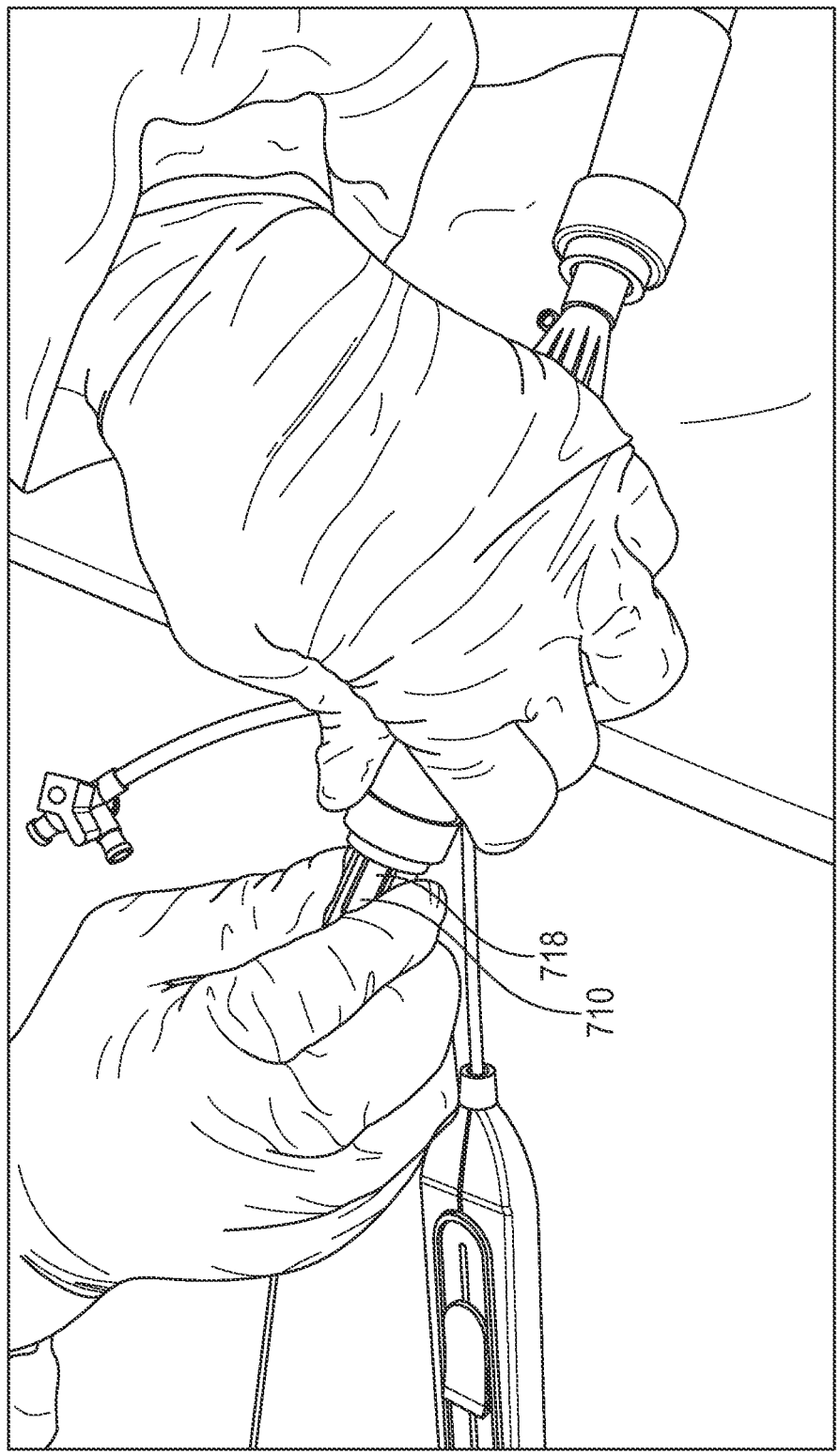
Figure 19T:
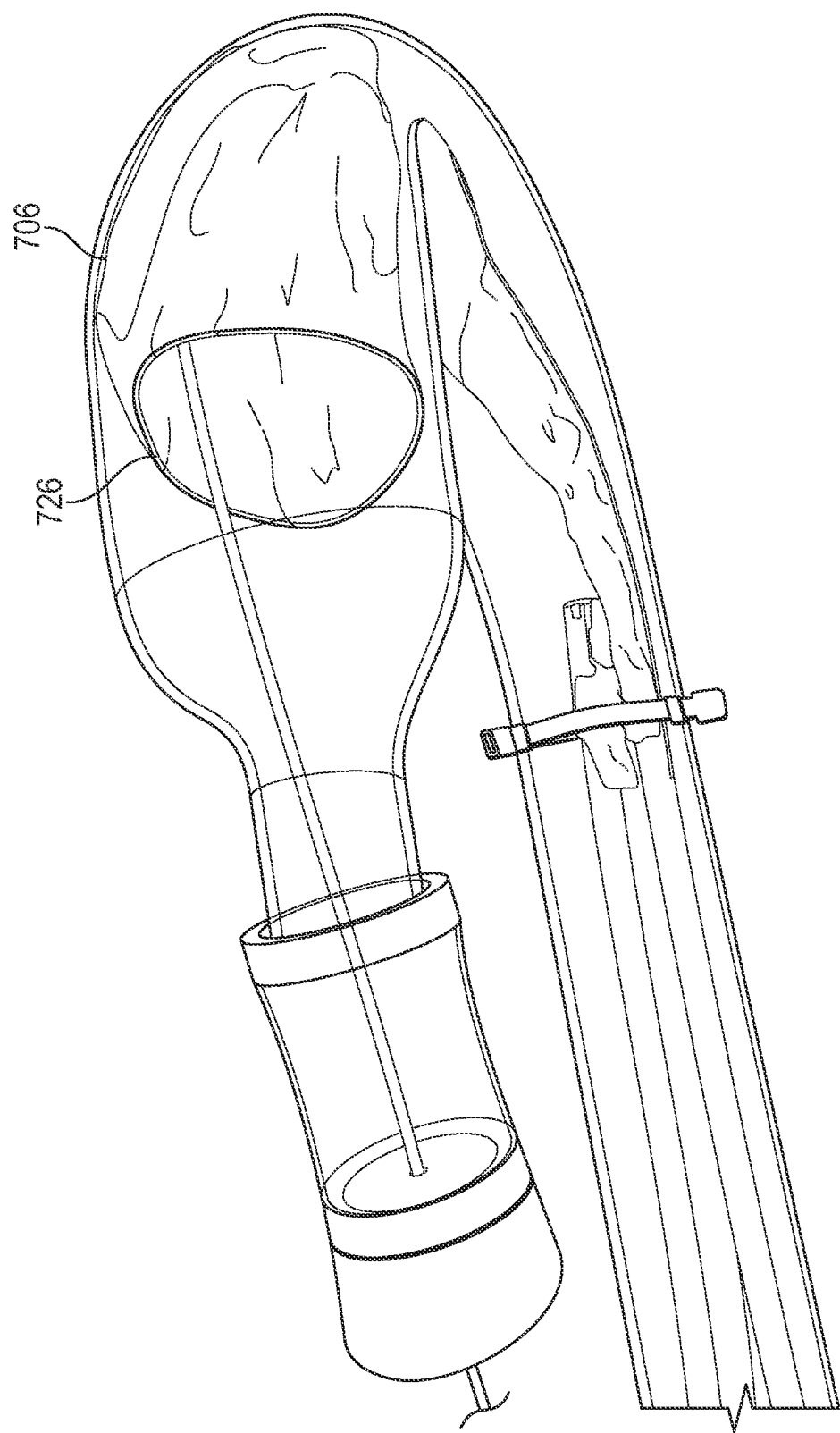
Figure 19U:
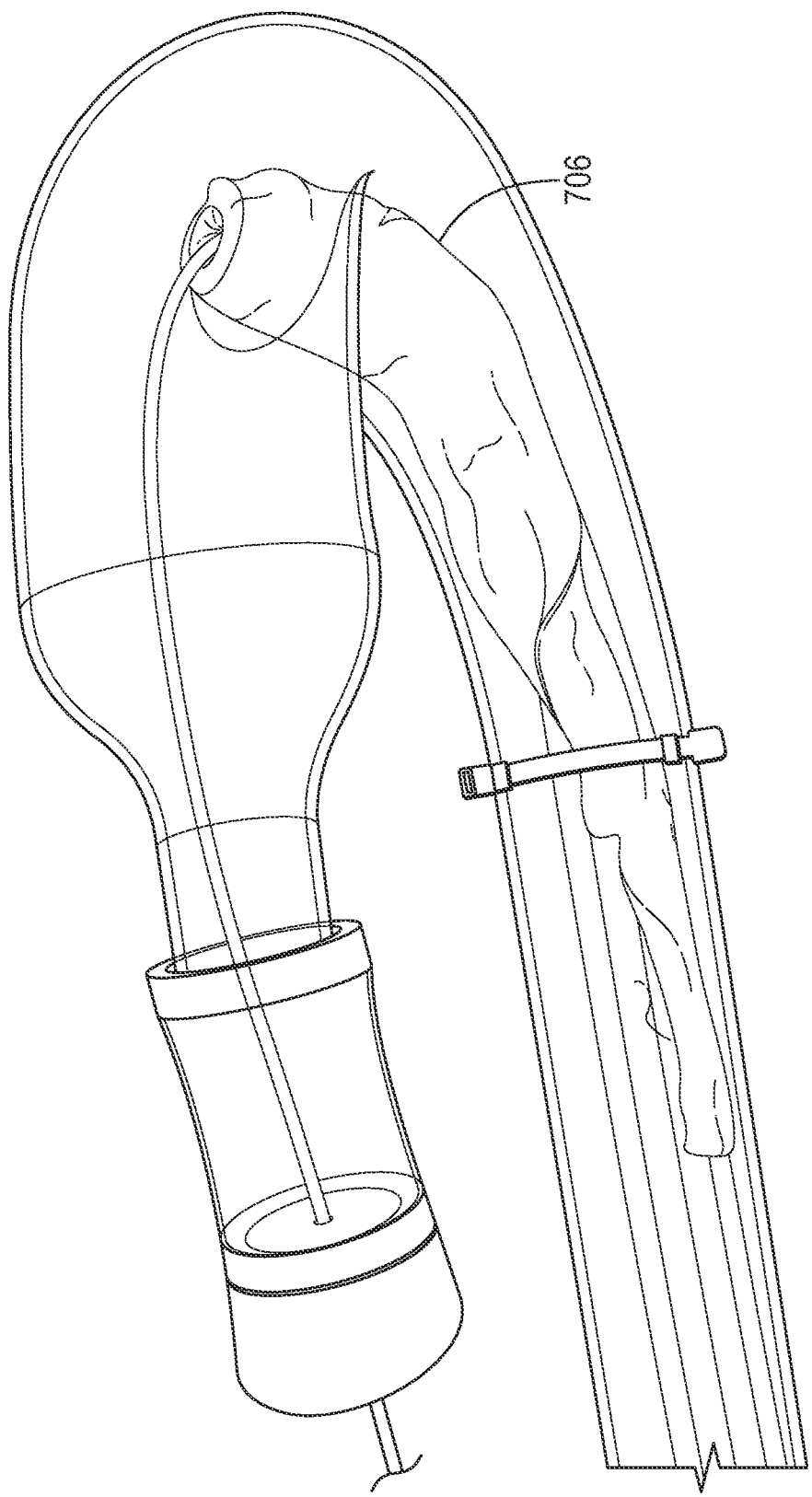
Figure 19V:
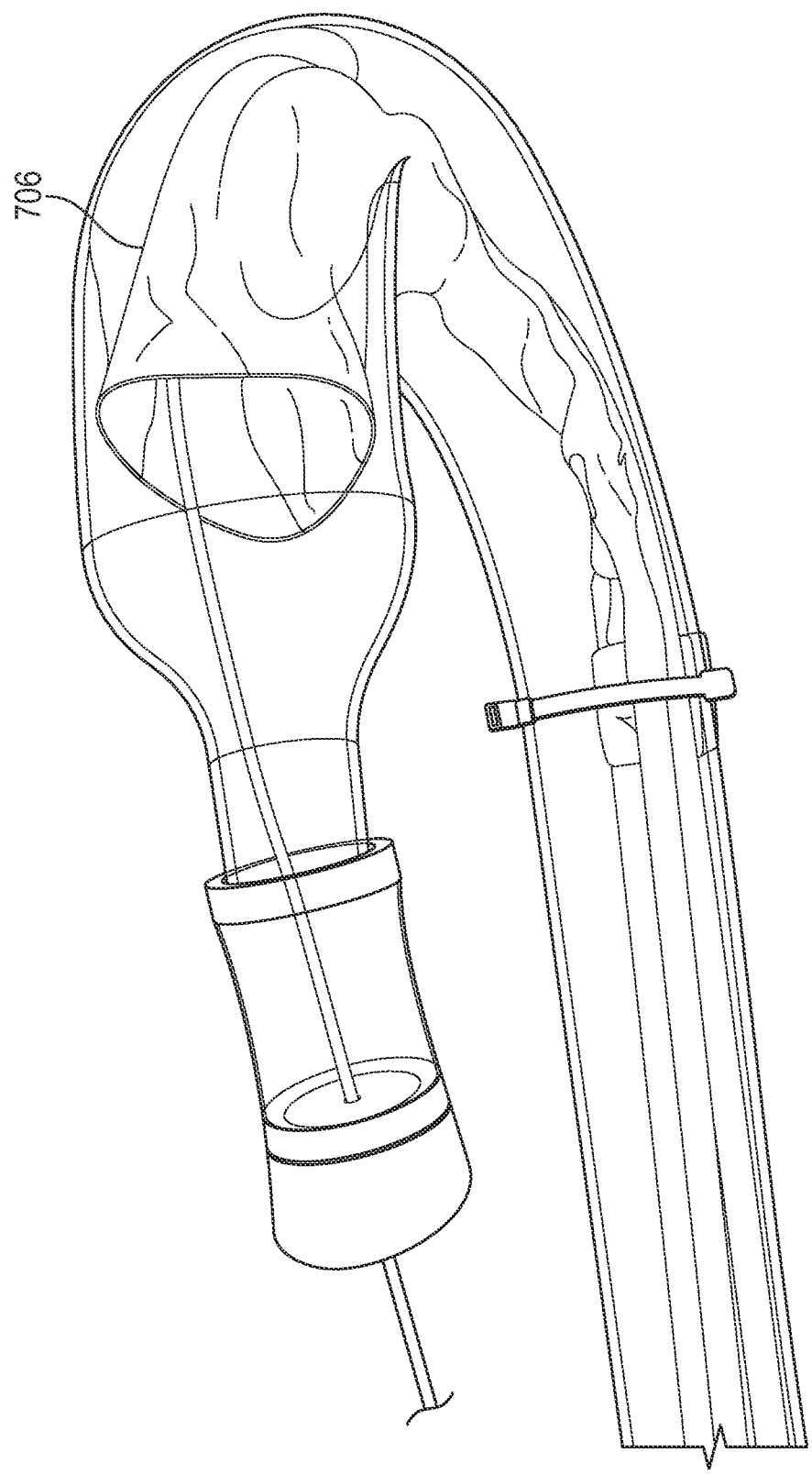
Figure 19W:
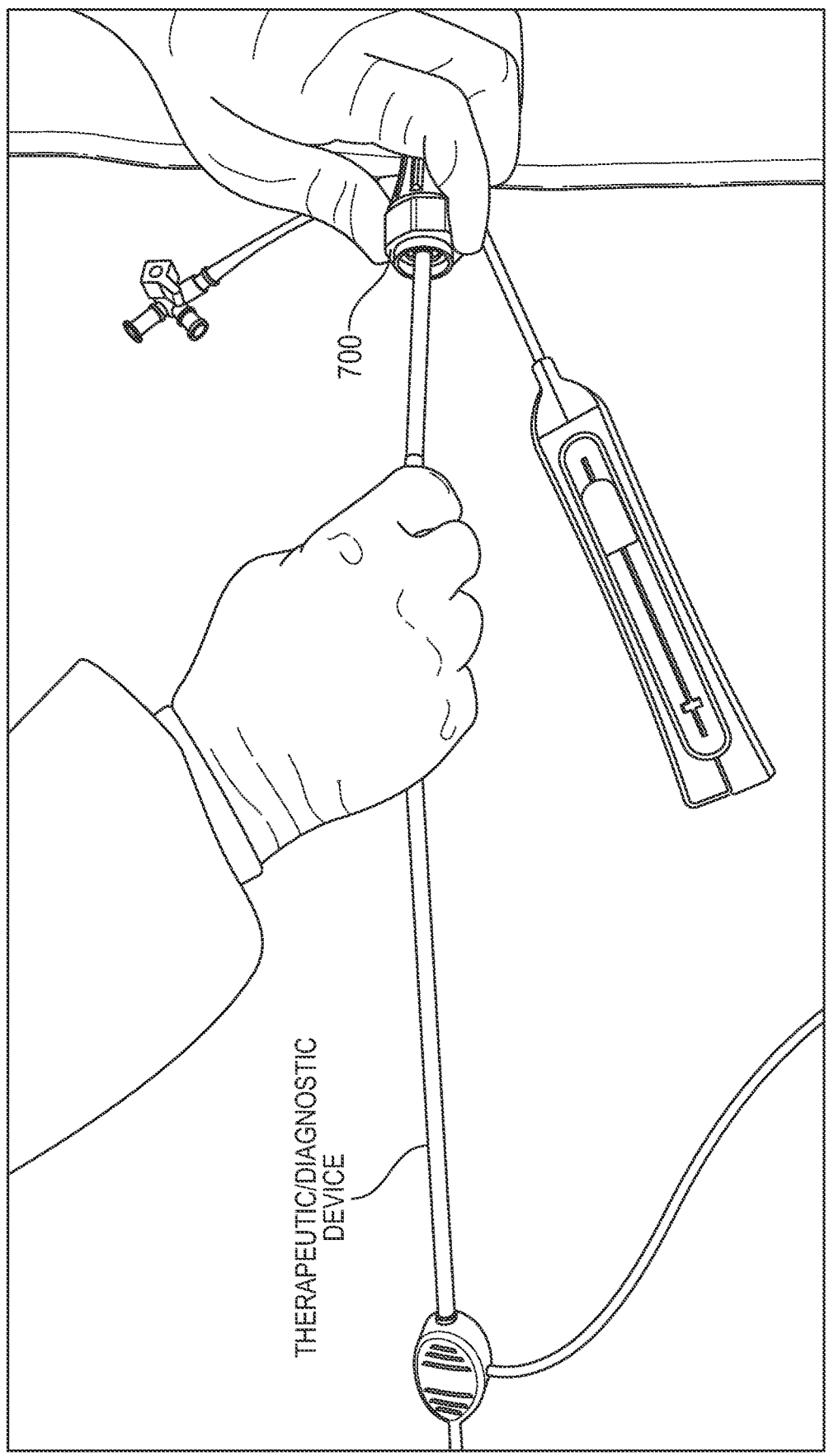
Figure 19X:
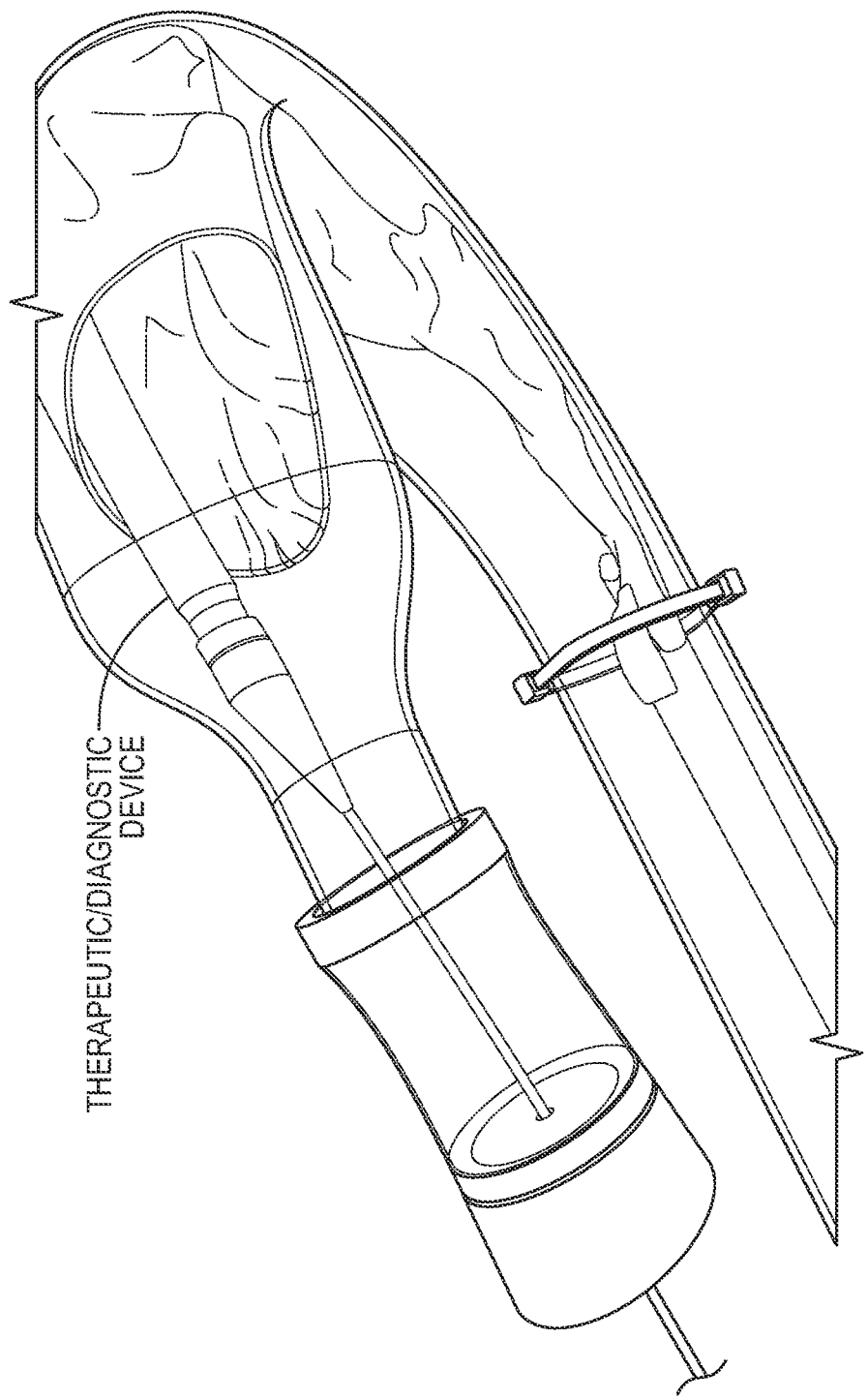

FIGS. 19A-19X show various aspects of a deployment technique of an embolic protection system 300 in accordance with the present disclosure. FIGS. 19A-19X illustrate a bench model with tubing zip tied to a work surface in the interest of clarity of explanation, rather than illustrating the features of the human vasculature. In this example the tubing represents the aorta and branches extending therefrom, but this is not intended to be limiting and one of skill in the art will appreciate that the tubing may represent other vessels or hollow passages in the body.

In FIG. 19A, an operator advances the expandable introducer 400 over a 0.035 guidewire into the human vasculature such as the aorta.

In FIGS. 19B-19C, the operator removes the clip 412 by first unclipping the dilator Luer fitting 414 (FIG. 19B), and then removing the clip 412 (FIG. 19C).

In FIG. 19D, the operator grips the dilator Luer fitting 414 and advances the dilator Luer fitting 414 until the dilator Luer fitting 414 contacts the introducer hub 406. It will be noted in the right of the view of FIG. 19D that advancement of the dilator Luer fitting 414 has caused the sheath dilator tip 416 of the sheath dilator 410 to unseat or release from the end of the mesh sheath 702. As described above, this release allows the uncapped open end 418 of the mesh sheath 702 to enlarge in size. The enlarged open end 418 of the mesh sheath 402 is larger than the outer diameter of the sheath dilator tip 416. As a result, the sheath dilator 410 is free to be retracted by an operator to withdraw the sheath dilator tip 416 back through the enlarged open end 418 of the mesh sheath 402 and extract the sheath dilator 410 and the sheath dilator tip 416 from the expandable introducer 400 as a whole.

In FIG. 19E, the operator slowly removes the sheath dilator 410 while grasping the dilator Luer fitting 414 to retract the sheath dilator 410 from the expandable introducer 400.

In FIG. 19F, the sheath dilator 410 has been completely removed from the expandable introducer 400 and only the guidewire (GW) is visible. The mesh sheath 702 remains in place in the human vasculature, here the aorta, to enclose and protect the embolic protection device 700 and the filter 706 during subsequent operations, as now described.

In FIG. 19G, the operator inserts the embolic protection device 700 with the loading sleeve 704 fitted thereto over the guidewire GW. The filter actuator 708 faces up and is parallel to the surgical table.

In FIG. 19H, the operator inserts the tip 775 of the loading sleeve 704 into the expandable introducer 400 via the introducer hub 406.

In FIG. 19I, while holding the introducer hub 406 (for example by a second operator), the first operator continues advancement of the embolic protection device 700 through the loading sleeve 704 and into the vasculature until the filter dilator tip 720 of the filter dilator 710 is aligned with the marker 405 (e.g. radiopaque or echogenic marker) on the mesh sheath 402 (FIG. 19J).

In FIG. 19K, the operator retracts the loading sleeve 704 gently until the tip 775 of the sleeve 704 has been taken out of the introducer hub 406.

In FIG. 19L, the operator twists and removes the locking cap 777 of the loading sleeve 704.

In FIG. 19M, the operator slides the locking cap 777 onto the catheter hub 712 and it may be snapped in place to prevent unwanted movement.

In FIG. 19N, the operator peels away and removes the loading sleeve 704. The two halves of the loading sleeve are peeled away from one another along a perforation or frangible connection to allow them to easily separate from one another.

In FIG. 19O, the operator verifies that the filter actuator 708 is facing up and parallel to the surgical table.

In FIG. 19P, the operator advances the embolic protection device 700 beyond the represented brachiocephalic trunk, toward the heart.

In FIG. 19Q, the operator advances the embolic protection device 700 into the aortic arch.

In FIG. 19I, the operator deploys the filter 706 (i.e., opens the filter mouth 726) using the filter actuator 708 (previously illustrated) and confirms that the filter is fully open and properly positioned (for example, using a visual aid such as camera probe in a real-life situation, or using fluoroscopy).

In FIG. 19S, the operator squeezes the release tabs of the snap-lock Luer fitting 718 and begins removing the filter dilator 710 while maintaining the guidewire in position.

In FIG. 19T, the filter dilator tip 720 is seen removed from the open mouth 726 of the filter 706.

In FIG. 19U, if the filter 706 is not properly positioned, the operator can close the filter 706 using the filter actuator 708 (previously illustrated) and reposition the filter as desired.

In FIG. 19V, the operator deploys (opens) the filter 706 at the desired new location using the filter actuator 708 (previously illustrated). The filter 706 is now ready to capture embolic material.

In FIG. 19W, the operator inserts an interventional device (for deploying a therapeutic device such as a prosthetic heart valve for example, other interventional device, or a diagnostic device) through the embolic protection device 700 towards, and proceeds into, the aortic arch for deployment of the therapeutic device (FIG. 19X).

Figure 20:
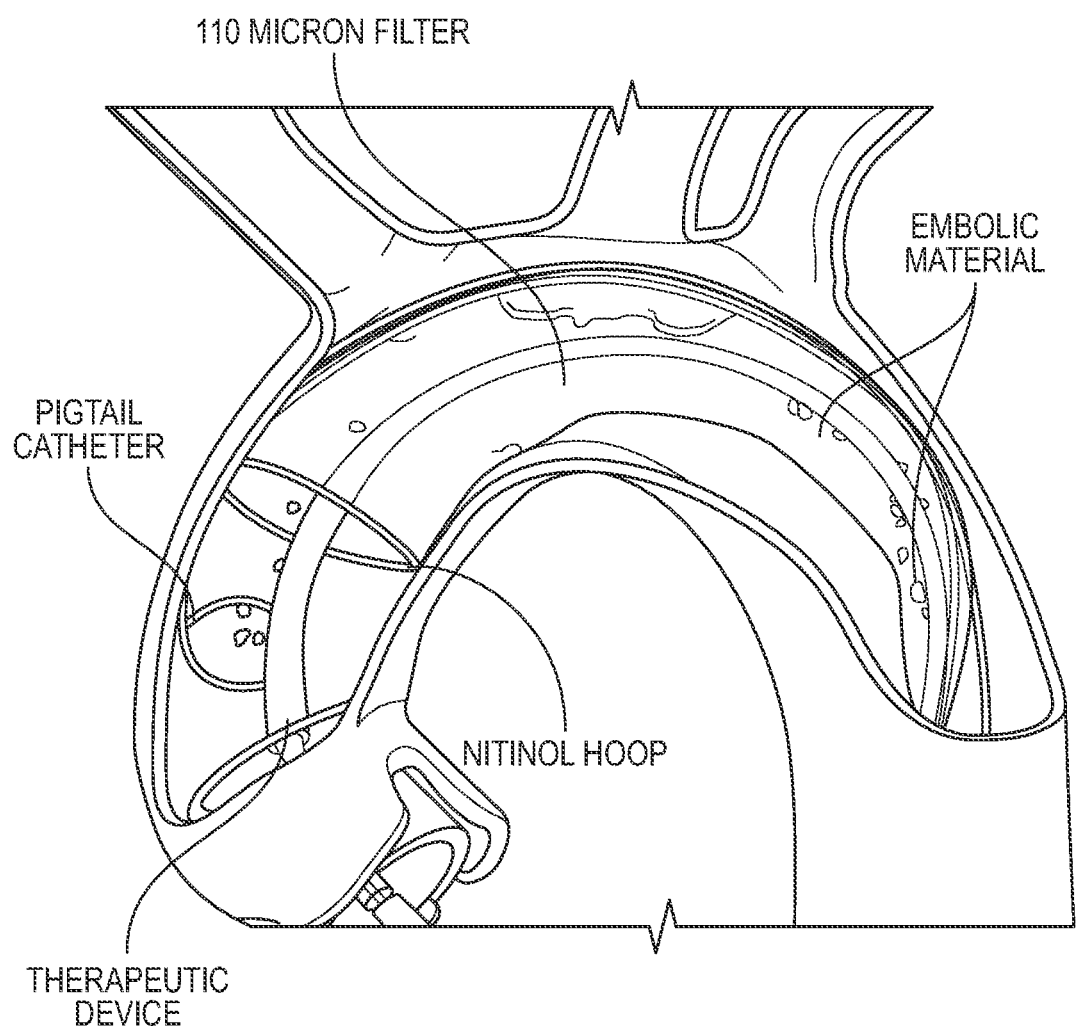
FIG. 20 shows a pictorial view of a deployed therapeutic device using an example embolic protection system of the present disclosure.

FIG. 20 shows a pictorial view of a deployed therapeutic device after passing through an embolic protection filtering device. In summary, as described above, the inventive protective configurations of the embolic protection system provide a means for conducting an intervention while also protecting the underlying tissue and related anatomy.

Figure 21A:
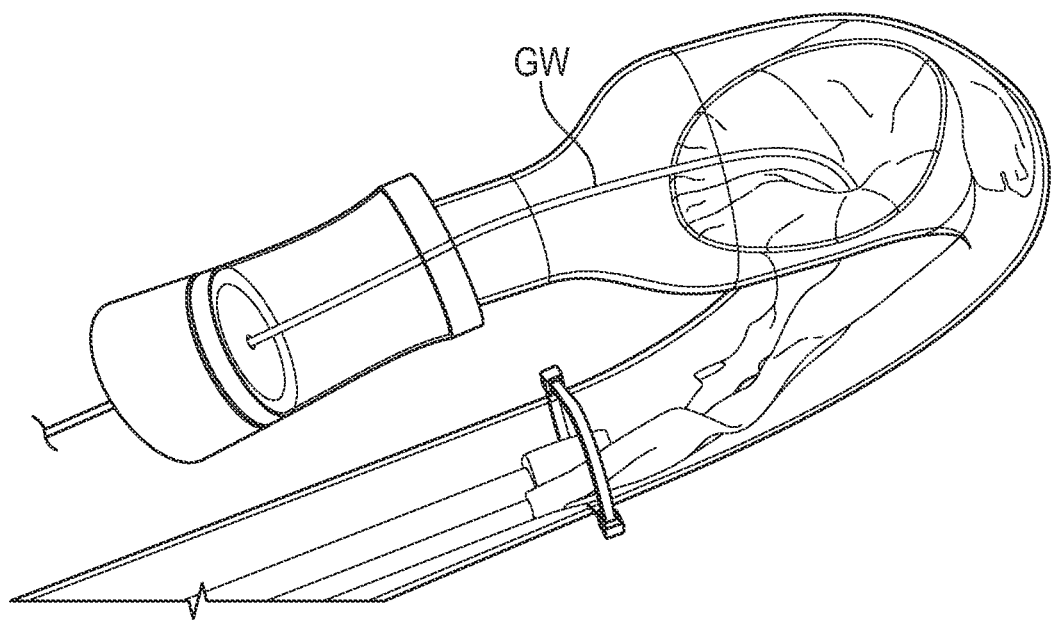
FIGS. 21A-21F show various aspects of a withdrawal technique, in accordance with the present disclosure.

After deploying the therapeutic device (a prosthetic valve, for example), in FIG. 21A, the operator removes the interventional device delivery system while maintaining the guidewire GW position.

Figure 21B:
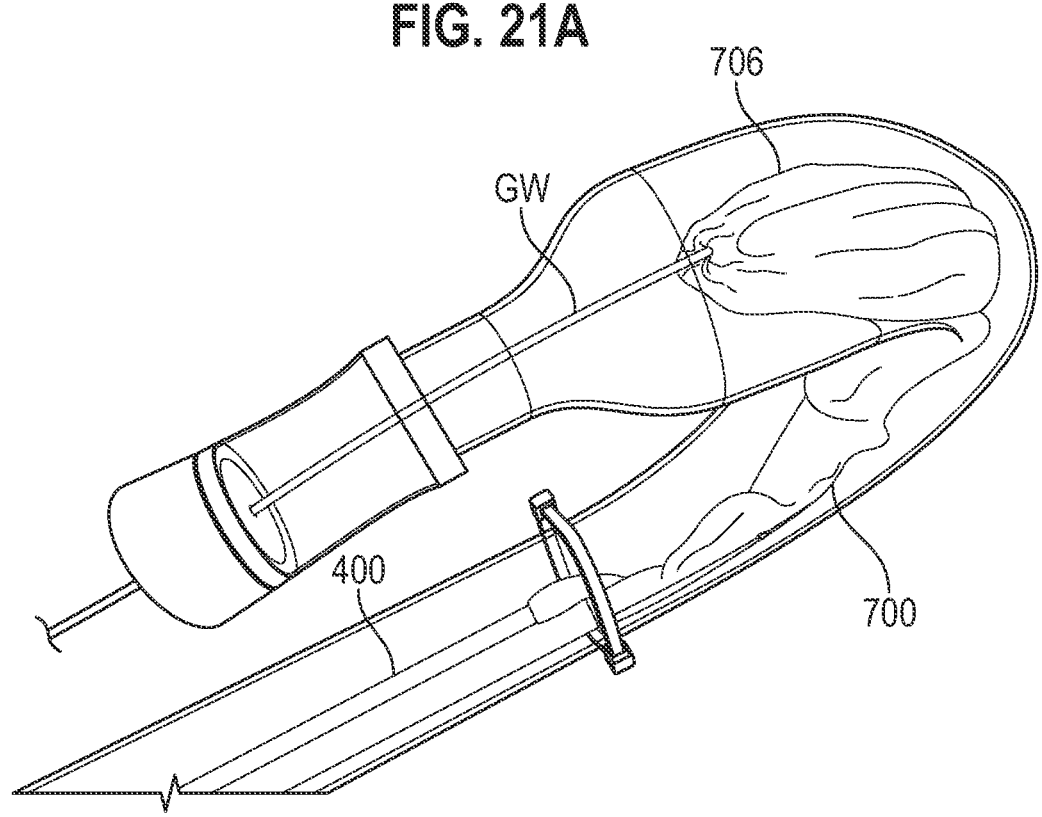

In FIG. 21B, upon completion of the procedure, the operator closes the filter 706 and gently removes the embolic protection device 700 and the closed filter 706 from the expandable introducer 400 while maintaining guide wire position.

Figure 21C:
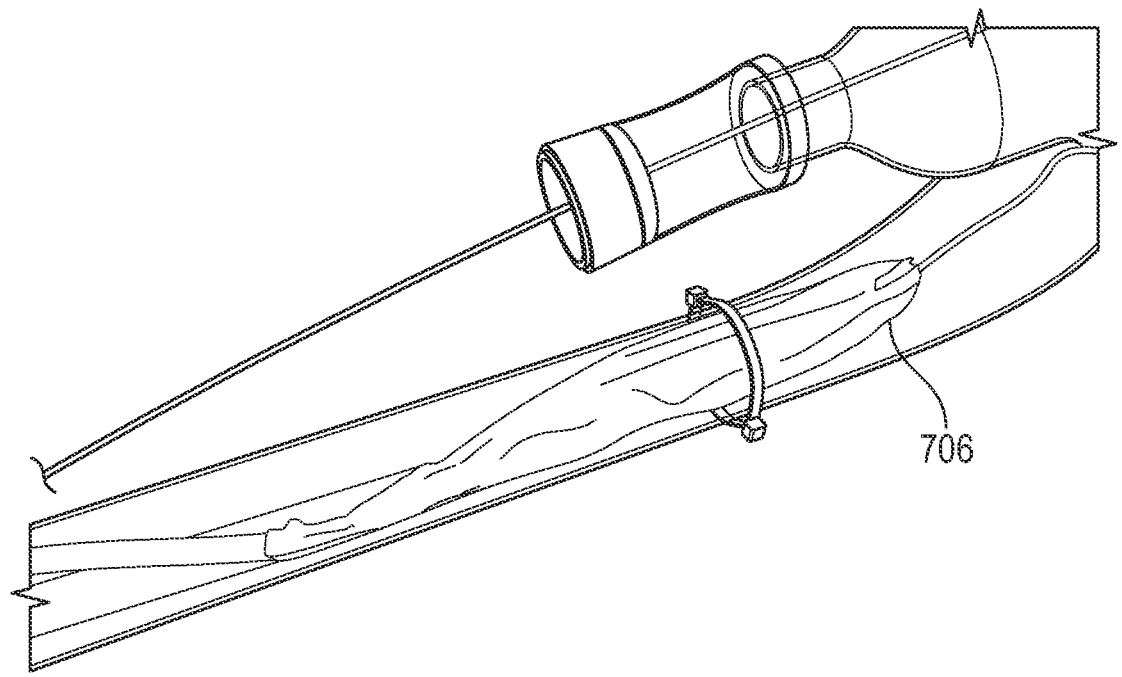

During withdrawal (FIG. 21C), the closed filter 706 securely traps for removal embolic material that may have been released during the procedure.

Figure 21D:
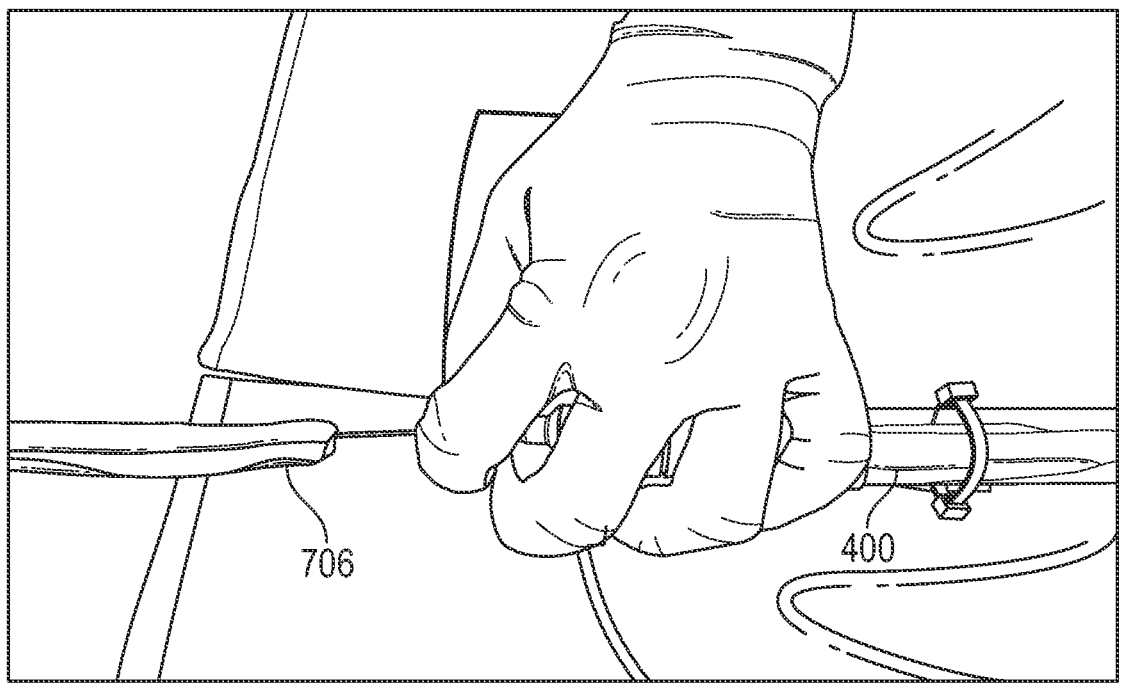

In FIG. 21D, the filter 706 is shown completely withdrawn from the expandable introducer 400.

Figure 21E:
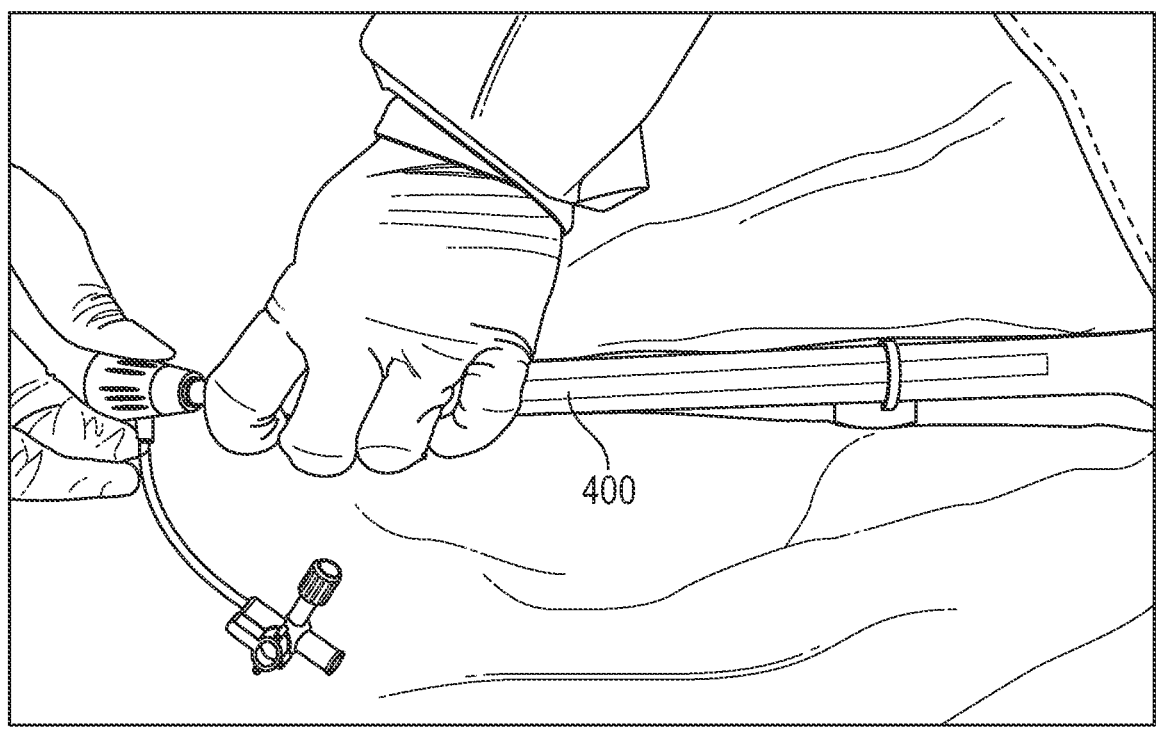

In FIG. 21E, the operator gently withdraws and removes the expandable introducer 400 from the arterial circulation (vasculature) when the procedure has been completed.

Figure 21F:
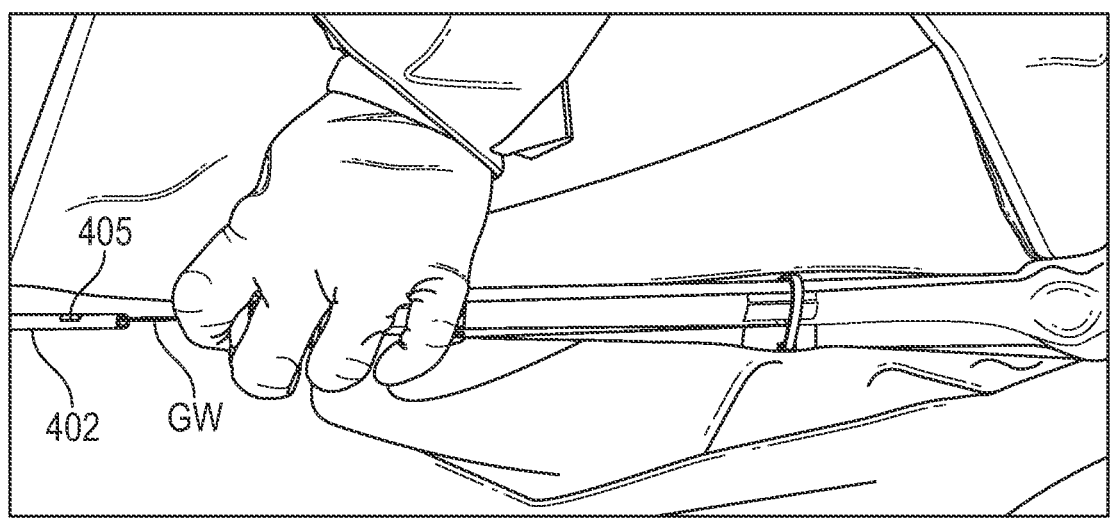

In FIG. 21F, the marker (e.g. radiopaque marker or echogenic marker) 405 on the mesh sheath 402 of the expandable introducer is shown fully removed from the patient and the guidewire can be withdrawn.

The present disclosure describes a system which includes several components (e.g. an expandable sheath, a sheath dilator, an embolic protection device, a peel away sheath, dilator for the embolic protection device, etc.). These components may be used all together as a kit, or they may be provided individually and used individually, or they may be provided and used in any combination. Some examples of combinations include but are not limited to: the expandable sheath alone or the expandable sheath in combination with the sheath dilator; the embolic protection device alone or in combination with the peel away sheath and/or the embolic protection device dilator. Or the expandable sheath may be combined with the embolic protection device and any of the other components which may be combined with the expandable sheath or the other components which may be combined with the embolic protection device. Therefore any combination of the components disclosed herein is contemplated.

NOTES AND EXAMPLES

The following non-limiting examples detail certain aspects of the present subject matter to solve at least some of the challenges and provide at least some of the benefits discussed herein, among others.

Example 1 is an embolic protection system for deploying a device in a diseased vessel of a vasculature, the embolic protection system comprising: an embolic protection device including: a catheter shaft; an expandable filter provided at a distal end of the catheter shaft; a filter actuator located at or towards a proximal end of the embolic protection device, the filter actuator operable to open and close a mouth of the expandable filter.

Example 2 is the system of Example 1, further comprising an expandable introducer including: a mesh sheath of expandable porous mesh material; an introducer hub including a hemostasis valve; and a sheath dilator for dilating the mesh sheath, the sheath dilator insertable into the introducer hub and including, at a distal end of the sheath dilator, a sheath dilator tip which, in a loaded configuration of the sheath dilator, covers and restrains a distal open end of the mesh sheath; a loading sleeve to assist in loading the embolic protection device into the expandable introducer; and a filter dilator insertable into a lumen of the catheter shaft.

Example 3 is the system of any of Examples 1-2, wherein the mesh material of the mesh sheath is expandable in a radial direction of the mesh sheath.

Example 4 is the system of any of Examples 1-3, wherein the expandable porous mesh material of the expandable introducer is provided in a first porous region of the mesh sheath, the mesh sheath further comprising a second non-porous region of the mesh sheath.

Example 5 is the system of any of Examples 1-4, wherein the second non-porous region of the mesh is less radially expandable than the first porous region of the mesh sheath.

Example 6 is the system of any of Examples 1-5, wherein the sheath dilator tip is connected to a dilator Luer fitting provided at a proximal end of the sheath dilator, wherein advancement of the dilator Luer fitting distally by an operator causes the sheath dilator tip to unseat from and release the distal open end of the mesh sheath to adopt a deployed configuration of the expandable introducer.

Example 7 is the system of any of Examples 1-6, wherein advancement of the dilator Luer fitting proximally by an operator allows withdrawal of the sheath dilator tip through the released distal open end of the mesh sheath after release of the distal open end of the mesh sheath from the sheath dilator tip.

Example 8 is the system of any of Examples 1-7, wherein the expandable introducer includes a removable clip to lock the sheath dilator in the loaded configuration.

Example 9 is the system of any of Examples 1-8, wherein the embolic protection device further comprises: a catheter hub including a hemostasis valve to seal and guide the filter dilator when inserted into the lumen of the catheter shaft; a first connector for receiving a proximal end of the catheter shaft; and a second connector for connection to a flushing stopcock.

Example 10 is the system of any of Examples 1-9, wherein the mouth of the expandable filter includes a hoop wire connected by an actuation wire to a slider of the filter actuator, wherein movement of the slider by an operator causes a corresponding contraction or expansion of the hoop wire thereby to close or open the mouth of the expandable filter.

Example 11 is the system of any of Examples 1-10, wherein the actuation wire is at least partly carried in a tubular rail provided at a distal end of the catheter shaft.

Example 12 is the system of any of Examples 1-11, wherein the filter dilator includes a formation provided at or towards a distal end of the filter dilator to capture or retain the mouth of the expandable filter when closed by the hoop wire.

Example 13 is the system of any of Examples 1-12, wherein the filter dilator further comprises a filter dilator tip, and wherein the formation includes a circumferential channel formed in the filter dilator tip.

Example 14 is the system of any of Examples 1-13, wherein the filter actuator includes a locking mechanism operable to lock the closed mouth of the expandable filter in the circumferential channel in the filter dilator tip.

Example 15 is the system of any of Examples 1-14, wherein the loading sleeve is a peel-away loading sleeve comprising separable elements that can be parted by an operator to remove the loading sleeve from the embolic protection device, the separable elements defining, before separation, a lumen of the loading sleeve, the lumen sized to receive and guide the embolic protection device into the expandable introducer.

Example 16 is the system of any of Examples 1-15, wherein the separable elements, before separation, are locked together by a locking cap, wherein removal by an operator of the locking cap allows separation of the separable elements.

Example 17 is a method of deploying an embolic protection device into a vasculature of a patient, the method comprising: establishing access to the vasculature; introducing a guide wire into the vasculature to assist with guidance of the embolic protection device through the vasculature; advancing the embolic protection device into the vasculature and over the guide wire toward a target treatment region, wherein the embolic protection device comprises a catheter shaft, an expandable filter disposed at a distal end of the catheter shaft, a filter actuator disposed adjacent a proximal end of the catheter shaft, wherein the filter actuator is operable to open and close a mouth of the expandable filter; actuating the filter actuator thereby radially expanding the expandable filter at the target treatment region and opening the mouth of the expandable filter; and capturing emboli in the expandable filter.

Example 18 is the method of Example 17, further comprising inserting a therapeutic device through the embolic protection device and advancing the therapeutic device toward the target treatment region.

Example 19 is the method of any of Examples 17-18, wherein the target treatment area comprises a native aortic valve.

Example 20 is the method of any of Examples 17-19, further comprising, after inserting the therapeutic device through the embolic protection device, closing the expandable filter and withdrawing the embolic protection device from the vasculature.

Example 21 is the method of any of Examples 17-20, further comprising advancing the embolic protection device through an expandable sheath, the expandable sheath disposed in the vasculature.

Example 22 is the method of any of Examples 17-21, further comprising radially expanding the expandable sheath after unseating a distal end of the expandable sheath from a sheath dilator tip coupled to a sheath dilator, the sheath dilator disposed in the expandable sheath.

Example 23 is the method of any of Examples 17-22, further comprising removing a loading sleeve from the embolic protection device thereby allowing radial expansion of the expandable filter.

In Example 24, the apparatuses, systems, or methods of any one or any combination of Examples 1-23 can optionally be configured such that all elements or options recited are available to use or select from.

Various exemplary embodiments of the invention are described herein. Reference is made to these examples in a non-limiting sense. They are provided to illustrate more broadly applicable aspects of the invention. Various changes may be made to the invention described without departing from the scope of the invention as defined by the appended claims. In addition, many modifications may be made to adapt a particular situation, material, composition of matter, process, process act(s) or step(s) to the objective(s), or scope of the present invention. Further, as will be appreciated by those with skill in the art that each of the individual variations described and illustrated herein has discrete components and features which may be readily separated from or combined with the features of any of the other several embodiments without departing from the scope of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The present application discloses methods that may be performed using the subject devices. The methods may comprise the act of providing such a suitable device. Such provision may be performed by the end user. In other words, the "providing" act merely requires the end user obtain, access, approach, position, set-up, activate, power-up, or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the present disclosure in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described without departing from the scope of the invention defined by the appended claims. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only," and the like in connection with the recitation of claim elements, or use of a "negative" limitation.

Without the use of such exclusive terminology, the term "comprising" in claims associated with this disclosure shall allow for the inclusion of any additional element-irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure as defined by the appended claims.

The invention claimed is:

1. An embolic protection device including:
   a catheter shaft;
   an expandable filter provided at a distal end of the catheter shaft;
   a filter actuator located at or towards a proximal end of the embolic protection device, the filter actuator operable to open and close a mouth of the expandable filter, wherein the mouth of the expandable filter includes a hoop wire connected by an actuation wire to the filter actuator; and
   a filter dilator insertable into a lumen of the catheter shaft, wherein the filter dilator comprises a filter dilator tip, and wherein the filter dilator tip includes a circumferential channel to capture or retain the hoop wire of the mouth of the expandable filter when the mouth of the expandable filter is closed by the actuation wire.

2. The embolic protection device of claim 1, wherein the embolic protection device further comprises:
   a catheter hub including a hemostasis valve to seal and guide the filter dilator when inserted into the lumen of the catheter shaft;
   a first connector for receiving a proximal end of the catheter shaft; and
   a second connector for connection to a flushing stopcock.

3. The embolic protection device of claim 1, wherein movement of a slider of the filter actuator by an operator causes a corresponding contraction or expansion of the hoop wire thereby to close or open the mouth of the expandable filter.

4. The embolic protection device of claim 1, wherein the actuation wire is at least partly carried in a tubular rail provided at a distal end of the catheter shaft.

5. The embolic protection device of claim 1, wherein the filter actuator includes a locking mechanism operable to lock the closed mouth of the expandable filter in the circumferential channel in the filter dilator tip.

6. An embolic protection system for deploying a therapeutic device into a vasculature, the embolic protection system comprising:
   an embolic protection device including:
      a catheter shaft;
      an expandable filter provided at a distal end of the catheter shaft;
   a filter actuator located at or towards a proximal end of the embolic protection device, the filter actuator operable to open and close a mouth of the expandable filter, wherein the mouth of the expandable filter includes a hoop wire connected by an actuation wire to the filter actuator; and
      a filter dilator insertable into a lumen of the catheter shaft, wherein the filter dilator comprises a filter dilator tip, and wherein the filter dilator tip includes a circumferential channel to capture or retain the hoop wire of the mouth of the expandable filter when the mouth of the expandable filter is closed by the actuation wire; and
   an expandable introducer to at least assist in introducing the embolic protection device into the vasculature.

7. The embolic protection system of claim 6, wherein the embolic protection system includes a peel-away loading sleeve configured structurally to guide the embolic protection device into the expandable introducer, the loading sleeve comprising separable elements that can be parted by an operator to remove the loading sleeve from the embolic protection device, the separable elements defining, before separation, a lumen of the loading sleeve, the lumen sized to receive the embolic protection device into the expandable introducer.

8. The embolic protection system of claim 7, wherein the separable elements, before separation, are locked together by a twist-off locking cap, wherein removal by an operator of the locking cap allows separation of the separable elements.

* * * * *

UNITED STATES PATENT AND TRADEMARK OFFICE
CERTIFICATE OF CORRECTION

PATENT NO. : 12,232,948 B2
APPLICATION NO. : 17/893818
DATED : February 25, 2025
INVENTOR(S) : Huynh et al.

Page 1 of 1

It is certified that error appears in the above-identified patent and that said Letters Patent is hereby corrected as shown below:

In the Specification

In Column 9, Line 12, delete "700B." and insert --770B.-- therefor

In Column 9, Line 12, after "The", insert --parts--

In Column 9, Line 22, delete "of 772" and insert --772-- therefor

In Column 11, Line 38, delete "19I," and insert --19R,-- therefor

In Column 13, Line 51, delete "tip," and insert --tip;-- therefor

In the Claims

In Column 16, Line 9, in Claim 1, after "protection", delete a linebreak

Signed and Sealed this
Twenty-ninth Day of April, 2025

Coke Morgan Stewart
*Acting Director of the United States Patent and Trademark Office*